(12) United States Patent
Trova

(10) Patent No.: US 6,627,633 B2
(45) Date of Patent: *Sep. 30, 2003

(54) 6-SUBSTITUTED BIARYL PURINE DERIVATIVES AS POTENT CYCLIN/CDK INHIBITORS AND ANTIPROLIFERATIVE AGENTS

(75) Inventor: Michael Peter Trova, Schenectady, NY (US)

(73) Assignee: Albany Molecular Research, Inc., Albany, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/493,790

(22) Filed: Jan. 28, 2000

(65) Prior Publication Data

US 2003/0125342 A1 Jul. 3, 2003

Related U.S. Application Data

(60) Provisional application No. 60/124,829, filed on Mar. 17, 1999.

(51) Int. Cl.$^7$ ................ C07D 473/16; A61K 31/52; A61P 35/00; A61P 35/02; A61P 19/02
(52) U.S. Cl. .................. 514/263.2; 514/263.21; 514/263.22; 514/263.23; 514/263.4; 544/277
(58) Field of Search ............ 544/277; 514/261, 514/266, 263.4, 263.21, 263.22, 263.23, 263.2

(56) References Cited

U.S. PATENT DOCUMENTS

| 5,282,824 A | * | 2/1994 | Gianturco ............. 606/198 |
| 5,866,702 A | | 2/1999 | Mackman et al. ......... 544/344 |
| 6,316,456 B1 | * | 11/2001 | Meijer et al. ........... 544/277 |
| 6,413,974 B1 | * | 7/2002 | Dumont et al. .......... 544/277 |
| 6,479,487 B1 | * | 11/2002 | Dumont et al. .......... 544/277 |
| 2002/0032327 A1 | * | 3/2002 | Lum et al. .............. 544/277 |
| 2002/0035252 A1 | * | 3/2002 | Lum et al. .............. 544/277 |
| 2002/0091263 A1 | * | 7/2002 | Trova .................. 544/277 |

FOREIGN PATENT DOCUMENTS

| FR | 2 741 881 A | | 6/1997 |
| WO | WO 98/05335 | | 2/1998 |
| WO | 99/07705 | * | 2/1999 |
| WO | WO 99/43675 | | 9/1999 |
| WO | WO 99/43676 | | 9/1999 |

OTHER PUBLICATIONS

Gray, Current Medical Opinion 6, 859 (1999).
Perez–Roger, Current Pharma. Biotechnology 1, 107 (2000).
Brooks, DDT 4(10) 455 (1999).*
Coleman, Annual Reports in MEdicinal Chem., vol. 32, 171 (1997).*
Mani, Exp. Opinion Invest. Drugs 9(8) 1849 (2000).*
Fischer, Current Medicinal Chemistry 7, 1213 (2000).*
Steadman's MEdical Dictionary, 26th edition (Willimas and Williams) 1995, p. 1534.*
Mattson, Trends in Cardiovascular Medicine 5, 200 (1995).*
Nikol, Wien Klin Wochenschr 107(13) 379 (1995).*
http://americanheartassociation.com/Heart_and_Stroke_A_Z_Guide/sten.html.*

(List continued on next page.)

Primary Examiner—Mark L. Berch
(74) Attorney, Agent, or Firm—Nixon Peabody LLP

(57) ABSTRACT

The compounds of the present invention are 2,6,9-trisubstituted purine inhibitors of cyclin/cdk complexes. The compounds also are potent inhibitors of human cellular proliferation. As such, the compounds constitute pharmaceutical compositions with a pharmaceutically acceptable carrier. Such compounds are useful in inhibiting cellular proliferation in a mammal by administering to such mammal an effective amount of the compound. An example is represented by the following chemical structure:

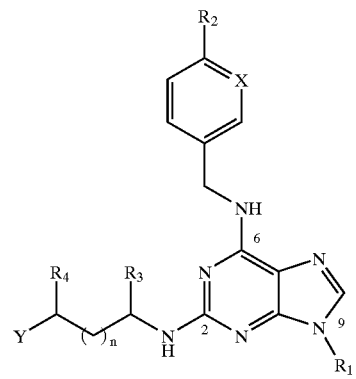

wherein:
X=N;
$R_2$=
  phenyl;
  substituted phenyl;
  1-naphthyl;
  2-naphthyl;
  heterocycles; or
  substituted heterocycle;
Y=
  H;
  $OR_1$;
  $NHR_1$;
  $NHC(O)R_3$;
  $NHSO_2R_3$;
  $NHC(O)NHR_3$;
  $NHC(O)R_5$; or
  $NHC(O)OR_6$;
and $R_1$, $R_3$, and $R_4$ are defined herein.

67 Claims, No Drawings

OTHER PUBLICATIONS

Schow et al., "Synthesis and Activity of 2,6,9–Trisubstituted Purines," *Bioorganic & Medicinal Chemistry Letters* 7(210:2697–2703 (1997).

Imbach et al., 2,6,9–Trisubstituted Purines: Optimization Towards Highly Potent and Selective CDK1 Inhibitors,: *Bioorganic & Medicinal Chemistry Letters* 9:91–96 (1999).

Legraverend et al., "Synthesis and In Vitro Evaluation of Novel 2,6,9–Trisubstituted Purines Acting as Cyclin–Dependent Kinase Inhibitors," *Bioorganic & Medicinal Chemistry* 7:1281–1293 (1999).

* cited by examiner

6-SUBSTITUTED BIARYL PURINE DERIVATIVES AS POTENT CYCLIN/CDK INHIBITORS AND ANTIPROLIFERATIVE AGENTS

This application claims benefit of U.S. Provisional Patent Application Ser. No. 60/124,829, filed Mar. 17, 1999.

FIELD OF THE INVENTION

The present invention relates to compounds that are shown to be potent cyclin/cyclin dependent kinase (cdk) inhibitors. Compounds with these properties are shown to be potent inhibitors of cell growth and proliferation. Such compounds can be used to treat the following conditions: rheumatoid arthritis, lupus, type 1 diabetes, multiple sclerosis, cancer, restenosis, gout and other proliferative diseases involving abnormal cellular proliferation. Compounds of the present invention which are biaryl substituted purine derivatives are shown to be potent antiproliferative agents against a number of human transformed cell lines, and also inhibitors of human cyclin/cdk kinase complexes.

BACKGROUND OF THE INVENTION

Cellular Proliferation and Cancer

The disruption of external or internal regulation of cellular growth can lead to uncontrolled proliferation and in cancer, tumor formation. This loss of control can occur at many levels and, indeed, does occur at multiple levels in most tumors. Further, although tumor cells can no longer control their own proliferation, they still must use the same basic cellular machinery employed by normal cells to drive their growth and replication.

Cyclin Dependent Kinases and Cell Cycle Regulation

Progression of the normal cell cycle from the G1 to S phase, and from the G2 phase to M phase is dependent on cdks (Sherr, C. J., *Science* 274:1672–1677 (1996)). Like other kinases, cdks regulate molecular events in the cell by facilitating the transfer of the terminal phosphate of adenosine triphosphate (ATP) to a substrate protein. Isolated cdks require association with a second subunit, called cyclins (Desai et al., *Mol. Cell. Biol.*, 15:345–350 (1995)). Cyclins cause conformational changes at the cdk active site, allowing ATP access and interaction with the substrate protein. The balance between its rates of synthesis and degradation controls the level of each cyclin at any point in the cycle (Elledge, S. J., et al., *Biochim. Biophys. Acta,* 1377:M61–M70 (1998)). The influences of cyclin/cdk activity on the cell cycle and cellular transformation are summarized in Table 1.

Abnormal Cyclin/cdk Activity in Cancer

In a normal cell, interlocking pathways respond to the cell's external environment and internal checkpoints monitor conditions within the cell to control the activity of cyclin/cdk complexes. A reasonable hypothesis is that the disruption of normal control of cyclin/cdk activity may result in uncontrolled proliferation. This hypothesis appears to hold in a number of tumor types in which cyclins are expressed at elevated levels (Table 1). Mutations in the genes encoding negative regulators (proteins) of cyclin/cdk activity are also found in tumors (Larsen, C.-J., *Prog. Cell Cycle Res.*, 3:109–124 (1997)); (Kamb, A., *Trends in Genetics*, 11:136–140 (1995)). Members of the Cip family of cdk inhibitors form a ternary complex with the cyclin/cdk and require binding to cyclinA, cyclinE, or cyclinD (Hall, M., et al., *Oncogene*, 11:1581–1588 (1995)). In contrast, Ink family members form a binary complex with cdk4 or cdk6 and prevent binding to cyclinD (Parry, D.; et al., *EMBO J.*, 14:503–511 (1995)).

TABLE 1

Associations Among Cyclins and Cancers

| Cyclin | Cell Cycle Role | Associated cdk | Cancer |
|---|---|---|---|
| A | S, G2 to M | cdk1, cdk2 | hepatocellular carcinoma (Wang, J.; et al., Oncogene, 8:1653–1656 (1992)) |
| B1/B2 | G2 to M | cdk1 | none yet defined |
| D1 | G1 | cdk4, cdk6 | parathyroid adenoma (Motokura, T., et al., Nature, 350:512–515 (1991)) centrocytic B cell lymphoma (Withers, D.A., et al., Mol. Cell. Biol., :4846–4853 (1991)) esophageal carcinoma (Jiang, W., et al. Cancer Res., 52:2980–2983 (1992)) breast cancer (Dickson, C., et al., Cancer Lett., 90:43–50 (1995)) squamous cell carcinoma (Bartkova, J., et al., Cancer Res., 55:949–956 (1995)) hepatocellular carcinoma (Nishida, N., et al., Cancer Res., 54:3107–3110 (1994)) |
| D2 | G1 | cdk4, cdk6 | colorectal carcinoma (Leach, F.S., et al., Cancer Res., 54:1986–1989 (1993)) |
| E | G1 to S | cdk2 | breast cancer (Keytomarsi, K., et al., Cancer Res., 54:380–385 (1994)) gastric carcinoma (Akama, Y.; et al., Jap. J. Cancer Res., 86:617–621 (1995)) colorectal carcinoma (Kitihara, K.; et al., Int. J. Cancer, 62:25–28 (1995)) |

Inhibitors of Cyclin/cdk Complexes as Potential Anticancer Agents

Tumors with elevated cyclin/cdk activity, whether from the over expression of cyclins or the loss of an endogenous cdk inhibitor, are prime targets for potential therapies based on small molecule cyclin/cdk inhibitors. In fact, several small molecule inhibitors of cyclin/cdks are reported (Meijer, L., et al., "Progress in Cell Cycle Research," Plenum Press: New York, 351–363 (1995)) and appear to bind at the ATP site of the kinase. Some information is known about small molecule inhibitors of other kinases, such as PKC (serine kinase) (Murray, K. J. et al., "Ann. Rep. Med. Chem.," J. Bristol, Ed., Academic Press, Inc.: New York, Chapter 26 (1994)) and tyrosine kinases (Fatl, W. J., et al., *Ann. Rev. Biochem.,* 62:453 (1993); Burke, T. R., *Drugs of the Future,* 17:119–1131 (1992); Dobrusin, E. M. et al., "Ann. Rep. Med. Chem," J. Bristol, Ed., Academic Press, Inc.: New York, Chapter 18 (1992); Spence, P., *Curr. Opin. Ther. Patents,* 3:3 (1993)). A number of known inhibitors were obtained from commercial sources or were synthesized by literature procedures.

Purine Compounds as Cyclin/cdk Inhibitors

There are several reports of 2,6-diamino substituted purine derivatives as cyclin/cdk inhibitors and as inhibitors of cellular proliferation. Among those are reports by U.S. Pat. No. 5,583,137 to Coe, et al., olomoucine (Vesely, J., et al., *Eur. J. Biochem.,* 224:771–786 (1994)), roscovitine (Meijer, L., *Eur. J. Biochem.,* 243:527–536 (1997)), WO 97/16452 to Zimmerman, Imbach, P., et al., *Bioorg. Med. Chem. Lett.,* 9:91–96 (1999), Norman, T. C., et al., *J. Amer. Chem. Soc.,* 118:7430–7431 (1996), Gray, N. S., et al., *Tetrahedron Lett.,* 38:1161–1164 (1997), Gray, N. S., et al., *Science,* 281:533–538 (1998), WO 98/05335 to Lum, et al., Schow, S. R., et al., *Bioorg. Med. Chem. Lett,* 7:2697–2702 (1997), U.S. Pat. No. , 5,886,702 to Mackman, et al., Nugiel, D. A., et al., *J. Org. Chem.,* 62:201–203 (1997), and Fiorini. M. T. et al., *Tetrahedron Lett.,* 39:1827–1830 (1998). Many of these reported compounds are shown to inhibit cyclin/cdk complexes and have modest cellular proliferation inhibition properties.

The compounds of the present invention are shown to have far superior biological activities as cyclin/cdk complex inhibitors as well as inhibitors of cellular proliferation compared to those previously reported. In fact, the art (e.g., Fiorini, M. T. et al., *Tetrahedron Lett.*, 39:1827–1830 (1998)) teaches away from compounds of this invention, claiming lack of cellular proliferation inhibition.

SUMMARY OF THE INVENTION

The compounds of the present invention are 2,6,9-trisubstituted purine derivatives which are inhibitors of cyclin/cdk complexes. The compounds of the current invention also are potent inhibitors of human cellular proliferation. As such, the compounds of the present invention constitute pharmaceutical compositions with a pharmaceutically acceptable carrier. Such compounds are useful in inhibiting cellular proliferation in a mammal by administering to such mammal an effective amount of the compound.

In one embodiment, the compounds of the present invention are represented by the chemical structure found in Formula I

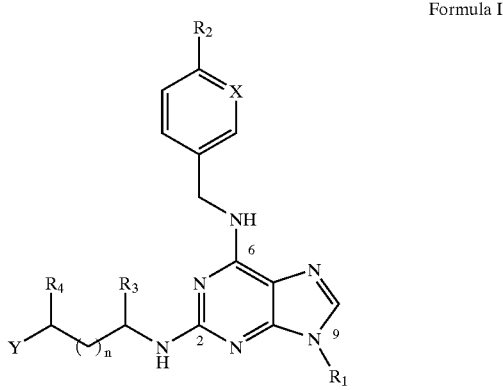

Formula I wherein:
  $R_1$ are the same or different and independently selected from:
    H;
    $C_1$–$C_4$-straight chain alkyl;
    $C_3$–$C_4$-branched chain alkyl;
  X=
    N;
    CH;
  $R_2$=
    phenyl;
    substituted phenyl, wherein the substituents (1–2 in number) are in any position and are independently selected from $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, $C(O)NHCHR_1CH_2OH$;
    1-naphthyl;
    2-naphthyl;
    heterocycles including:
      2-pyridyl;
      3-pyridyl;
      4-pyridyl;
      5-pyrimidyl;
      thiophene-2-yl;
      thiophene-3-yl;
      2-furanyl;
      3-furanyl;
      2-benzofuranyl;
      benzothiophene-2-yl;
      2-pyrrolyl;
      3-pyrrolyl;
      2-quinolinyl;
      3-quinolinyl;
      4-quinolinyl;
      1-isoquinolinyl;
      3-isoquinolinyl;
      4-isoquinolinyl;
    substituted heterocycle, wherein the substituents (1–2 in number) are in any position and are independently selected from Br, Cl, F, $R_1$, $C(O)CH_3$;
  $R_3$ are the same or different and independently selected from:
    H;
    $C_1$–$C_4$-straight chain alkyl;
    $C_3$–$C_4$-branched chain alkyl;
    $C_2$–$C_4$-alkenyl chain;
    $(CH_2)_n Ph$;
    $(CH_2)_n$-substituted phenyl, wherein the phenyl substituents are as defined above in $R_2$;
  $R_4$=
    H;
    $C_1$–$C_4$-straight chain alkyl;
    $C_3$–$C_4$-branched chain alkyl;
  $R_3$ and $R_4$ can be linked together by a carbon chain to form a 5–8-membered ring;
  n=0–3;
  Y=
    H;
    $OR_1$;
    $NHR_1$;
    $NHC(O)R_3$;
    $NHSO_2R_3$;
    $NHC(O)NHR_3$;
    $NHC(O)R_5$;
    $NHC(O)OR_6$;
  $R_5$=$C_3$–$C_7$-cycloalkyl;
  $R_6$=
    $C_1$–$C_4$-straight chain alkyl;
    $C_3$–$C_4$-branched chain alkyl;
    $C_2$–$C_4$-alkenyl chain;
    $(CH_2)_n Ph$;
    $(CH_2)_n$-substituted phenyl, wherein the phenyl substituents are as defined above in $R_2$;
  or a pharmaceutically acceptable salt thereof, with the proviso that when $R_1$=$CH(CH_3)_2$, and $R_2$=Ph, and X=CH, then $R_3 \neq H$, and n≠0, and $R_4 \neq H$ and Y≠OH.

Another aspect of the present invention is directed to a compound of the following formula:

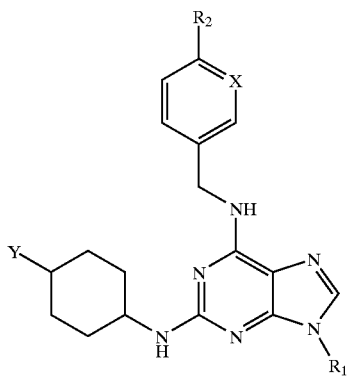

Formula III wherein:

R₁ are the same or different and independently selected from:
H;
$C_1$–$C_4$-straight chain alkyl;
$C_3$–$C_4$-branched chain alkyl;

X=
N;
CH;

R₂=
phenyl;
substituted phenyl, wherein the substituents (1–2 in number) are in any position and independently selected from R₁, OR₁, SR₁, S(O)R₁, S(O₂)R₁, NHR₁, NO₂, OC(O)CH₃, NHC(O)CH₃, F, Cl, Br, CF₃, C(O)R₁, C(O)NHR₁, phenyl, C(O)NHCHR₁CH₂OH;
heterocycles including:
2-pyridyl;
3-pyridyl;
4-pyridyl;
5-pyrimidyl;
thiophene-2-yl;
thiophene-3-yl;
2-furanyl;
3-furanyl;
2-benzofuranyl;
benzothiophene-2-yl;
2-pyrrolyl;
3-pyrrolyl;
2-quinolinyl;
3-quinolinyl;
4-quinolinyl;
1-isoquinolinyl;
3-isoquinolinyl;
4-isoquinolinyl;
substituted heterocycle, wherein the substituents (1–2 in number) are in any position and are independently selected from Br, Cl, F, R₁, C(O)CH₃;

Y=
OR₁;
NHR₁;
NHC(O)R₁;
NHSO₂R₁;
NHC(O)NHR₁;
NHC(O)OR₆; or a pharmaceutically acceptable salt thereof, R₆=
$C_1$–$C_4$-straight chain alkyl;
$C_3$–$C_4$-branched chain alkyl;
$C_2$–$C_4$-alkenyl chain;
or a pharmaceutically acceptable salt thereof.

The present invention is also directed to a process for preparation of a purine derivative compound of the formula:

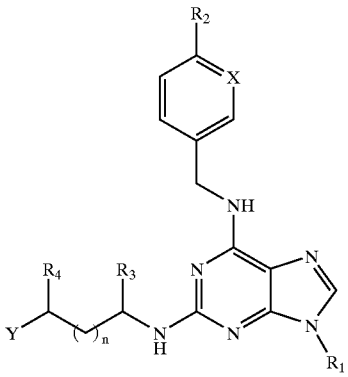

Formula XVIII wherein:

R₁=
H;
$C_1$–$C_4$-straight chain alkyl;
$C_3$–$C_4$-branched chain alkyl;

X=
N;
CH;

R₂=
phenyl;
substituted phenyl, wherein the substituents (1–2 in number) are in any position and are independently selected from R₁, OR₁, SR₁, S(O)R₁, S(O₂)R₁, NHR₁, NO₂, OC(O)CH₃, NHC(O)CH₃, F, Cl, Br, CF₃, C(O)R₁, C(O)NHR₁, phenyl, C(O)NHCHR₁CH₂OH;
1-naphthyl;
2-naphthyl;
heterocycles including:
2-pyridyl;
3-pyridyl;
4-pyridyl;
5-pyrimidyl;
thiophene-2-yl;
thiophene-3-yl;
2-furanyl;
3-furanyl;
2-benzofuranyl;
benzothiophene-2-yl;
2-pyrrolyl;
3-pyrrolyl;
2-quinolinyl;
3-quinolinyl;
4-quinolinyl;
1-isoquinolinyl;
3-isoquinolinyl;
4-isoquinolinyl;
substituted heterocycle, wherein the substituents are in any position and are selected from Br, Cl, F, R₁, C(O)CH₃;

R₃=
H;
$C_1$–$C_4$-straight chain alkyl;
$C_3$–$C_4$-branched chain alkyl;

$C_2$–$C_4$-alkenyl chain;

$(CH_2)_n$Ph;

$(CH_2)_n$-substituted phenyl, wherein the phenyl substituents are as defined above in $R_2$;

$R_4=$

H;

$C_1$–$C_4$-straight chain alkyl;

$C_3$–$C_4$-branched chain alkyl;

$R_3$ and $R_4$ can be linked together by a carbon chain to form a 5–8-membered ring;

n=0–3;

Y=

H;

$OR_1$;

$NHR_1$;

$NHC(O)R_3$;

$NHSO_2R_3$;

$NHC(O)NHR_3$;

$NHC(O)R_5$;

$NHC(O)OR_6$;

$R_5=C_3$–$C_7$-cYcloalkyl;

$R_6=$ $C_1$–$C_4$-straight chain alkyl;

$C_3$–$C_4$-branched chain alkyl;

$C_2$–$C_4$-alkenyl chain;

$(CH_2)_n$Ph;

$(CH_2)_n$-substituted phenyl, wherein the phenyl substituents are as defined above in $R_2$; or a pharmaceutically acceptable salt thereof with the proviso that when $R_1$=CH(CH$_3$)$_2$, and $R_2$=Ph, and X=CH, then $R_3 \neq$H, and n$\neq$0, and $R_4 \neq$H, and Y$\neq$OH, said process comprising:

reacting a compound of the formula:

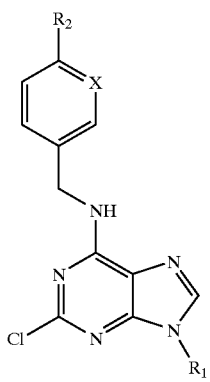

Formula XVII with a compound of the formula:

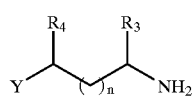

Formula VIII under conditions effective to form the purine derivative compound.

Another aspect of the present invention is directed to a process for preparation of a purine derivative compound of the formula:

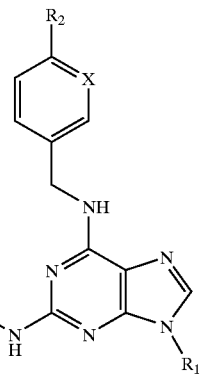

Formula X wherein:

$R_1$ are the same or different and independently selected from:

H;

$C_1$–$C_4$-straight chain alkyl;

$C_3$–$C_4$-branched chain alkyl;

X=

N;

CH;

$R_2=$ phenyl;

substituted phenyl, wherein the substituents (1–2 in number) are in any position and are independently selected from $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, $C(O)NHCHR_1CH_2OH$;

1-naphthyl;

2-naphthyl;

heterocycles including:

2-pyridyl;

3-pyridyl;

4-pyridyl;

5-pyrimidyl;

thiophene-2-yl;

thiophene-3-yl;

2-furanyl;

3-furanyl;

2-benzofuranyl;

benzothiophene-2-yl;

2-pyrrolyl;

3-pyrrolyl;

2-quinolinyl;

3-quinolinyl;

4-quinolinyl;

1-isoquinolinyl;

3-isoquinolinyl;

4-isoquinolinyl;

substituted heterocycle, wherein the substituents (1–2 in number) are in any position and are selected from Br, Cl, F, $R_1$, $C(O)CH_3$;

$R_3$ are the same or different and independently selected from:

H;

$C_1$–$C_4$-straight chain alkyl;

$C_3$–$C_4$-branched chain alkyl;

$C_2$–$C_4$-alkenyl chain;

$(CH_2)_n$Ph;

$(CH_2)_n$-substituted phenyl, wherein the phenyl substituents are as defined above in $R_2$;

$R_4$=
  H;
  $C_1$–$C_4$-straight chain alkyl;
  $C_3$–$C_4$-branched chain alkyl;
$R_3$ and $R_4$ can be linked together by a carbon chain to form a 5–8-membered ring;
n=0–3;
Y=
  H;
  $OR_1$;
  $NHR_1$;
  $NHC(O)R_3$;
  $NHSO_2R_3$;
  $NHC(O)NHR_3$;
  $NHC(O)R_5$;
  $NHC(O)OR_6$;
$R_5$=$C_3$–$C_7$-cycloalkyl;
$R_6$=
  $C_1$–$C_4$-straight chain alkyl;
  $C_3$–$C_4$-branched chain alkyl;
  $C_2$–$C_4$-alkenyl chain;
  $(CH_2)_n$Ph;
  $(CH_2)_n$-substituted phenyl, wherein the phenyl substituents are as defined above in $R_2$; or a pharmaceutically acceptable salt thereof,
with the proviso that when $R_1$=$CH(CH_3)_2$ and $R_2$=Ph and X=CH, then $R_3 \neq H$, and $n \neq 0$, and $R_4 \neq H$, and $Y \neq OH$, said process comprising:
  reacting a compound of the formula:

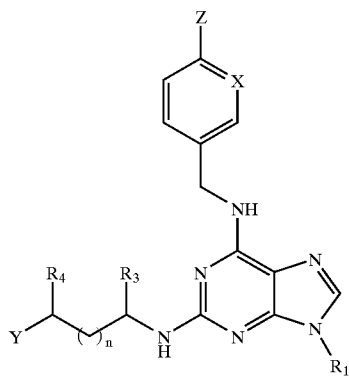

Formula IX wherein
Z=Br or I
with a compound of the formula: $R_2$—$B(OH)_2$, $R_2$—$Sn(n-Bu)_3$, $R_2$—$Sn(Me)_3$, or mixtures thereof, under conditions effective to form the purine derivative compound.

The compounds of the present invention, as described in Formula I, show significantly improved growth inhibition of human transformed cell lines and/or cyclin/cdk inhibition relative to compounds of the prior art. These compounds have been demonstrated to be potent growth inhibitors in dozens of human transformed cell lines. Olomoucine, a structurally related purine derivative, is a poor human transformed cell growth inhibition agent with $GI_{50}$ values in the 20,000–100,000 nM range over 60-transformed cell lines. By contrast, the compounds of the present invention demonstrate $GI_{50}$ values over 60-transformed cell lines in the <10–25.000 nM range, preferably in the <10–100 nM range over 60-transformed cell lines, and, most preferably, <10 nM across 60-human transformed cell lines. This finding is unexpected from the prior art, which specifically teaches that compounds of the present invention would not be potent human transformed cell line growth inhibitors.

The $R_2$ group in Formula I imparts unexpected and significant improvement in growth inhibition in human transformed cell lines, while substitution of various groups at $R_3$ and $R_4$ found in Formula I impart important features that contribute to cyclin/cdk inhibition and growth inhibition of human transformed cell lines. Specifically, the combination of the $R_2$ group and the substitutions within $R_3$ and $R_4$ result in compounds with superior biological activity. Compounds which are cyclin/cdk inhibitors and/or human transformed cell line growth inhibitors have utility in treating human proliferative cellular disorders.

DETAILED DESCRIPTION OF THE INVENTION

The compounds of the present invention are represented by the chemical structure found in Formula II.

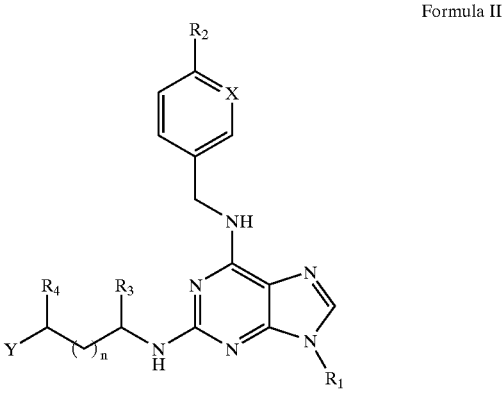

Formula II wherein:
  $R_1$ are the same or different and independently selected from:
    H;
    $C_1$–$C_4$-straight chain alkyl;
    $C_3$–$C_4$-branched chain alkyl;
  X=
    N;
    CH;
  $R_2$=
    phenyl;
    substituted phenyl, wherein the substituents (1–2 in number) are in any position and independently selected from $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $Cl_3$, $C(O)R_1$, $C(O)NHR_1$, phenyl, $C(O)NHCHR_1CH_2OH$;
    1-naphthyl;
    2-naphthyl;
    heterocycles including:
      2-pyridyl;
      3-pyridyl;
      4-pyridyl;
      5-pyrimidyl;
      thiophene-2-yl;
      thiophene-3-yl;
      2-furanyl;
      3-furanyl;
      2-benzofuranyl;
      benzothiophene-2-yl;
      2-pyrrolyl;
      3-pyrrolyl;

2-quinolinyl;
3-quinolinyl;
4-quinolinyl;
1-isoquinolinyl;
3-isoquinolinyl;
4-isoquinolinyl;
substituted heterocycle, wherein the substituents (1–2 in number) are in any position and are independently selected from Br, Cl, F, $R_1$, $C(O)CH_3$;

$R_3$ are the same or different and independently selected from:
H;
$C_1$–$C_4$-straight chain alkyl;
$C_3$–$C_4$-branched chain alkyl;

$R_4$=
H;
$C_1$–$C_4$-straight chain alkyl;
$C_3$–$C_4$-branched chain alkyl;

$R_3$ and $R_4$ can be linked together by a carbon chain to form a 5–8-membered ring;

n=0–3;

Y=
H;
$OR_1$;
$NHR_1$;
$NHC(O)R_3$;
$NHSO_2R_3$;
$NHC(O)NHR_3$; or a pharmaceutically acceptable salt thereof;

with the proviso that when $R_1=CH(CH_3)_2$, and $R_2=Ph$, and X=CH, then $R_3 \neq H$, and $n \neq 0$, and $R_4 \neq H$, and $Y \neq OH$.

More preferably, the compounds of the current invention are represented by the chemical structure found in Formula III.

Formula III

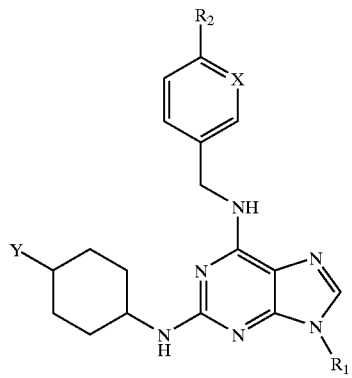

wherein:

$R_1$ are the same or different and independently selected from:
H;
$C_1$–$C_4$-straight chain alkyl;
$C_3$–$C_4$-branched chain alkyl;

X=
N;
CH;

$R_2$=
phenyl;
substituted phenyl, wherein the substituents (1–2 in number) are in any position and independently selected from $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, $C(O)NHCHR_1CH_2OH$;

heterocycles including:
2-pyridyl;
3-pyridyl;
4-pyridyl;
5-pyrimidyl;
thiophene-2-yl;
thiophene-3-yl;
2-furanyl;
3-furan yl;
2-benzofuranyl;
benzothiophene-2-yl;
2-pyrrolyl;
3-pyrrolyl;
2-quinolinyl;
3-quinolinyl;
4-quinolinyl;
1-isoquinolinyl;
3-isoquinolinyl;
4-isoquinolinyl;
substituted heterocycle, wherein the substituents (1–2 in number) are in any position and are independently selected from Br, Cl, F, $R_1$, $C(O)CH_3$;

Y=
$OR_1$;
$NHR_1$;
$NHC(O)R_1$;
$NHSO_2R_1$;
$HC(O)NHR_1$;
$NHC(O)OR_6$; or a pharmaceutically acceptable salt thereof;

$R_6$=
$C_1$–$C_4$-straight chain alkyl;
$C_3$–$C_4$-branched chain alkyl;
$C_2$–$C_4$-alkenyl chain;
or a pharmaceutically acceptable salt thereof.

In another embodiment, the present invention is directed to a method for inhibiting cellular proliferation in mammals comprising administering a therapeutically effective amount of the compound of the present invention to the mammal.

The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as. tablets, capsules, powders, solutions, suspensions, or emulsions.

Based on the results obtained in the standard pharmacological test procedures described below, the compounds of the present invention are useful as antineoplastic agents. More particularly, the compounds of the present invention are useful for inhibiting the growth of neoplastic cells, causing cell death of neoplastic cells, and eradicating neoplastic cells. The compounds of the present invention are, therefore, useful for treating solid tumors, including sarcomas and carcinomas, such as astrocytomas, prostate cancer, breast cancer, small cell lung cancer, and ovarian cancer, leukemias, lymphomas, adult T-cell leukemia/lymphoma. and other neoplastic disease states.

In addition to the utilities described above, many of the compounds of the present invention are useful in the preparation of other compounds.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain. in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterallly. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

General Synthetic Schemes

The compounds of the present invention can be prepared by conventional methods of organic synthesis practiced by those skilled in the art. The general reaction sequences outlined below are general methods useful for preparing the compounds of the present invention and are not meant to be limiting in scope or utility.

Reaction of 2,6-dichloropurine (Formula IV) with various amines of Formula V in the presence of a polar solvent, such as ethanol, provides purines of Formula VI (General Flowsheet I, infra). Reaction of purines of Formula VI with alkyl halides ($R_1$—Z) in the presence of a base such as potassium carbonate provides N1-alkylated purines of Formula VII. Chloride displacement with N-alkylated purines of Formula VII with amines of structure Formula VIII in an inert solvent such as ethanol or butanol at an appropriate temperature provides purines of Formula IX. Transition metal-mediated cross-coupling reaction of purines of Formula IX with boronic acid ($R_2$—$B(OH)_2$) or tin reagents ($R_2$—$Sn(n-Bu)_3$ or $R_2$—$SnMe_3$) provides purines of Formula X. If in Formula X (Y=$NH_2$), then subsequent reaction of Formula X (Y=$NH_2$) with acid chloride ($R_3COCl$), or sulfonyl chloride ($R_3SO_2Cl$). or isocyanate ($R_3NCO$), or chloroformate (ClC(O)$OR_6$) reagents provides purines of Formula XI wherein Y=NHC(O)$R_3$, NHSO$_2R_3$, or NHC(O)NHR$_3$, or NHC(O)OR$_6$, respectively. On the other hand, if in Formula X, Y already is OR$_1$ or NHC(O)R$_3$ or NHSO$_2R_3$ or NHC(O)NHR$_3$ or NHC(O)OR$_6$, as a result of what Y started out as in Formula VIII, then this last step is unnecessary.

Definitions of the groups include:

$R_1$ are the same or different and independently selected from:
- H;
- $C_1$–$C_4$-straight chain alkyl;
- $C_3$–$C_4$-branched chain alkyl;

X=
- N:
- CH;

Z=
- Br;
- I;

$R_2$=
- phenyl;
- substituted phenyl, wherein the substituents (1–2 in number) are in any position and independently selected from $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, $C(O)NHCHR_1CH_2OH$;
- 1-naphthyl;
- 2-naphthyl;
- heterocycles including:
  - 2-pyridyl;
  - 3-pyridyl;
  - 4-pyridyl;
  - 5-pyrimidyl;
  - thiophene-2-yl;
  - thiophene-3-yl;
  - 2-furanyl;
  - 3-furanyl;
  - 2-benzofuranyl;
  - benzothiophene-2-yl;
  - 2-pyrrolyl;
  - 3-pyrrolyl;
  - 2-quinolinyl;
  - 3-quinolinyl;
  - 4-quinolinyl;
  - 1-isoquinolinyl;
  - 3-isoquinolinyl;
  - 4-isoquinolinyl;
- substituted heterocycle, wherein the substituents (1–2 in number) are in any position and are independently selected from Br, Cl, F, $R_1$, $C(O)CH_3$;

$R_3$ are the same or different and independently selected from:

H;
$C_1$–$C_4$-straight chain alkyl;
$C_3$–$C_4$-branched chain alkyl;
$C_2$–$C_4$-alkenyl chain;
$(CH_2)_n$Ph;
$(CH_2)_n$-substituted phenyl, wherein the phenyl substituents are as defined above in $R_2$;

$R_4=$
H;
$C_1$–$C_4$-straight chain alkyl;
$C_3$–$C_4$-branched chain alkyl;

$R_3$ and $R_4$ can be linked together by a carbon chain to form a 5–8-membered ring:
n=0–3;
Y=
H;
$OR_1$;
$NHR_1$;
$NHC(O)R_3$;
$NHSO_2R_3$;
$NHC(O)NHR_3$;
$NHC(O)OR_6$;

$R_6=$
$C_1$–$C_4$-straight chain alkyl;
$C_3$–$C_4$-branched chain alkyl;
$C_3$–$C_7$-cycloalkyl;
$C_2$–$C_4$-alkenyl chain;
$(CH_2)_n$Ph;
$(CH_2)_n$-substituted phenyl, wherein the phenyl substituents are as defined above in $R_2$.

General Flowsheet I

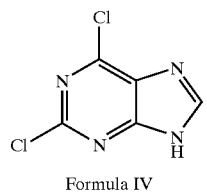

Formula IV

+

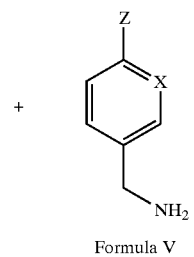

Formula V

Solvent

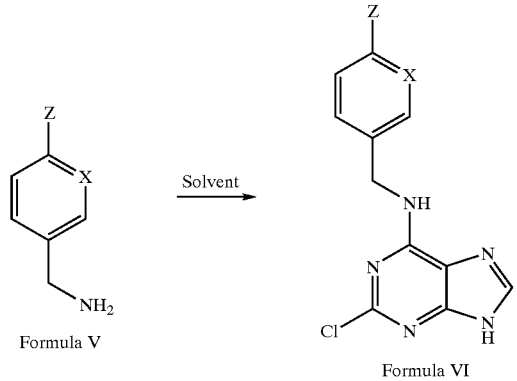

Formula VI $R_1$—Z; base

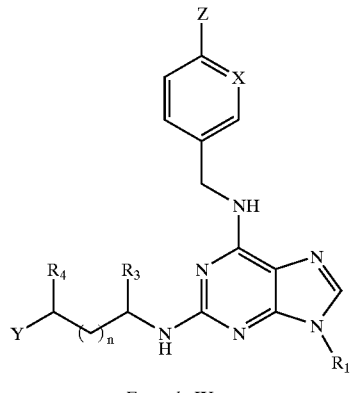

Formula IX

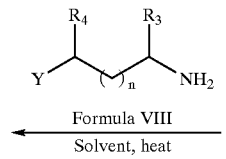

Formula VIII
Solvent, heat

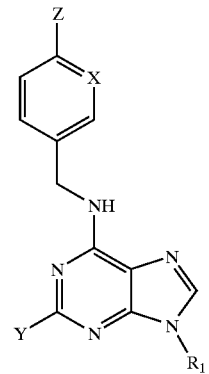

Formula VII $R_2$—B(OH)$_2$
or
$R_2$—Sn(n-Bu)$_3$
or
$R_2$—Sn(Me)$_3$;
Pd(0) catalyst -continued
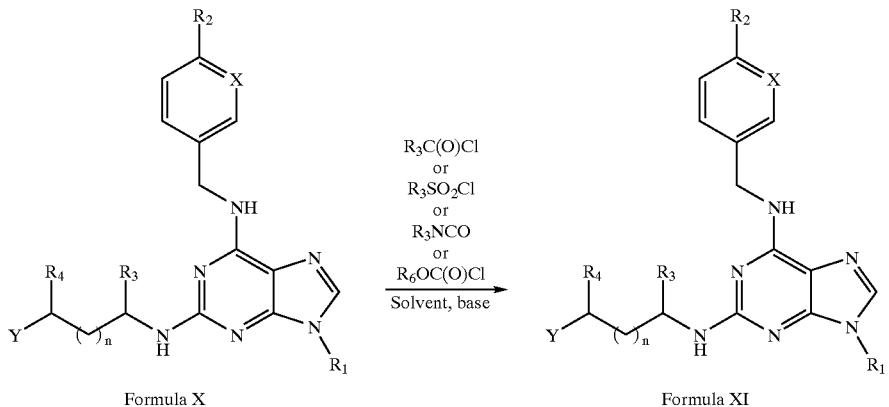
General non-limiting syntheses of compounds of the present invention of Formula XVIII and Formula XIX are shown below.
General Flowsheet II
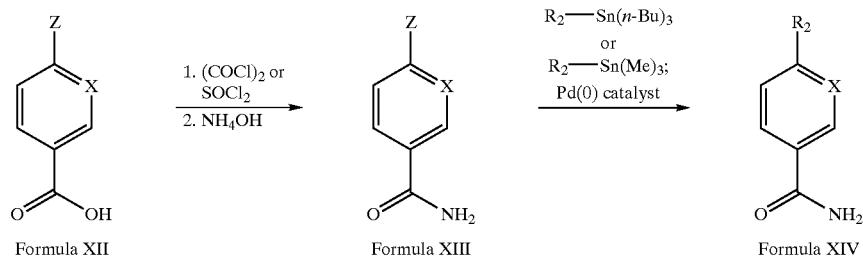
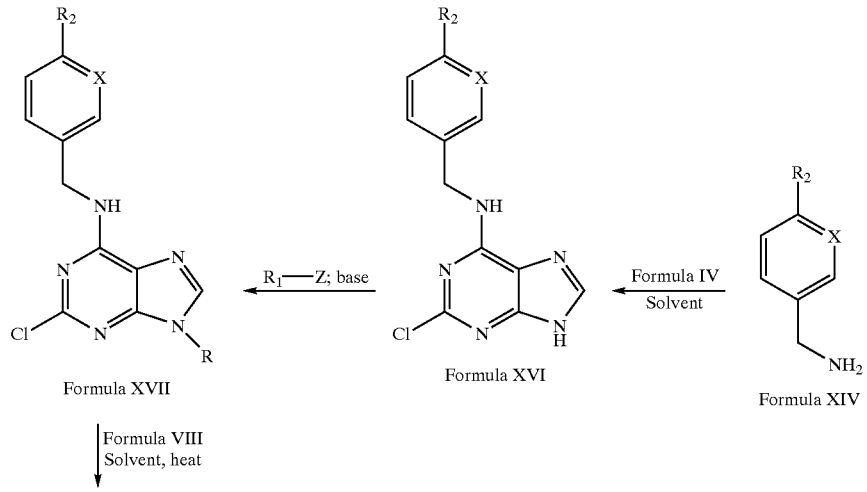

-continued

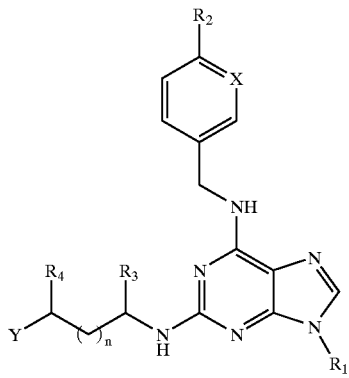

Formula XVIII

R$_3$C(O)Cl
or
R$_3$SO$_2$Cl
or
R$_3$NCO
or
R$_6$OC(O)Cl
Solvent, base
→

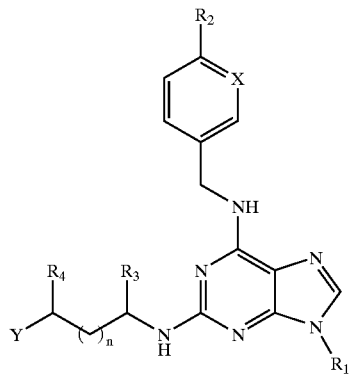

Formula XIX

Reaction of acids of Formula XII with oxalyl chloride or thionyl chloride followed by reaction with ammonium hydroxide provides amides of Formula XIII (General Flowsheet II). Transition metal-mediated cross-coupling reaction of amides of Formula XIII with boronic acid (R$_2$—B(OH)$_2$) or tin reagents (R$_2$—Sn(n-Bu)$_3$) or (R$_2$—SnMe$_3$) provides amides of Formula XIV. Reduction of amides of Formula XIV with a reducing agent in an appropriate solvent provides amines of Formula XV. Reaction of amines of Formula XV with 2,6-dichloropurine (Formula IV) in the presence of a polar solvent, such as ethanol, provides purines of Formula XVI. Reaction of purines of Formula XVI with alkyl halides (R$_1$—Z) in the presence of a base such as potassium carbonate provides N1-alkylated purines of Formula XVII. Chloride displacement of purines of Formula XVII with amines of Formula VIII in an inert solvent such as ethanol or butanol at an appropriate temperature provides purines of Formula XVIII. If in Formula XVIII (Y=NH$_2$), then subsequent reaction of Formula XVIII (Y=NH$_2$) with acid chloride R$_3$COCl), or sulfonyl chloride (R$_3$SO$_2$Cl), or isocyanate (R$_3$NCO), or chloroformate (ClC(O)OR$_6$) reagents provides purines of Formula XIX wherein Y=NHC(O)R$_3$, or NHSO$_2$R$_3$, or NHC(O)NHR$_3$, or NHC(O)OR$_6$, respectively. On the other hand, if in Formula XVIII, Y already is OR$_1$ or NHC(O)R$_3$ or NHSO$_2$R$_3$ or NHC(O)NHR$_3$ or NHC(O)OR$_6$, as a result of what Y started out as in Formula VIII, then this last step is unnecessary.

Definitions of the groups include:

R$_1$ are the same or different and independently selected from:
  H;
  C$_1$–C$_4$-straight chain alkyl;
  C$_3$–C$_4$-branched chain alkyl;

X=
  N;
  CH;

Z=
  Br;
  I;

R$_2$=
  phenyl;
  substituted phenyl, wherein the substituents (1–2 in number) are in any position and independently selected from R$_1$, OR$_1$, SR$_1$, S(O)R$_1$, S(O$_2$)R$_1$, NHR$_1$, NO$_2$, OC(O)CH$_3$, NHC(O)CH$_3$, F, Cl, Br, CF$_3$, C(O)R$_1$, C(O)NHR$_1$, phenyl, C(O)NHCHR$_1$CH$_2$OH;
  1-naphthyl;
  2-naphthyl;
  heterocycles including:
    2-pyridyl;
    3-pyridyl;
    4-pyridyl;
    5-pyrimidyl;
    thiophene-2-yl;
    thiophene-3-yl;
    2-furanyl;
    3-furanyl;
    2-benzofuranyl;
    benzothiophene-2-yl;
    2-pyrrolyl;
    3-pyrrolyl;
    2-quinolinyl;
    3-quinolinyl;
    4-quinolinyl;
    1-isoquinolinyl;
    3-isoquinolinyl;
    4-isoquinolinyl;
  substituted heterocycle, wherein the substituents (1–2 in number) are in any position and are independently selected from Br, Cl, F, R$_1$, C(O)CH$_3$;

R$_3$ are the same or different and independently selected from:
  H;
  C$_1$–C$_4$-straight chain alkyl;
  C$_3$–C$_4$-branched chain alkyl;
  C$_2$–C$_4$-alkenyl chain;
  (CH$_2$)$_n$Ph;
  (CH$_2$)$_n$-substituted phenyl, wherein the phenyl substituents are as defined above in R$_2$;

R$_4$=
  H;
  C$_1$–C$_4$-straight chain alkyl;
  C$_3$–C$_4$-branched chain alkyl;

R$_3$ and R$_4$ can be linked together by a carbon chain to form a 5–8-membered ring;

n=0–3;

Y=
  H;
  OR$_1$;
  NHR$_1$;
  NHC(O)R$_3$;
  NHSO$_2$R$_3$;
  NHC(O)NHR$_3$;
  NHC(O)OR$_6$;

R$_6$=

$C_1$–$C_4$-straight chain alkyl;
$C_3$–$C_4$-branched chain alkyl;
$C_3$–$C_7$-cycloalkyl;
$C_2$–$C_4$-alkenyl chain;
$(CH_2)_n Ph$;
$(CH_2)_n$-substituted phenyl, wherein the phenyl substituents are as defined above in $R_2$.
The synthesis of compound 5 is shown below in Scheme I.
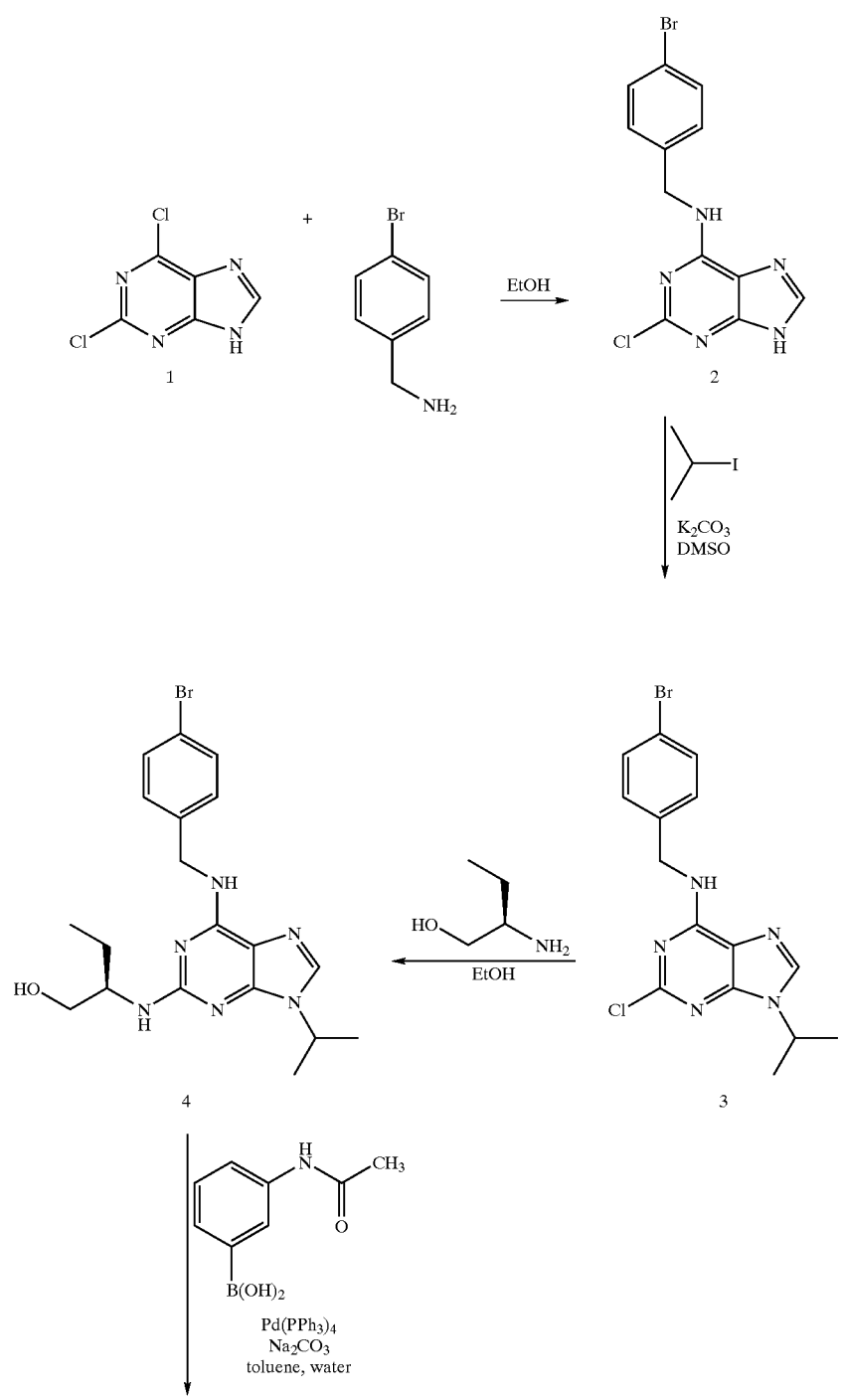
Scheme I

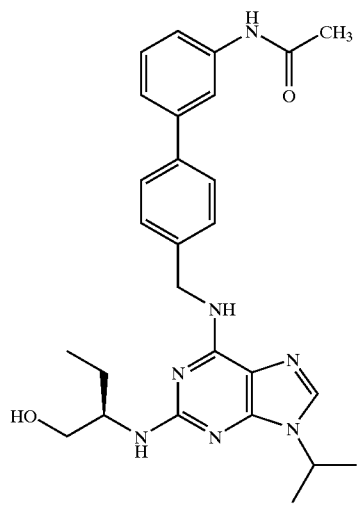
5
The synthesis of compound 11 is shown below in Scheme II.
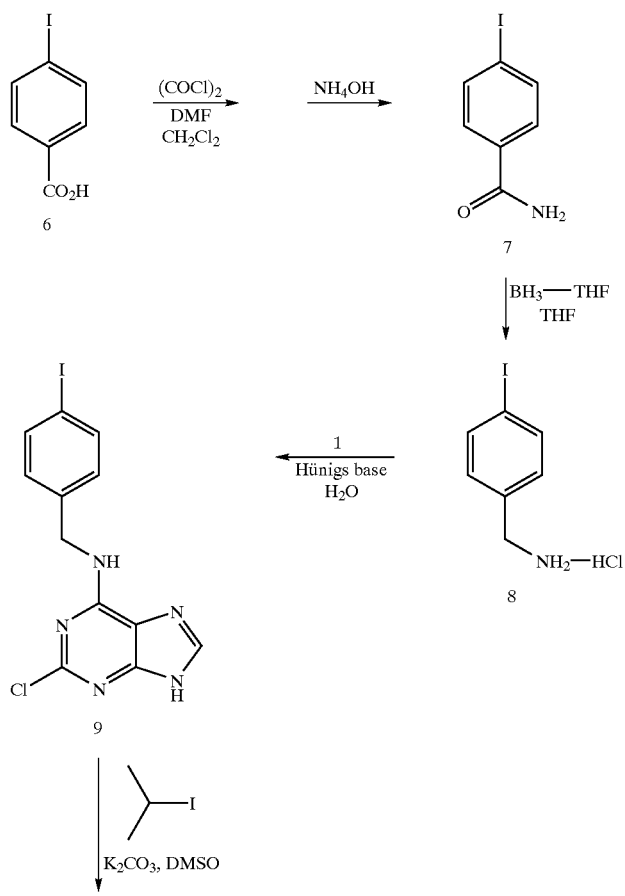

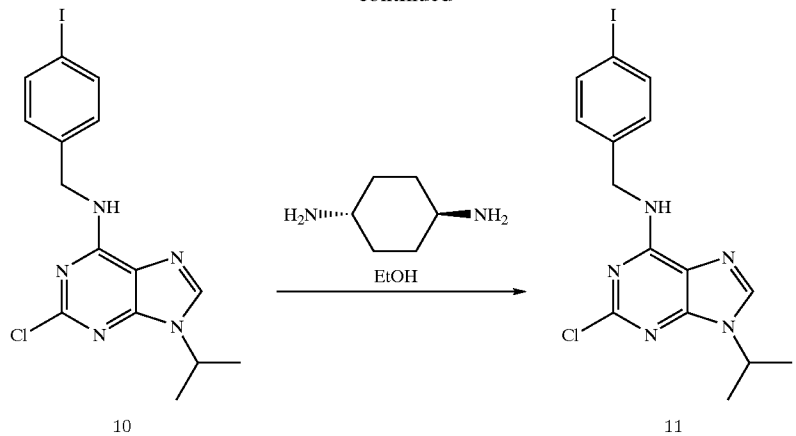
The syntheses of compounds 12, 13 and 14 are shown below in Scheme III.
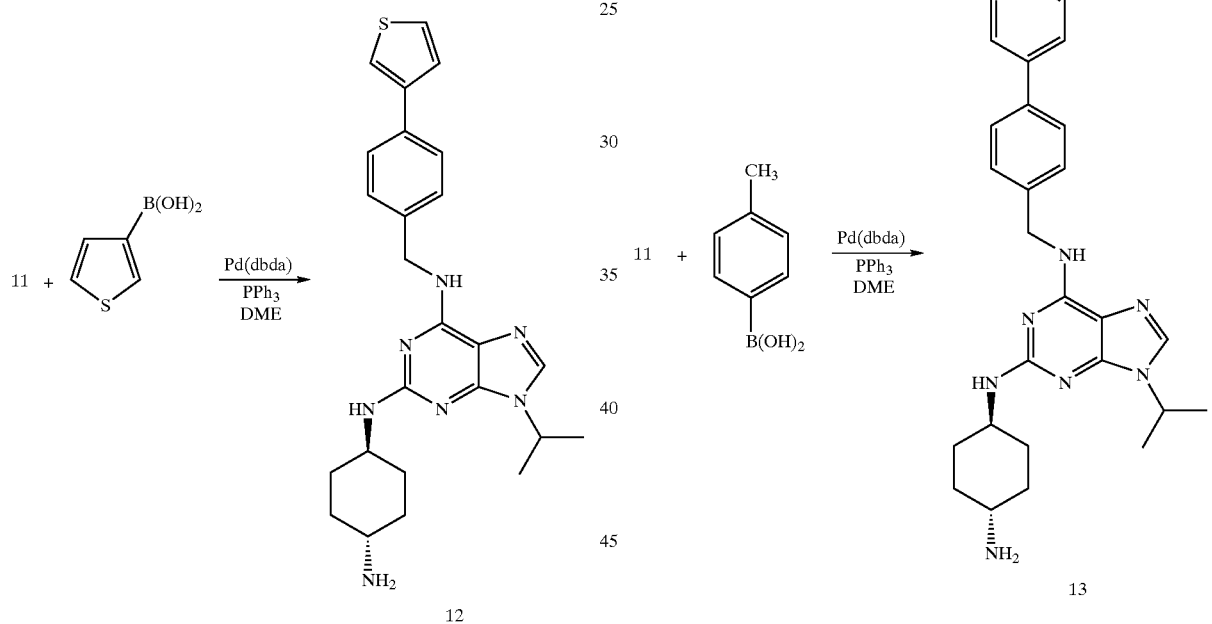

The synthesis of compound 17 is shown below in Scheme IV.
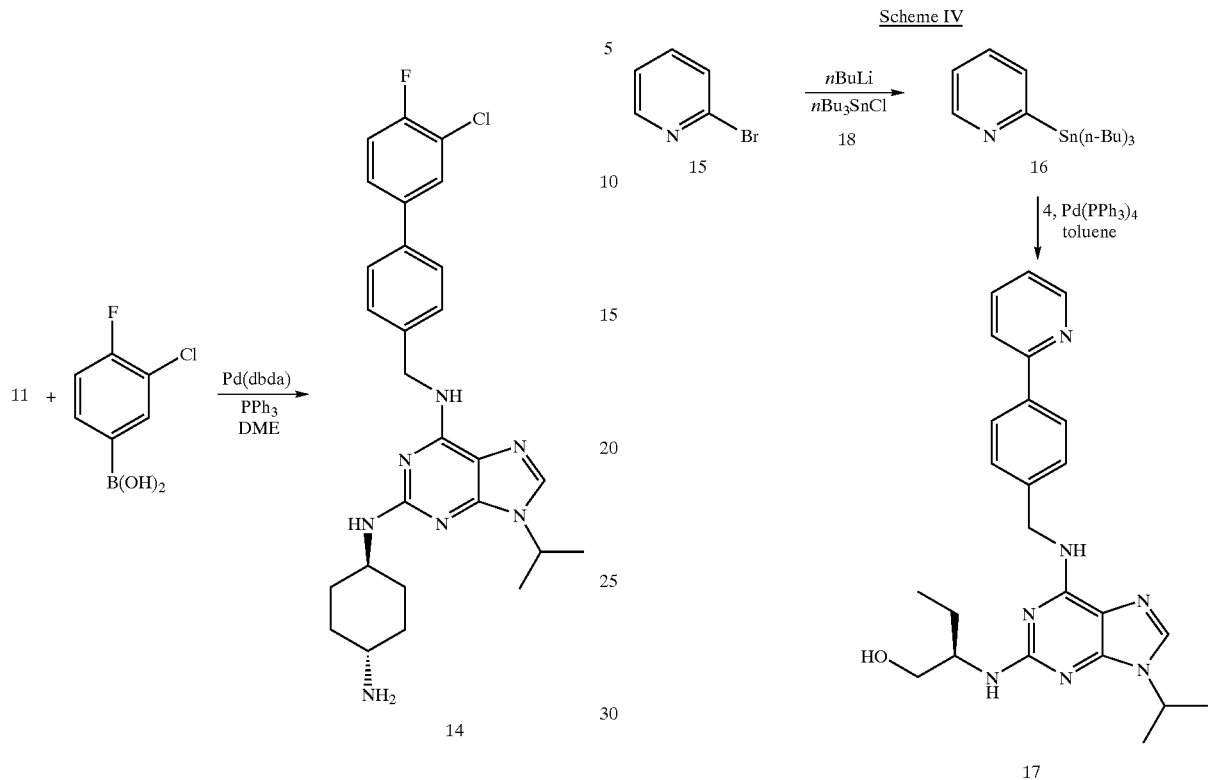
The synthesis of compound 17 is shown below in Scheme V.
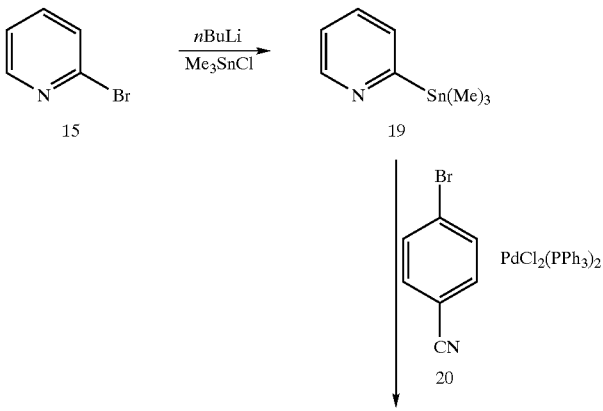

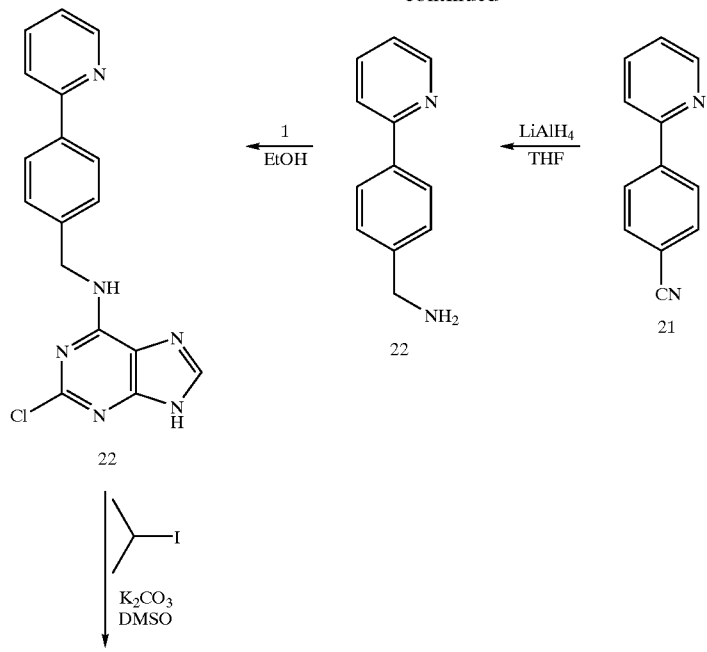
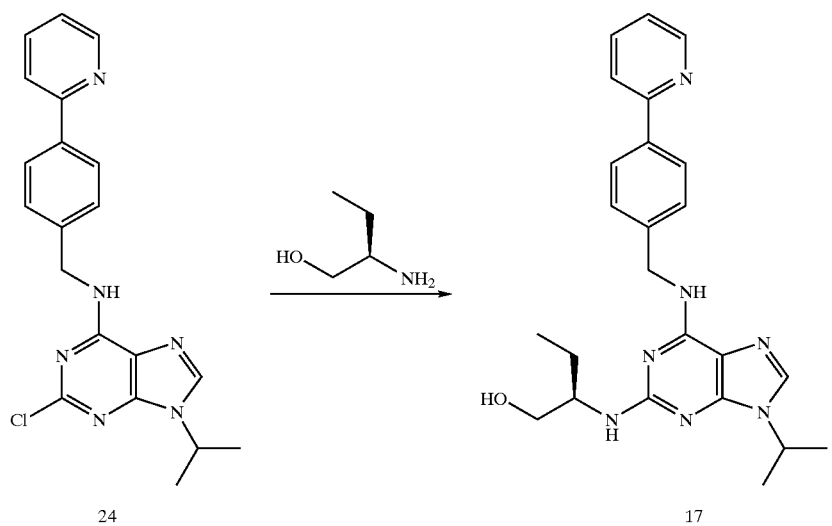
The synthesis of compound 25 is shown below in Scheme VI.
Scheme VI
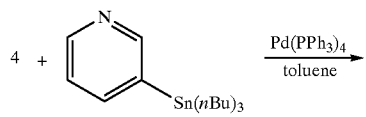

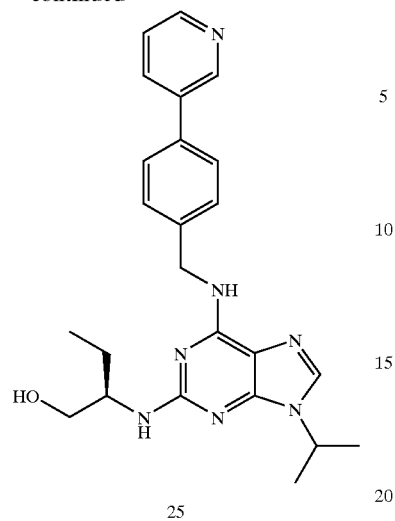
25
The alternative synthesis of compound 25 is shown below in Scheme VII.
Scheme VII
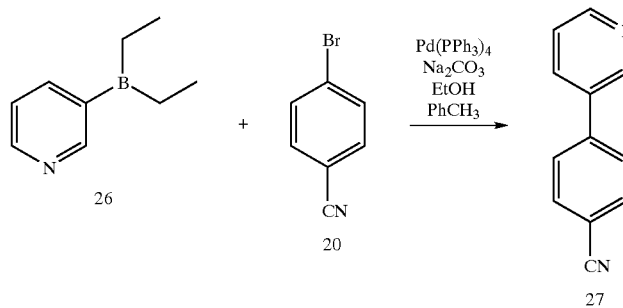
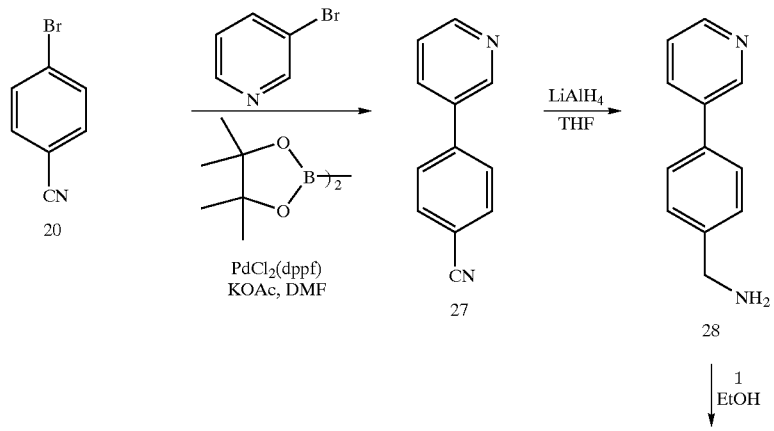

-continued
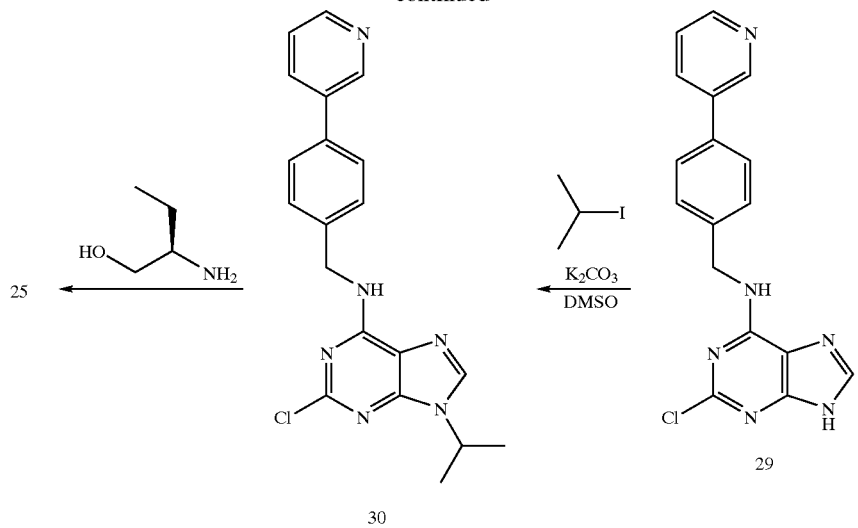
The synthesis of compound 32 is shown below in Scheme VIII.
The syntheses of compounds 33 and 34 are shown below in Scheme IX.
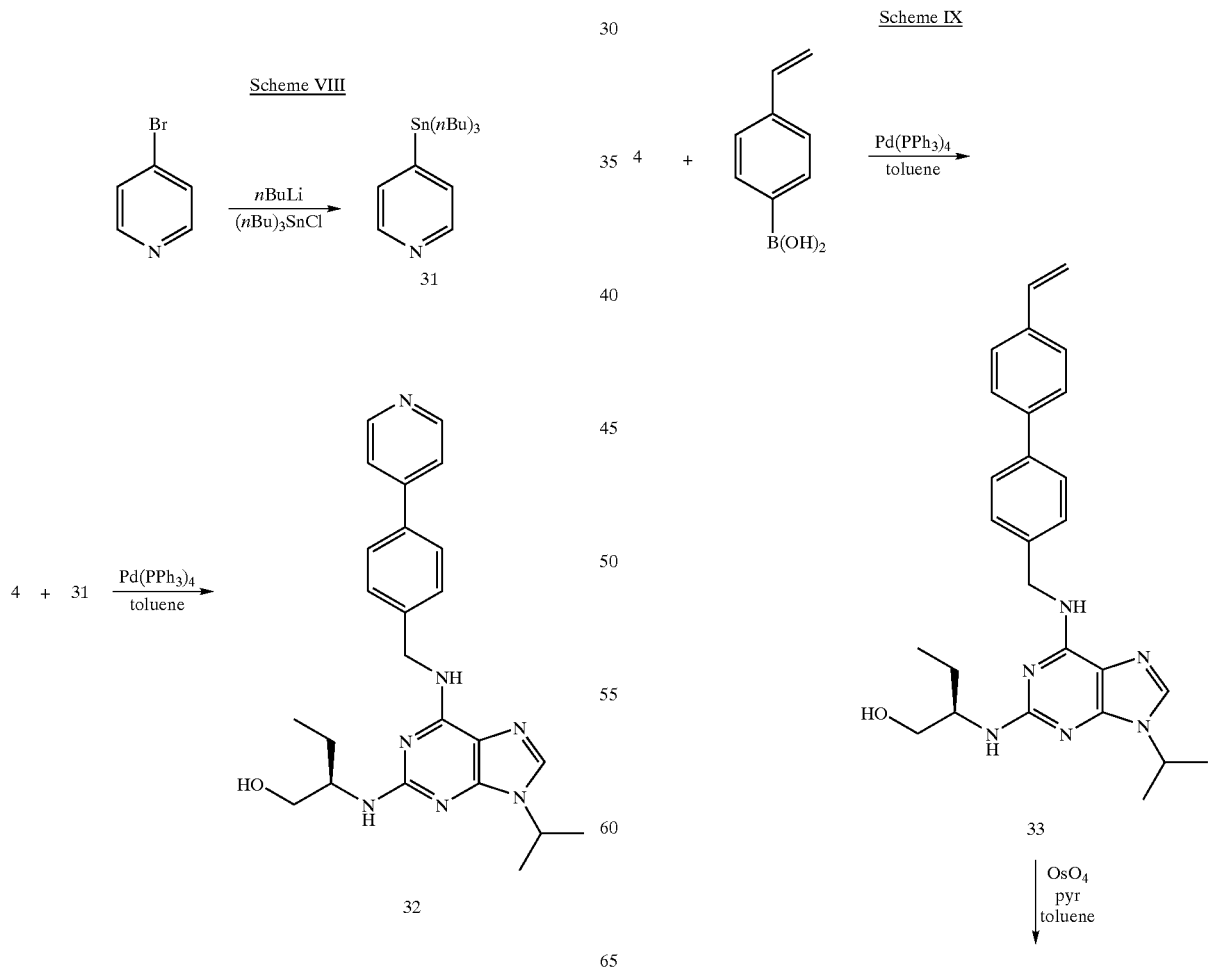

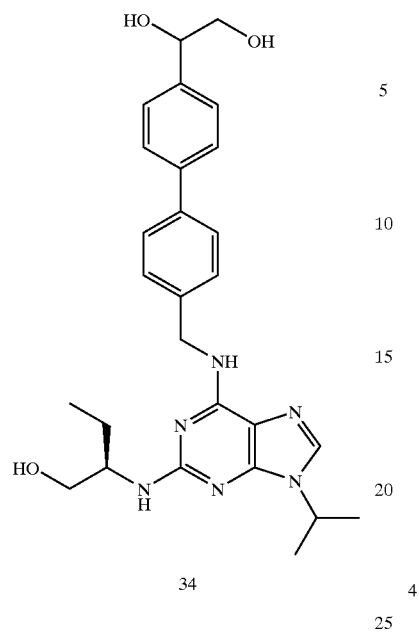
The syntheses of compounds 36, 38, and 40 are shown below in Scheme X.
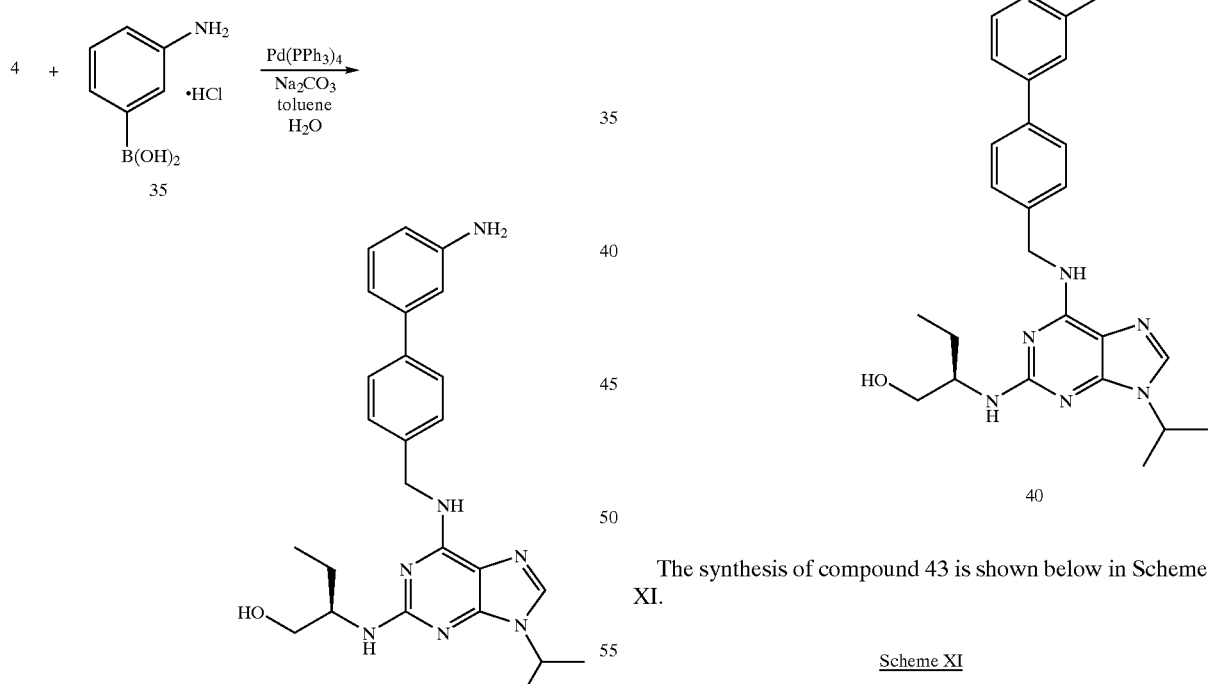
Scheme X
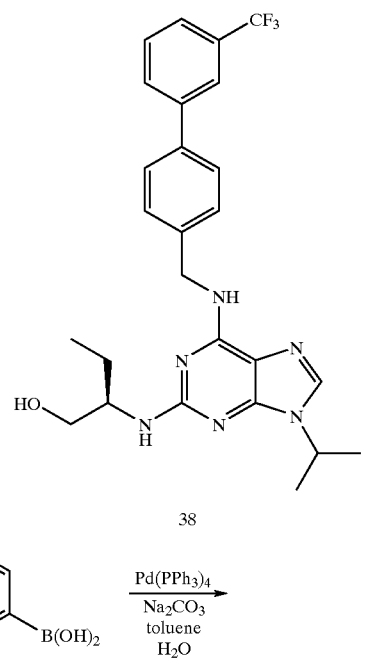
The synthesis of compound 43 is shown below in Scheme XI.
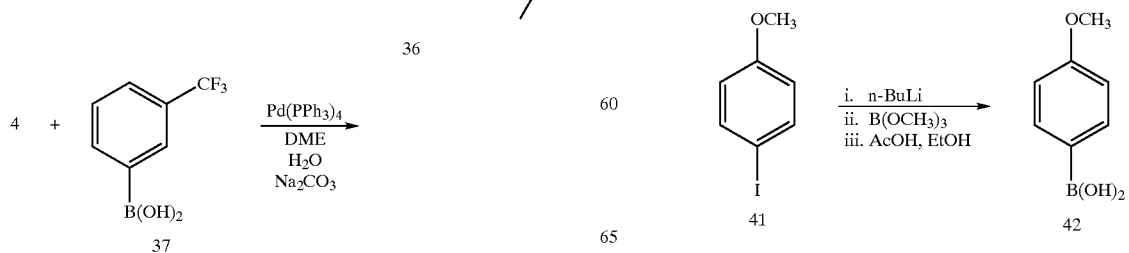
Scheme XI 4 + 42 →[Pd(PPh3)4, Na2CO3, toluene, H2O]
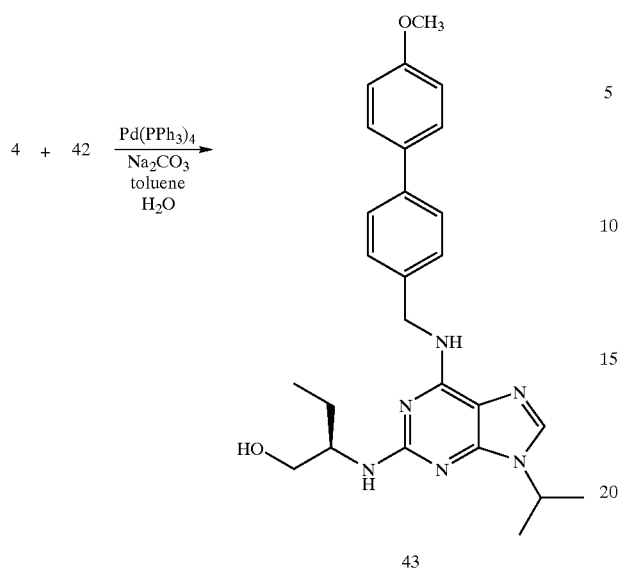
43
The synthesis of compound 46 is shown below in Scheme XII.
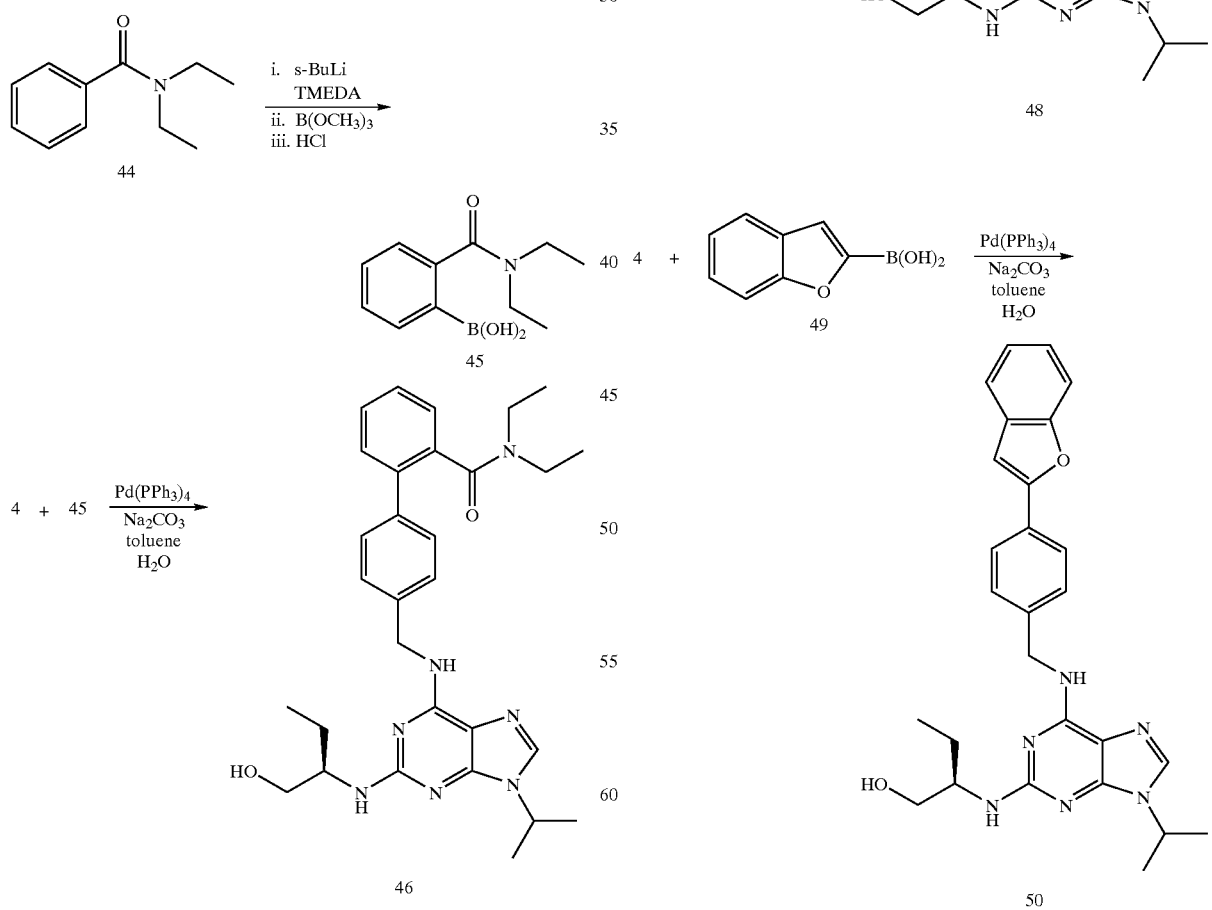
The syntheses of compound 48 and 50 are shown below in Scheme XIII.
Scheme XIII
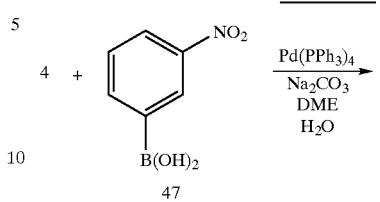

The synthesis of compound 53 is shown below in Scheme XIV.
The synthesis of compound 54 is shown below in Scheme XV.
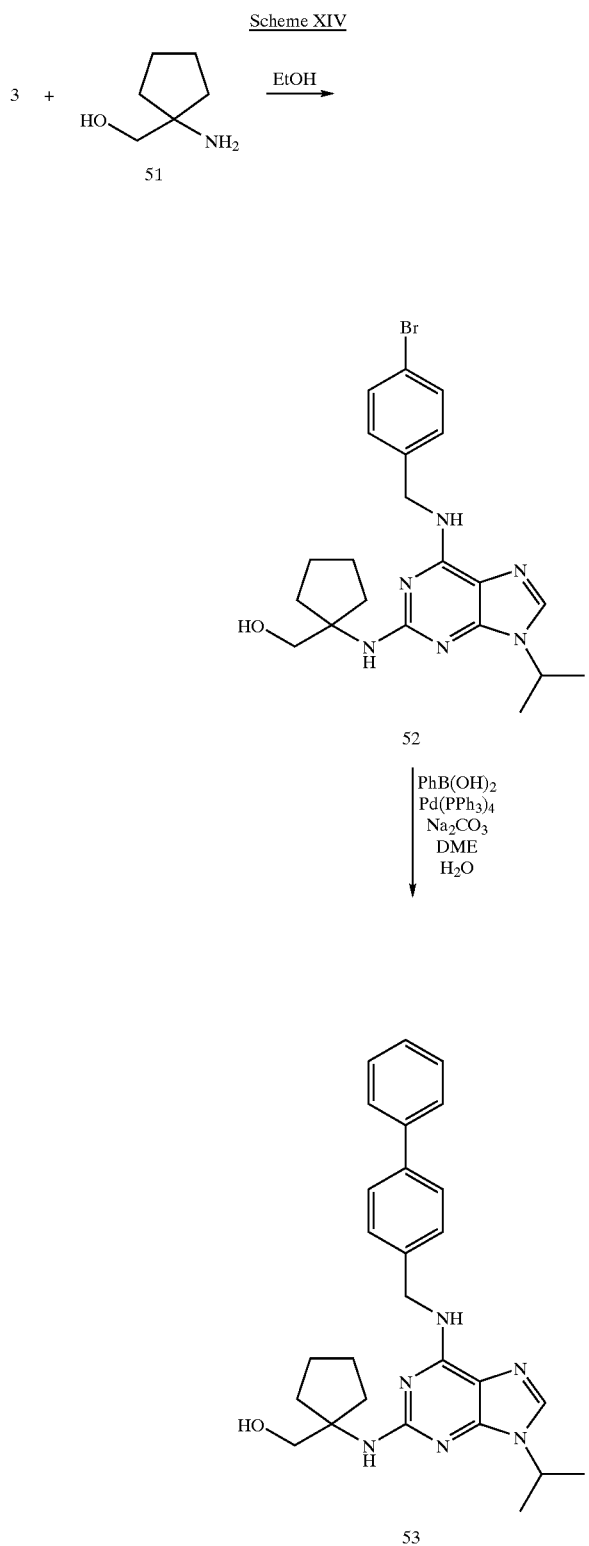
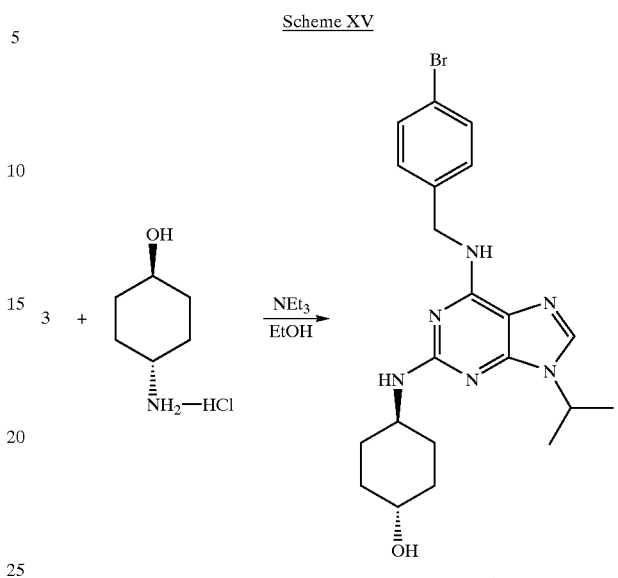
The synthesis of compound 56 is shown below in Scheme XVI.
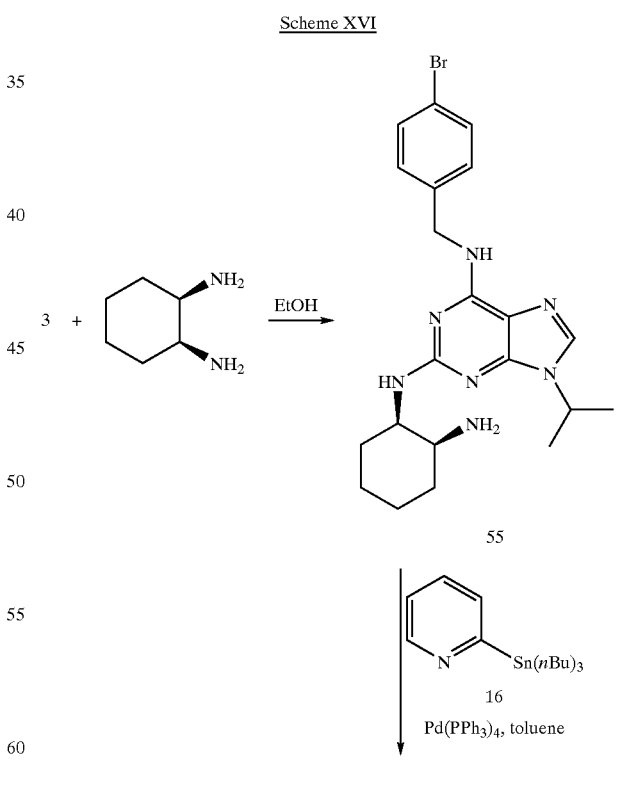

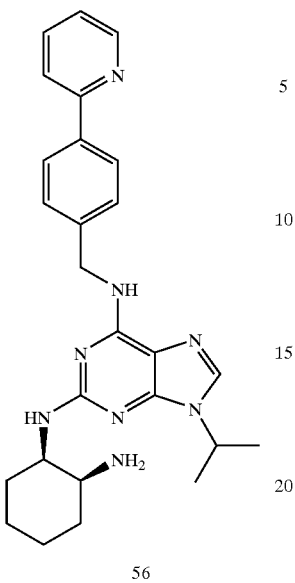
56
The synthesis of compound 58 is shown below in Scheme XVII.
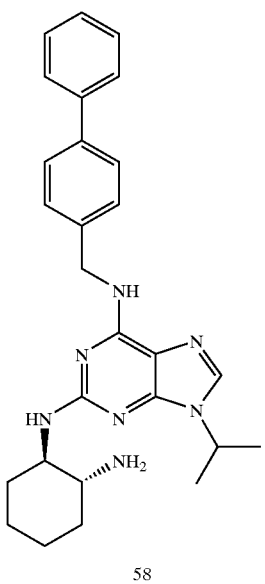
58
The synthesis of compound 60 is shown below in Scheme XVIII.
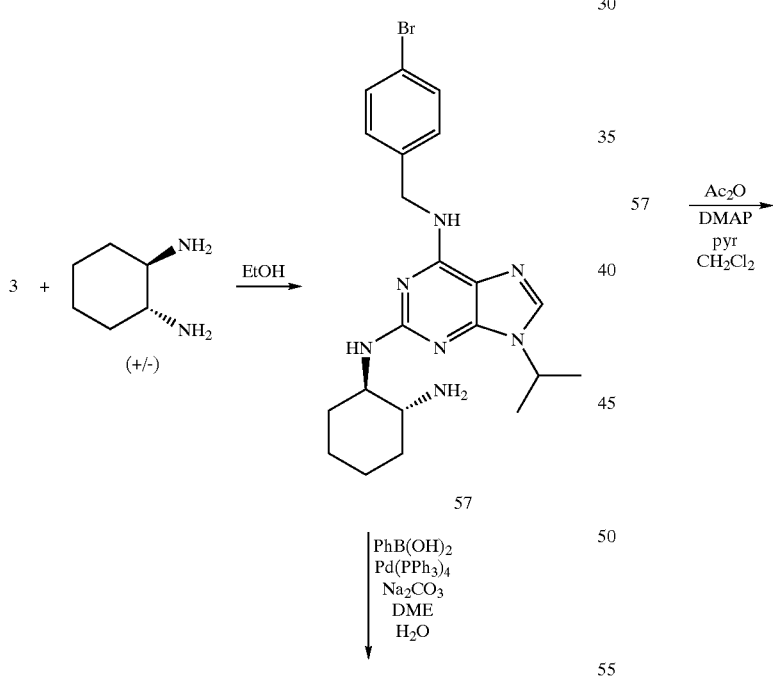
Scheme XVII
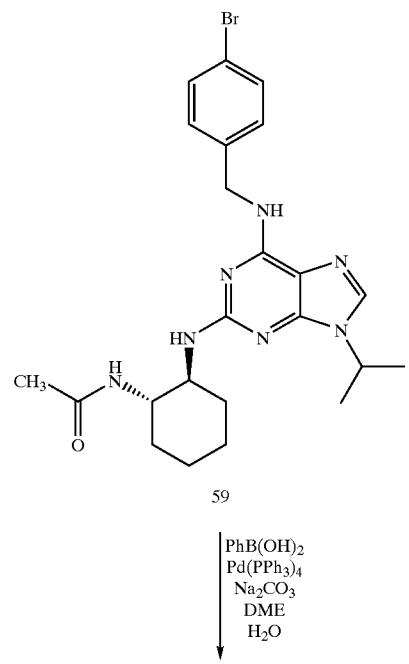
Scheme XVIII

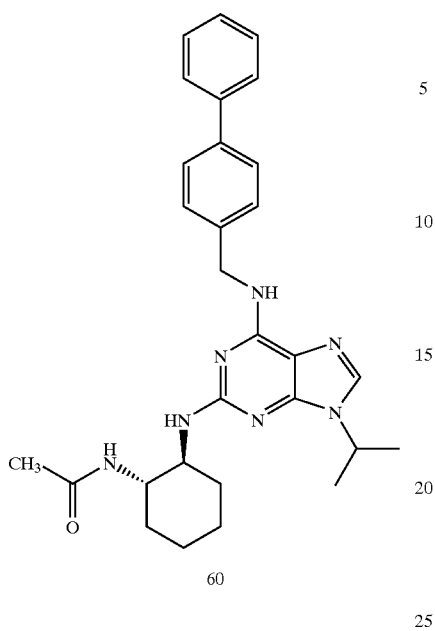
60
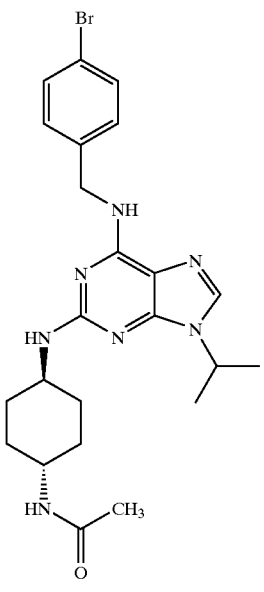
62
The syntheses of compounds 61, and 62 are shown below in Scheme XIX.
Scheme XIX
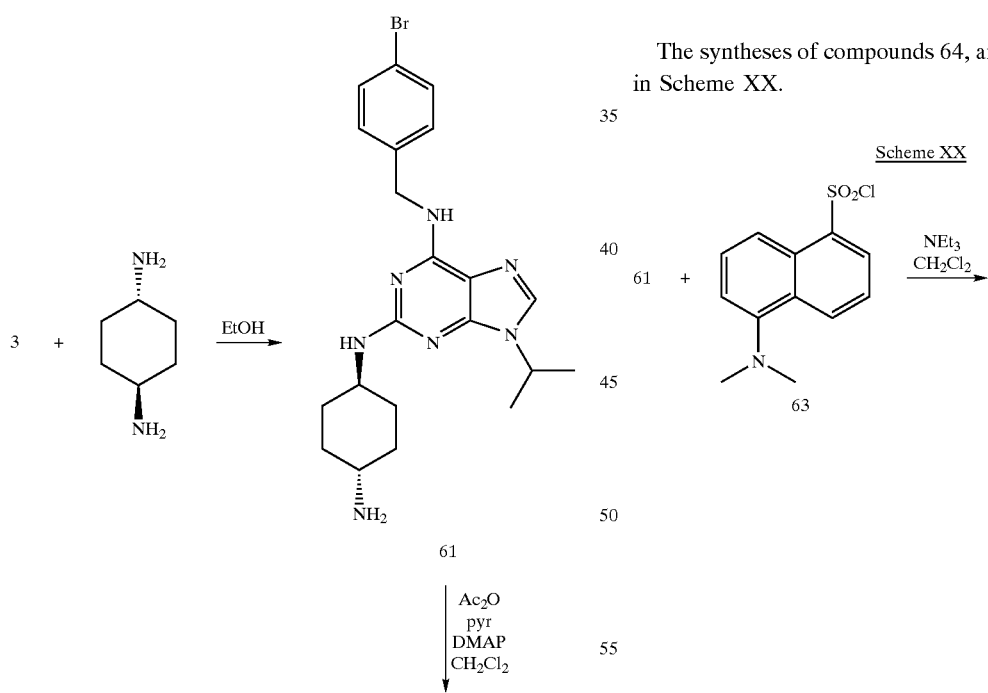
The syntheses of compounds 64, and 65 are shown below in Scheme XX.
Scheme XX
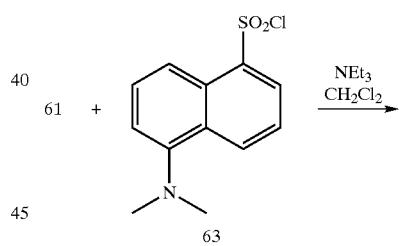

The syntheses of compounds 66, and 67 are shown below in Scheme XXI.
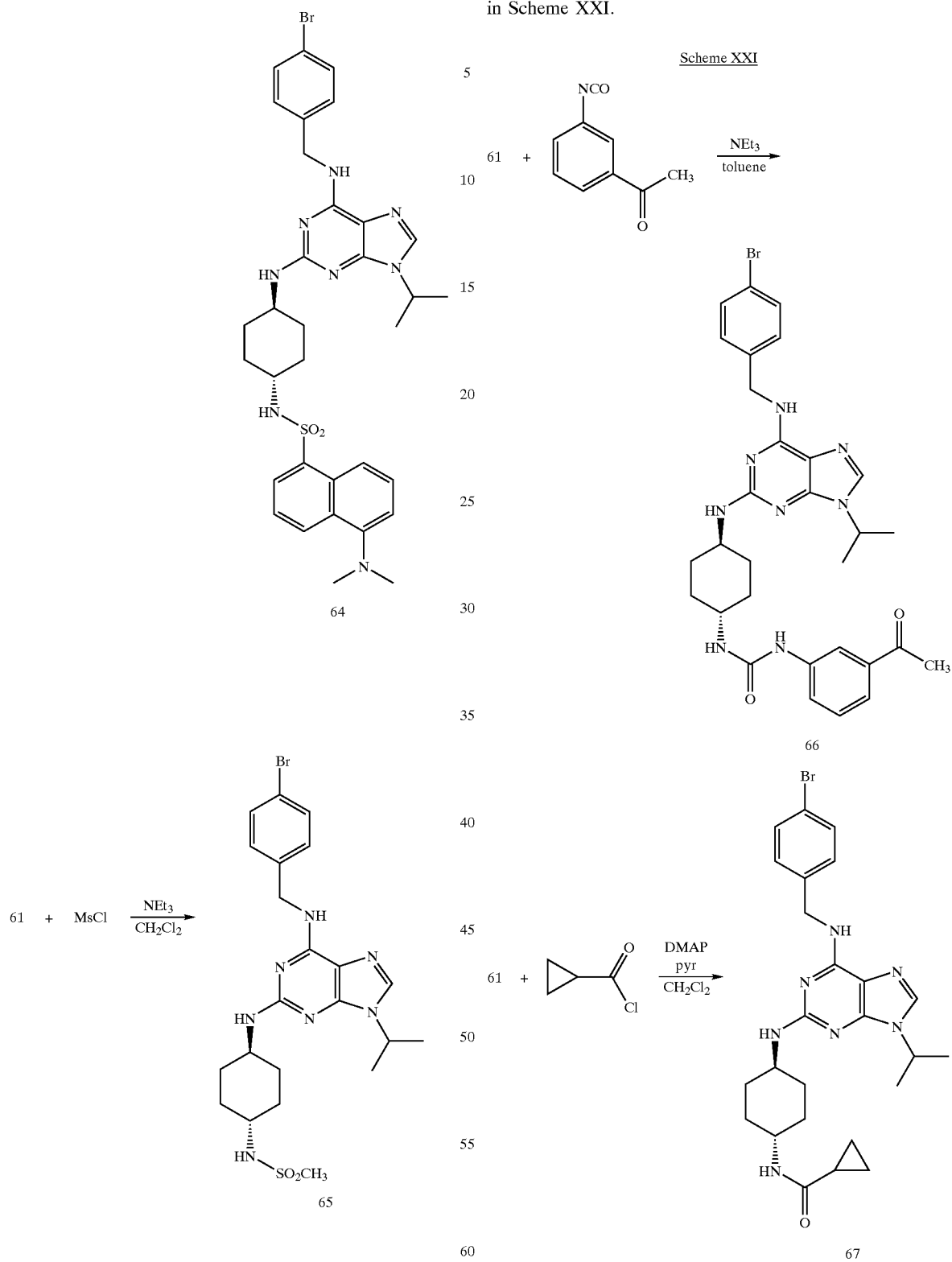

The synthesis of compound 73 is shown below in Scheme XXII.
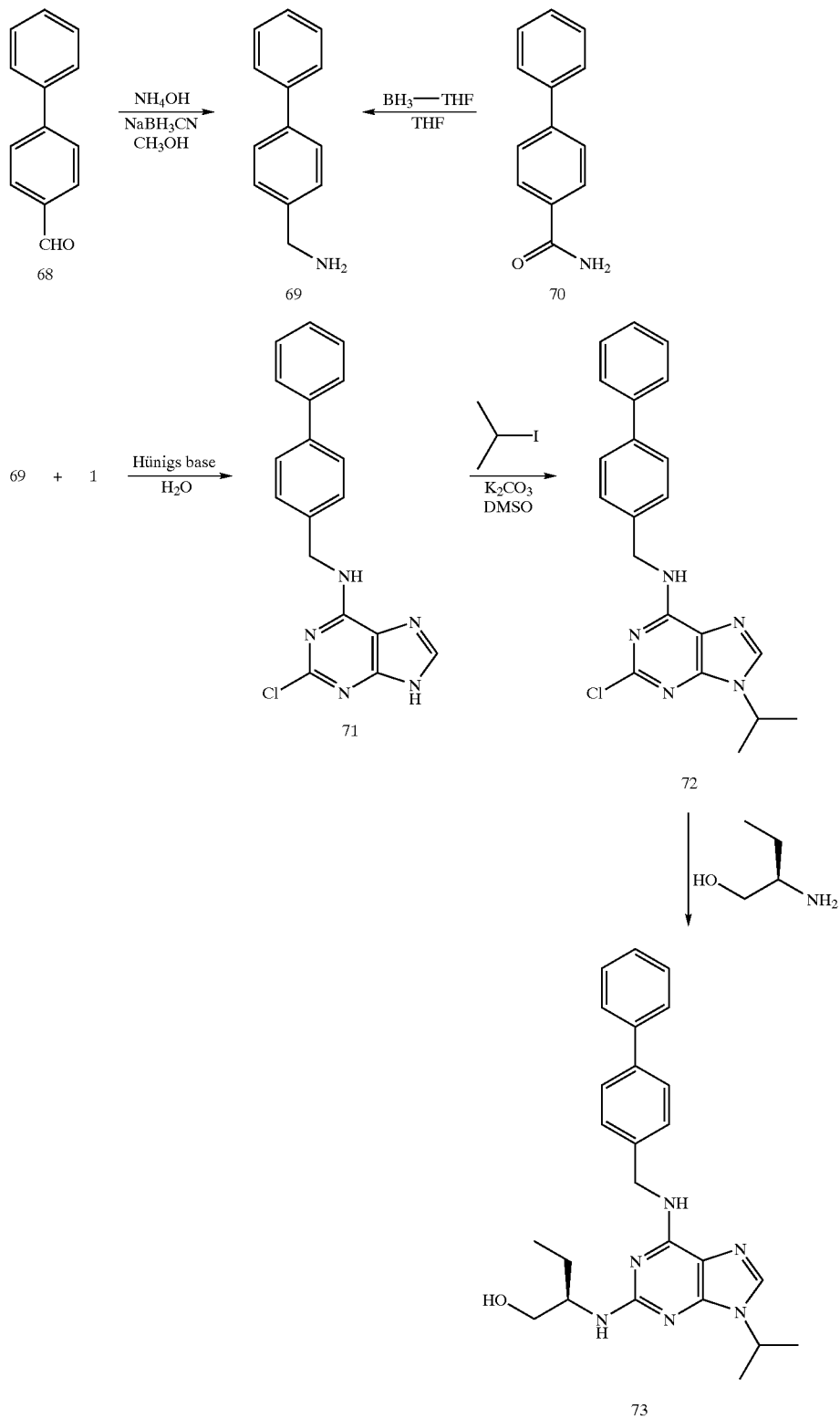

The syntheses of compounds 74, 75, and 76 are shown below in Scheme XXIII.
Scheme XXIII
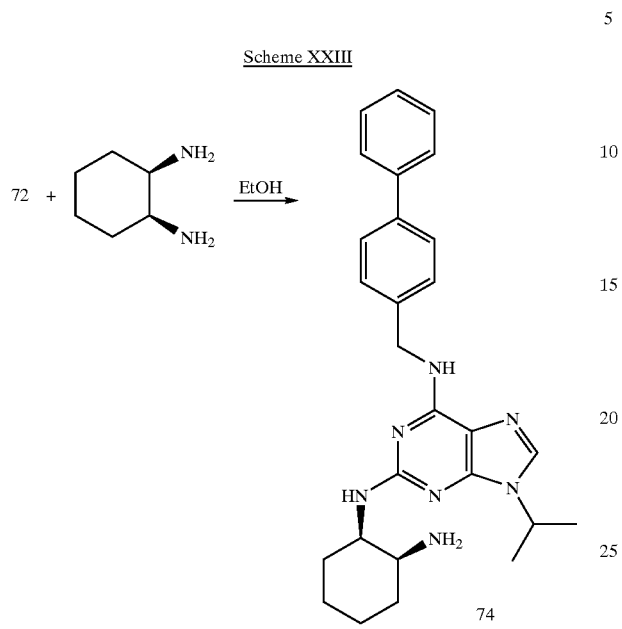
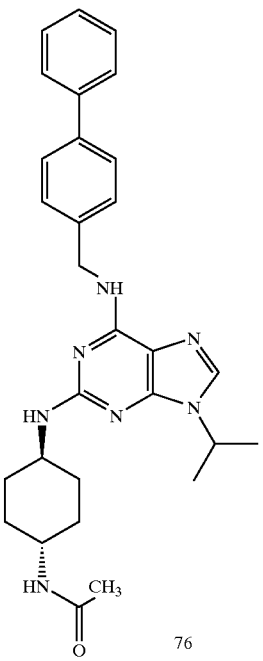
The synthesis of compound 77 is shown below in Scheme XXIV.
Scheme XXIV
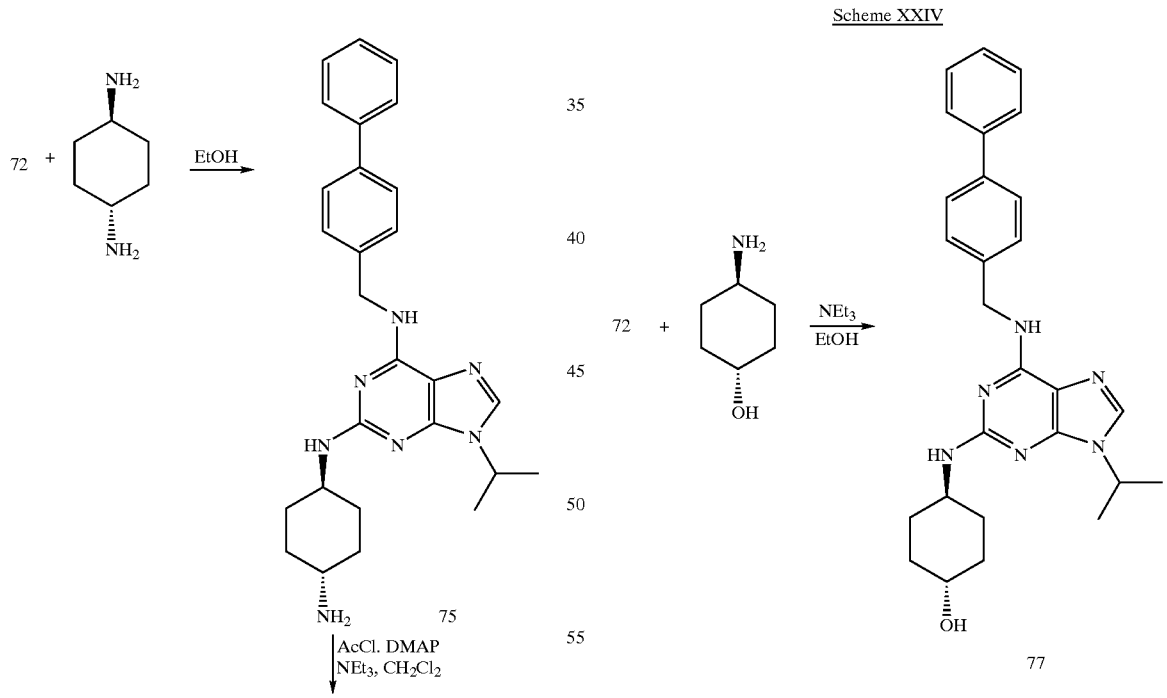

The synthesis of compound 78 is shown below in Scheme XXV.
Scheme XXV
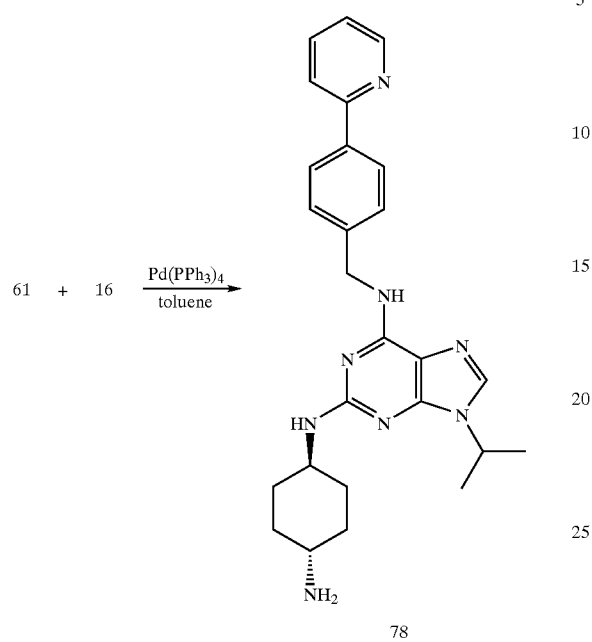
78
An alternative synthesis of compound 78, and the synthesis of compound 79 are shown below in Scheme XXVI.
Scheme XXVI
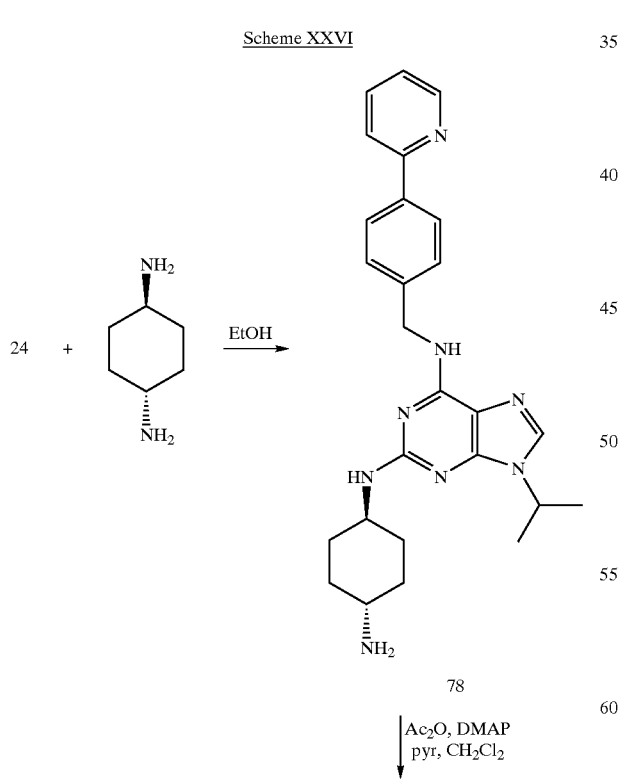
78
| Ac₂O, DMAP
pyr, CH₂Cl₂
-continued
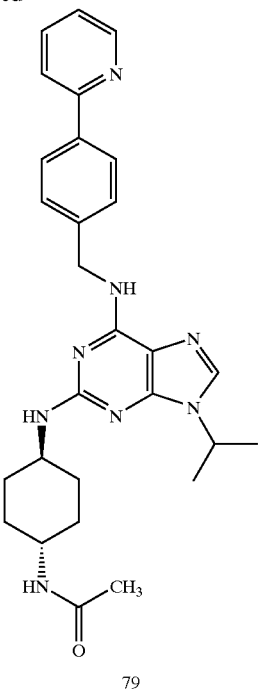
79
The synthesis of compound 80 is shown below in Scheme XXVII.
Scheme XXVII
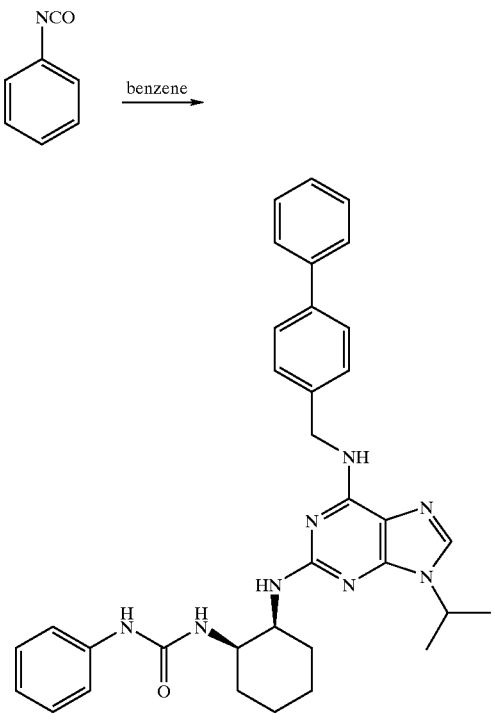
80 in Scheme XXVIII.
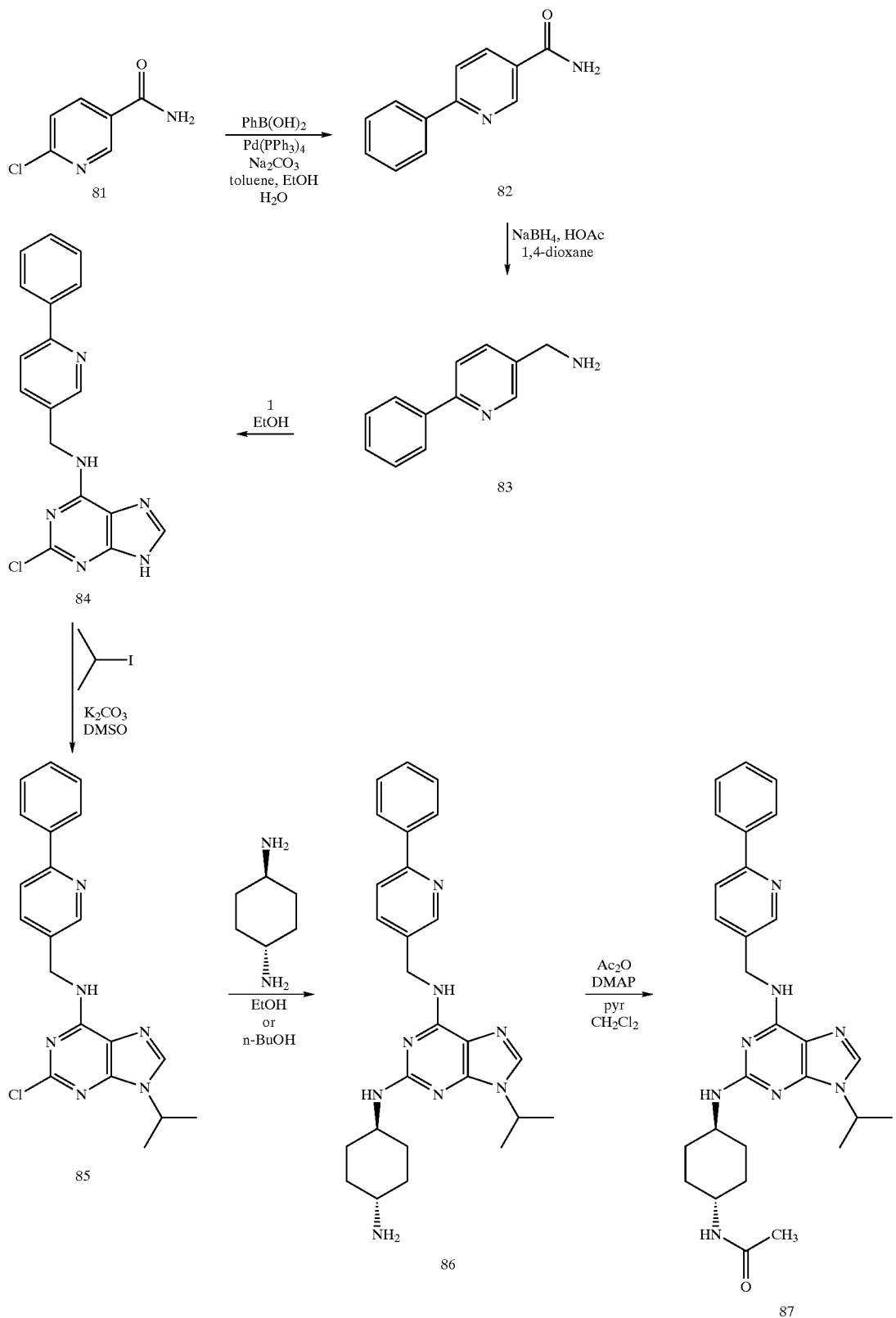
Scheme XXVIII

The synthesis of compound 88 is shown below in Scheme XXIX.
Scheme XXIX
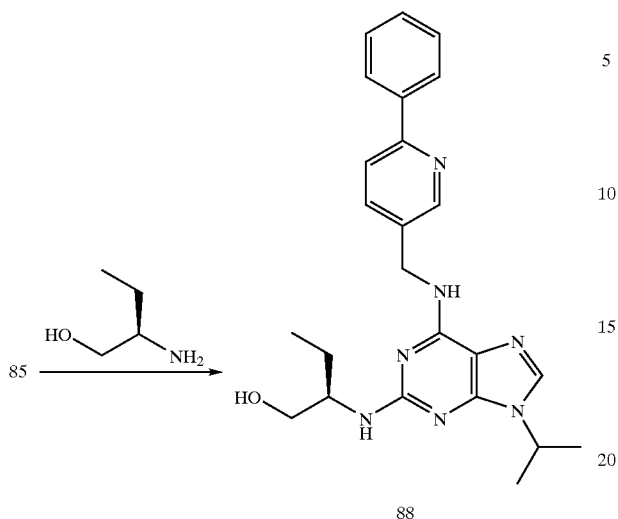
The syntheses of compounds 93, and 94 are shown below in Scheme XXX.
Scheme XXX
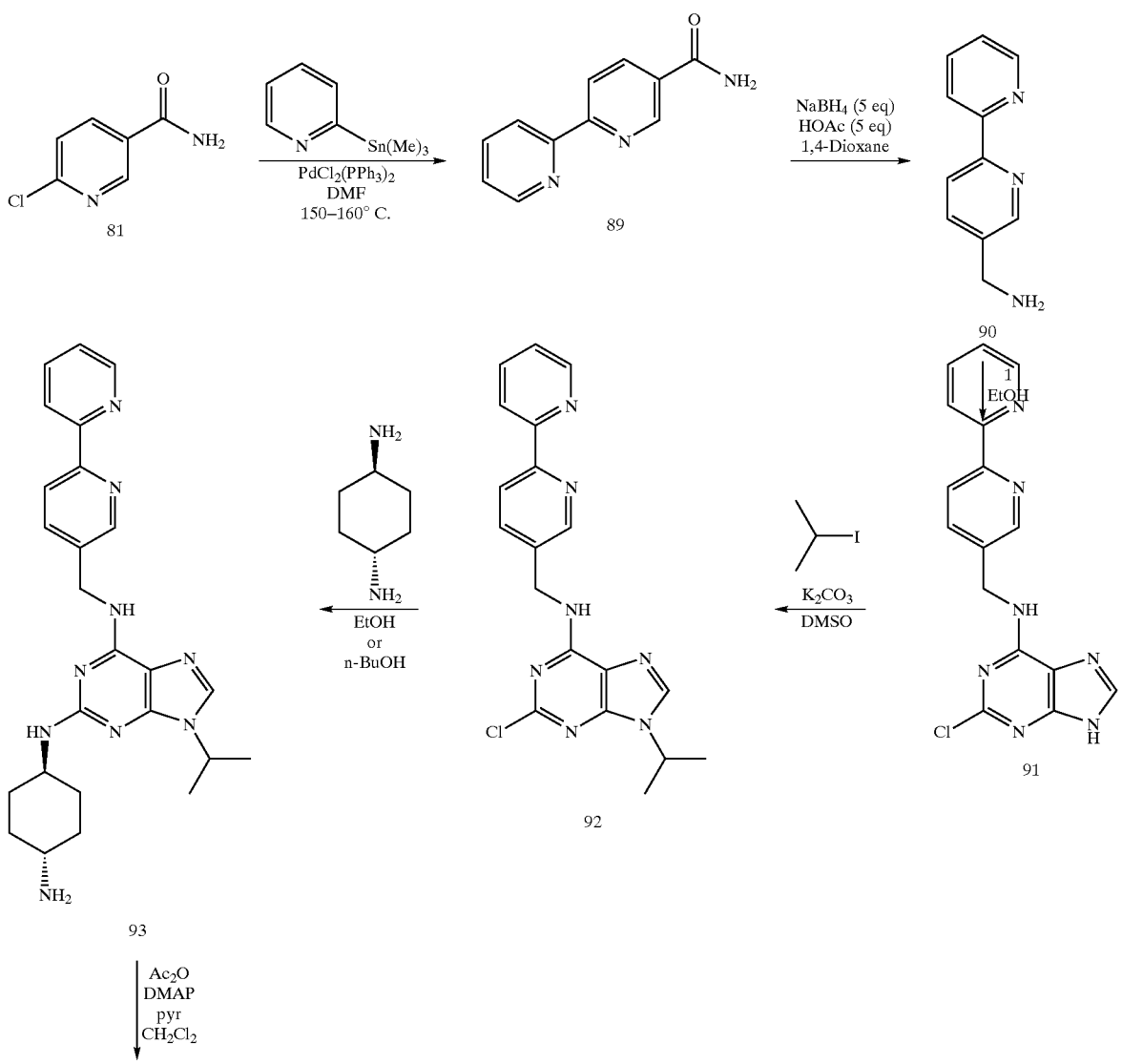

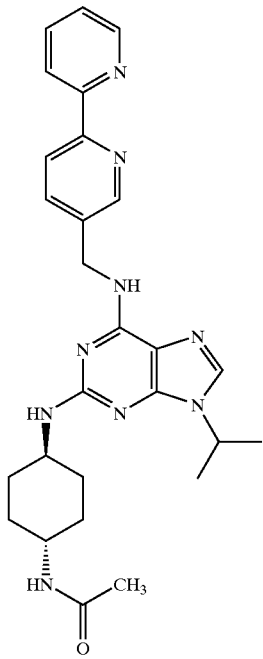
The syntheses of compounds 95, and 96 are shown below in Scheme XXXI.
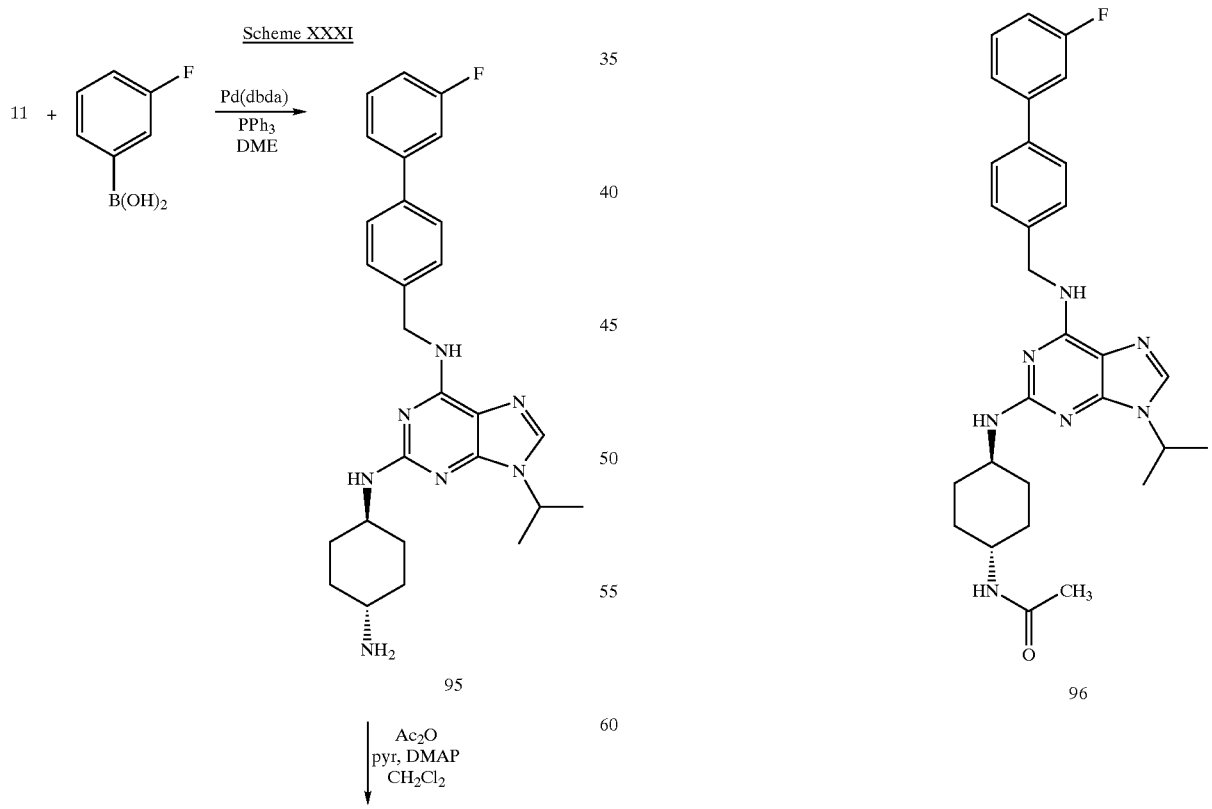

The synthesis of compound 97 is shown below in Scheme XXXII.
Scheme XXXII
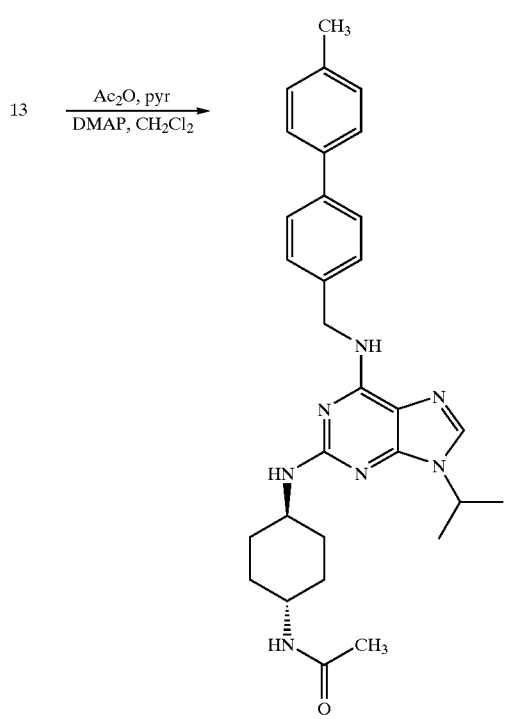
97
The syntheses of compounds 98, and 99 are shown below in Scheme XXXIII.
Scheme XXXIII
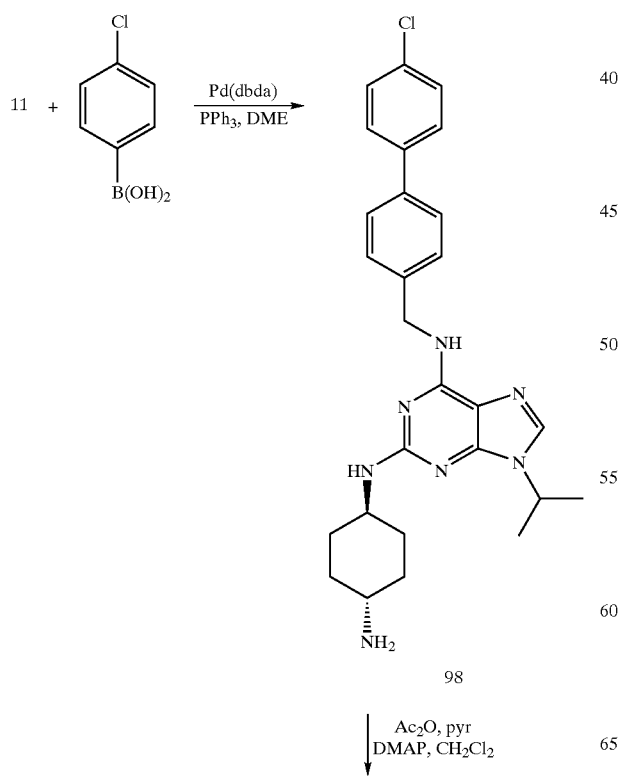
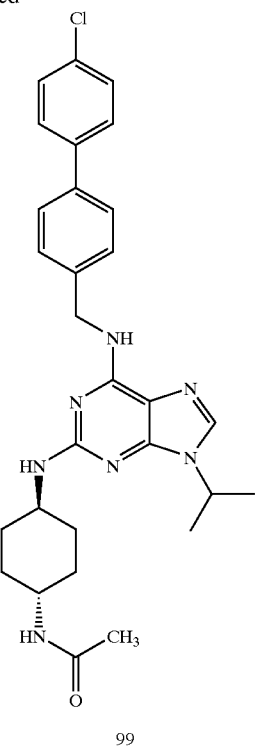
99
The synthesis of compound 100 is shown below in Scheme XXXIV.
Scheme XXXIV
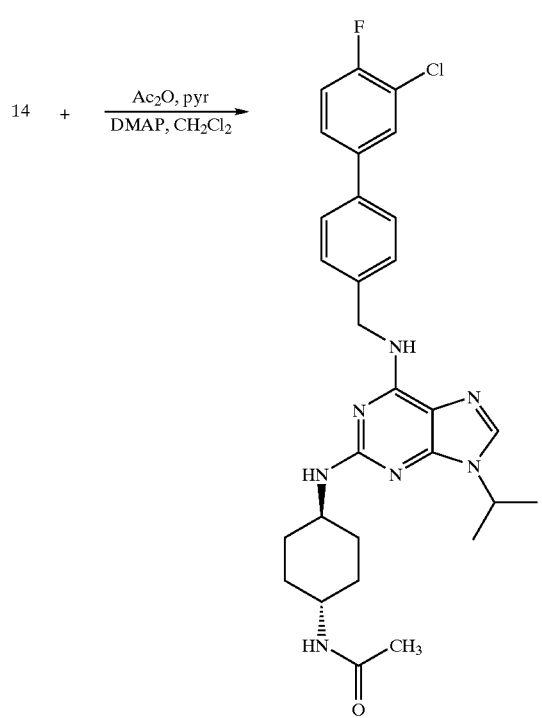
100

The syntheses of compounds 101, and 102 are shown below in Scheme XXXV.
The syntheses of compounds 103, and 104 are shown below in Scheme XXXVI.
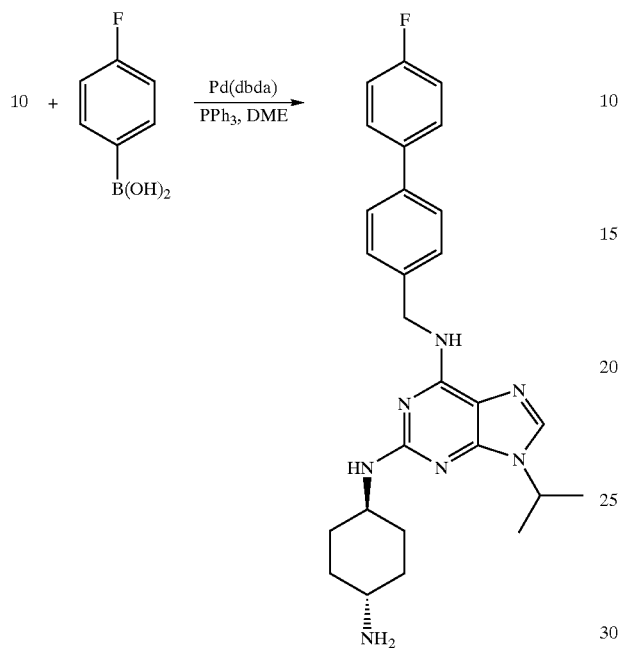
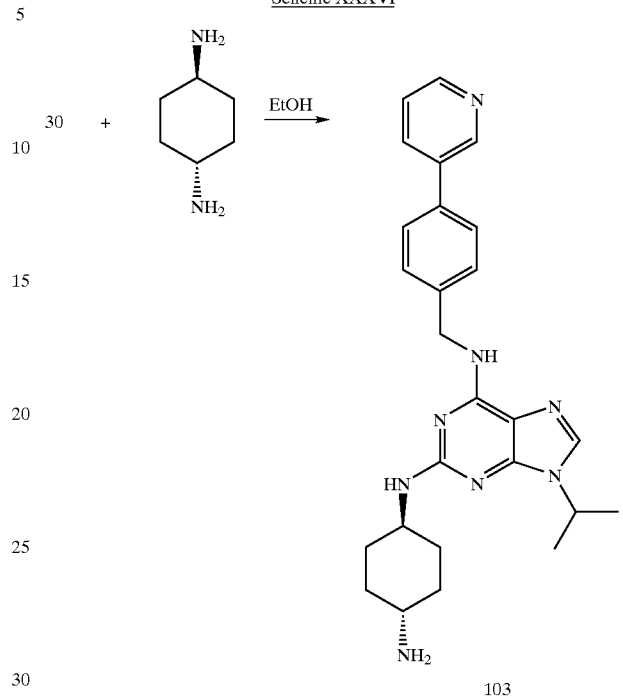
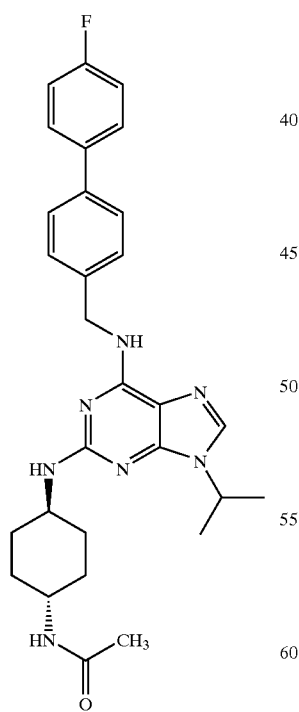
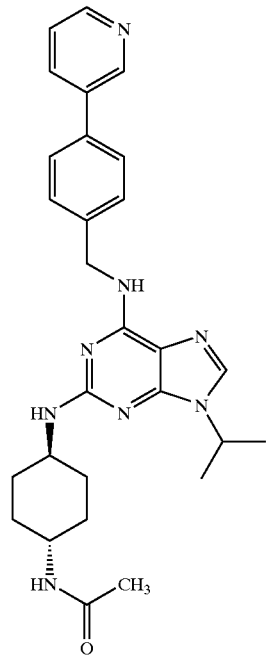

The syntheses of compounds 106, 107, and 108 are shown below in Scheme XXXVII.
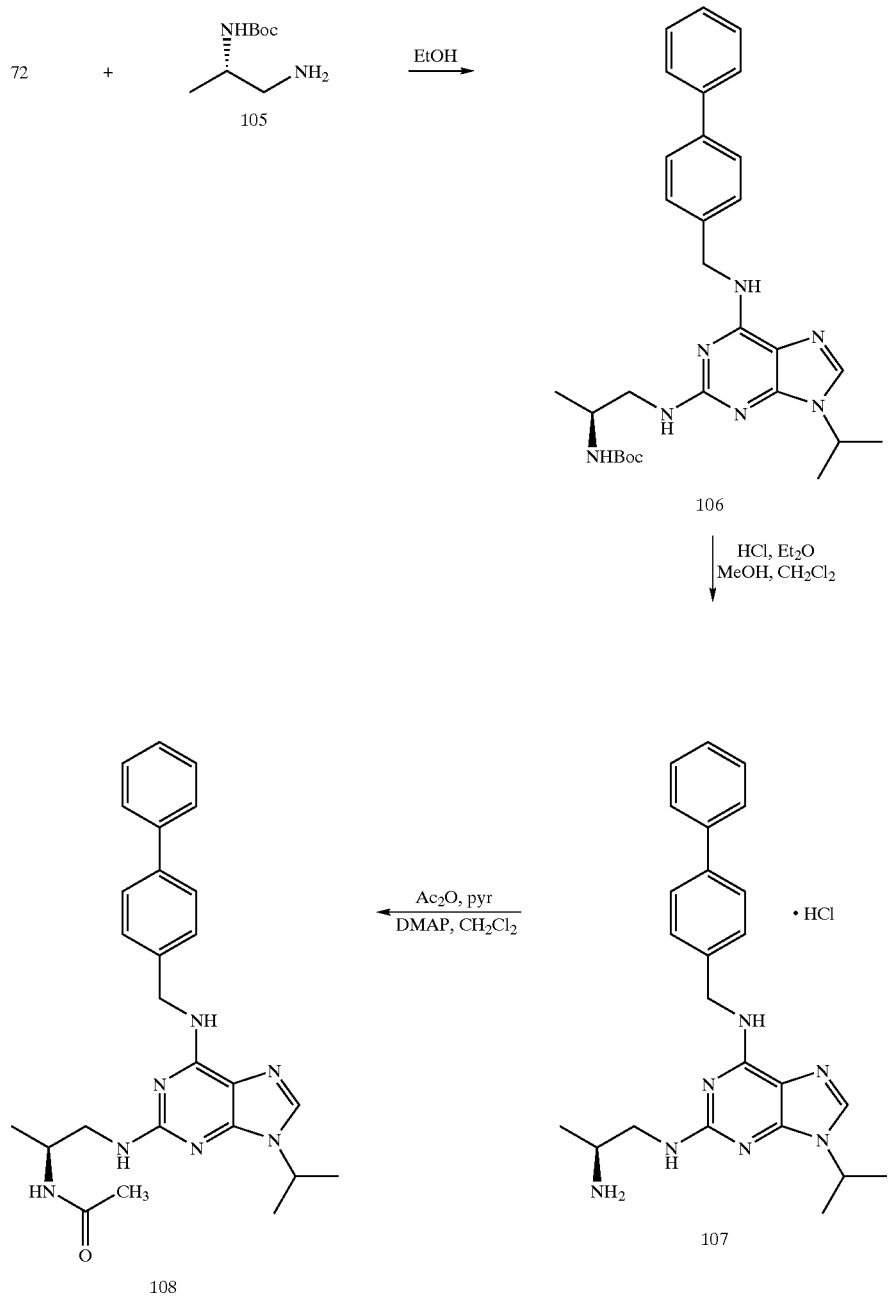

The syntheses of compounds 109, and 110 are shown below in Scheme XXXVIII.
The syntheses of compounds 111, and 112 are shown below in Scheme XXXIX.
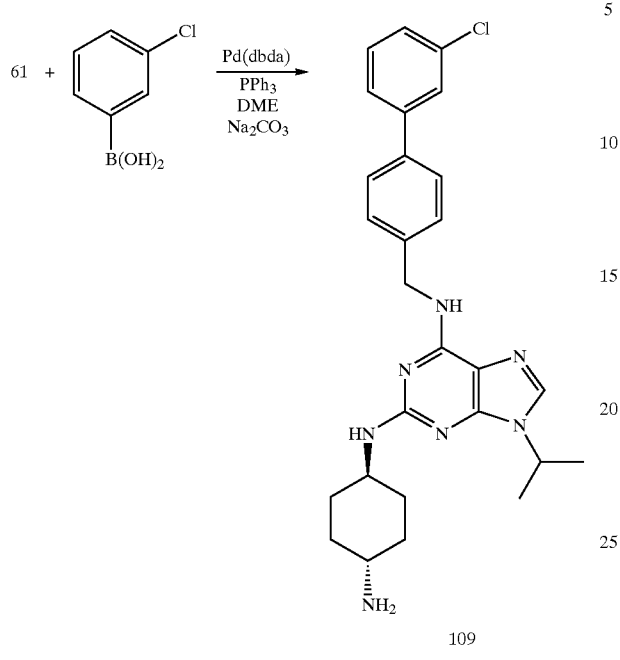
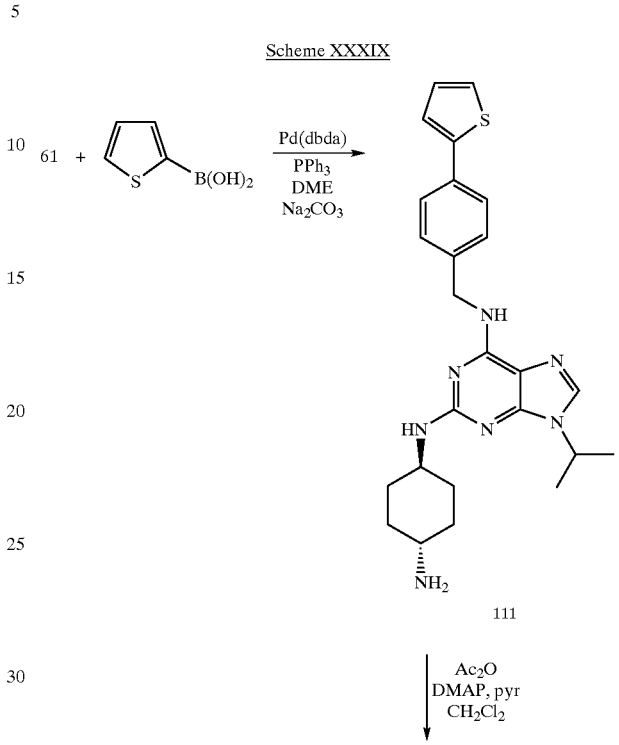

The synthesis of compound 113 is shown below in Scheme XL.
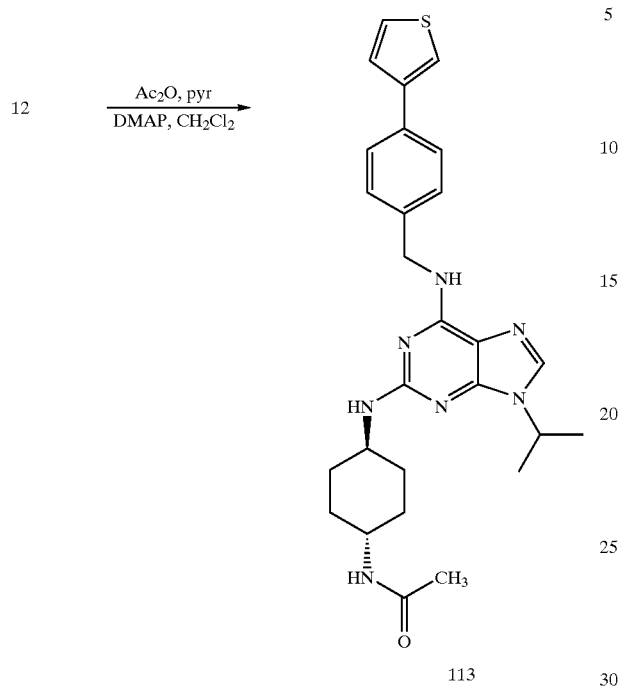
The syntheses of compounds 114, 115, 116, and 117 are shown below in Scheme XLI.
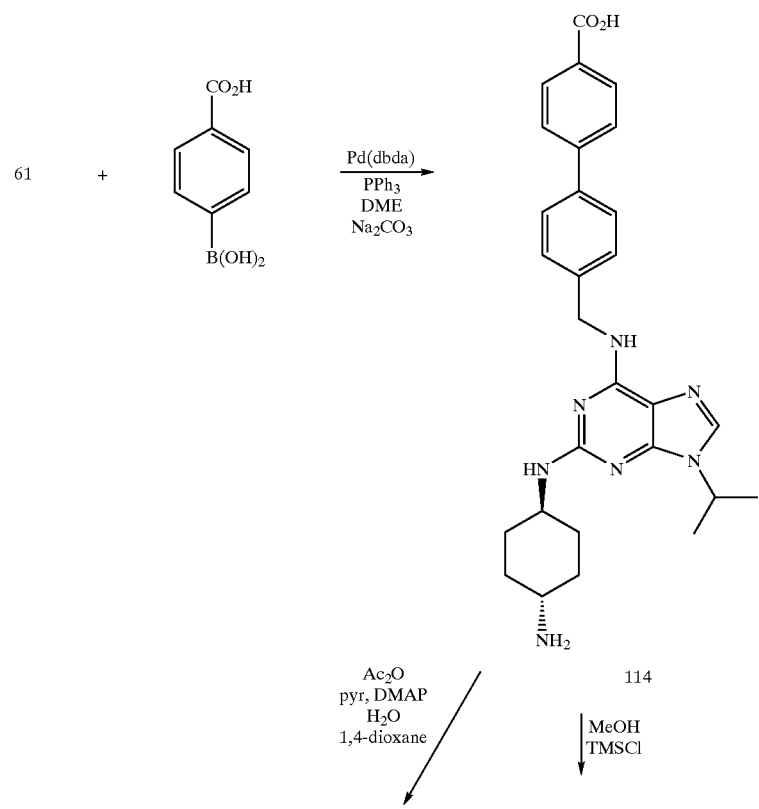

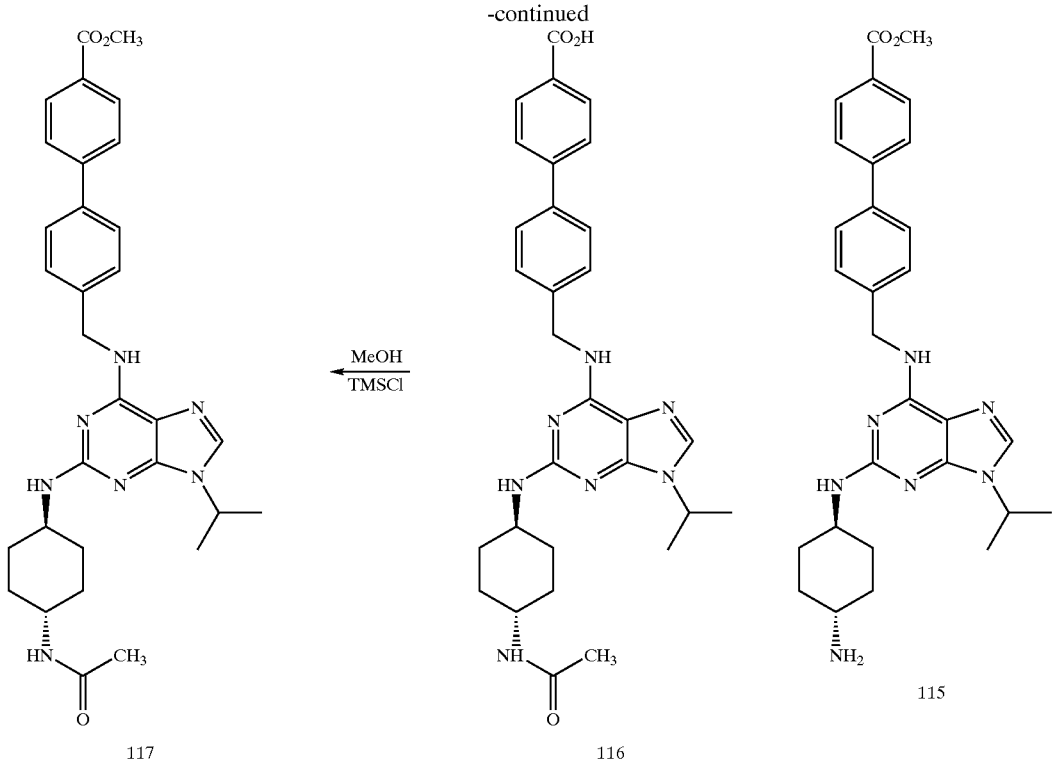
The synthesis of compound 118 is shown below in Scheme XLII.
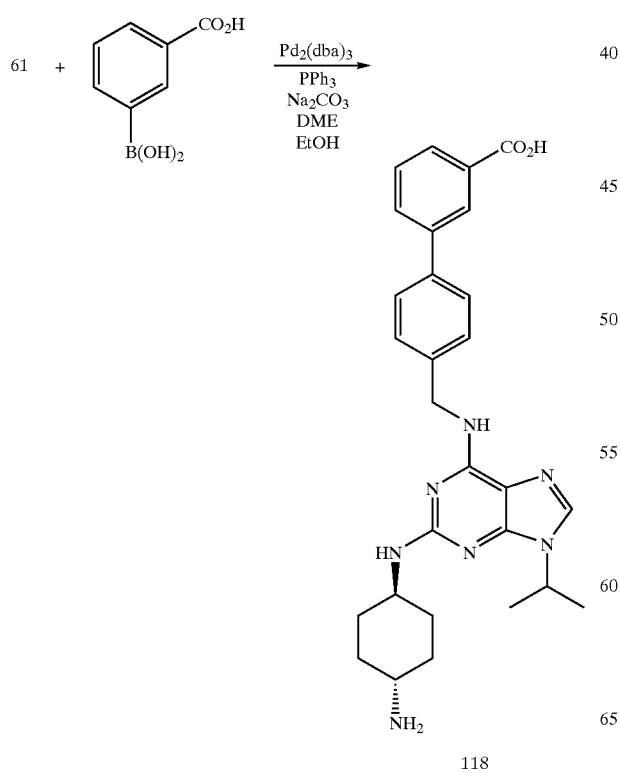

The syntheses of compounds 123 and 124 are shown below in Scheme XLIII.
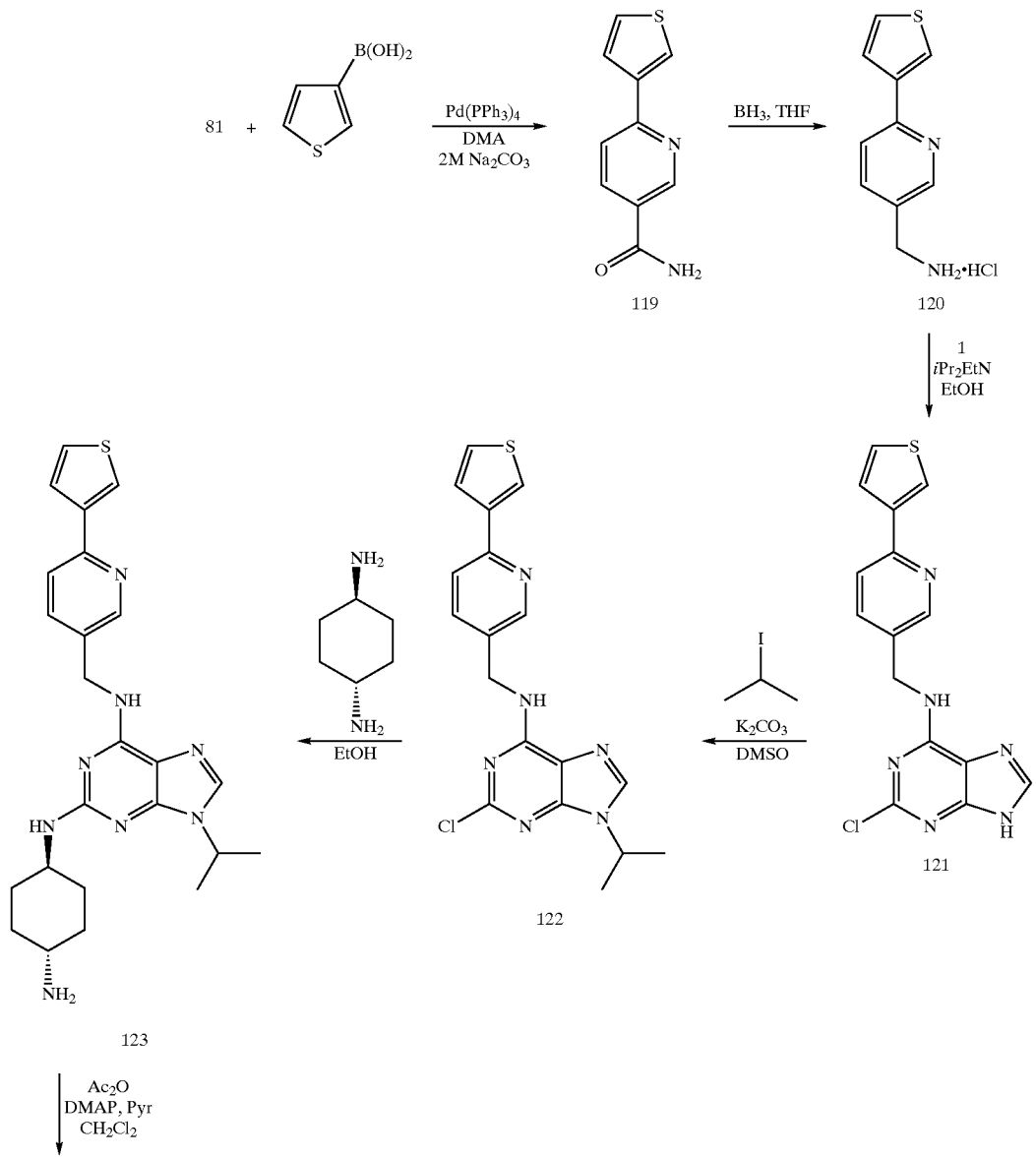

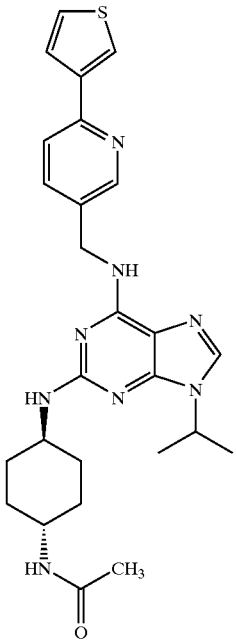

124

EXAMPLES

Proton NMR spectra were obtained on a Bruker AC 300 spectrometer at 300 MHz or a Bruker 500 MHz spectrometer and were referenced to tetramethylsilane as an internal standard. The IR spectrometer used was a single beam Perkin-Elmer Spectrum 1000 FT-IR. All IR spectra obtained were prepared in a pressed disc of KBr. All IR spectra obtained were acquired with a total of 4 accumulations at a resolution of 4.00 cm$^{-1}$. Melting points were obtained on a Mel-Temp II apparatus and are uncorrected. Mass spectra were obtained on either a Shimadzu QP-5000 or a PE Sciex API 150 Mass Spectrometer.

Example 1

Preparation of Compound 2

To the starting material 1 (1.0 g, 5.29 mmol) was added 4-bromobenzylamine (2.53 g, 11.4 mmol), and EtOH (11 mL). The mixture was stirred and heated at 50° C. in a round-bottomed flask and then H$_2$O (1 mL) and EtOH (10 mL) were added to dissolve the solids. The mixture was refluxed for 1 h. Hünig's base (3.68 mL, 21.2 mmol) was added and refluxed overnight, during which time a precipitate formed. The solution was filtered to provide a light yellow solid. The solid was dried in vacuo (1.08 g, 60%): $^1$H NMR (300 MHz, DMSO-d$_6$) δ8.75 (bs, 1H), 8.15 (s, 1H), 7.52 (d, 2H), 7.30 (d, 2H), 4.63 (bs, 2H); CI MS m/z=340 [C$_{12}$H$_9$BrClN$_5$+H]$^+$.

Example 2

Preparation of Compound 3

To the starting material 2 (1.08 g, 3.19 mmol) was added DMSO (11 mL), K$_2$CO$_3$ (2.20 g, 15.95 mmol), and 2-iodopropane (1 mL, 9.57 mmol). The solution was stirred overnight then poured into H$_2$O (75 mL) and stirred. Additional H$_2$O (25–50 mL) was added to the mixture to form a yellow solid. The stirring was continued at 0° C. The solid was filtered in vacuo. The crude product was purified by silica gel chromatography to provide 3 (0.66 g, 50%) as a white solid: mp 136–140° C; $^1$H NMR (300 MHz, CDCl$_3$) δ7.78 (s, 1H), 7.49 (d, 2H), 7.28 (d, 2H), 6.12 (bs, 1H), 4.90–4.70 (m, 3H), 1.61 (d, 6H).

Example 3

Preparation of Compound 4

To starting material 3 (1.44 g, 3.78 mmol) was added 2-amino-1-butanol (5.06 g, 56.7 mmol) and ethanol (5 mL) and the mixture was heated in a sealed tube in an oil bath at 150–160° C. for 48 h. The cooled solution was transferred to a round-bottomed flask and the ethanol was removed in vacuo. The crude product was purified by flash column chromatography on silica gel to give 4 (0.90 g, 55%): $^1$H NMR (300 MHz, CDCl$_3$) δ7.44–7.41 (m, 3H), 7.23 (d, 2H), 6.22 (s, 1H), 5.06 (s, 1H), 4.90 (d, 1H), 4.78–4.68 (m, 2H), 4.65–4.55 (m, 1H), 3.91–3.80 (m, 2H), 3.66–3.60 (m, 1H), 1.66–1.47 (m, 8H), 1.04–0.99 (t, 3H).

Example 4

Preparation of Compound 5

To starting material 4 (0.13 g, 0.29 mmol) was added 3-acetamidophenylboronic acid (0.21 g, 1.19 mmol) and Pd(Ph$_3$)$_4$ (0.08 g, 0.07 mmol), Na$_2$CO$_3$ (2M, 0.60 mL), and toluene (5 mL). The solution was degassed with argon for 10 min then heated at 130° C. for 6 h. The cooled solution was diluted with water and then extracted with CH$_2$Cl$_2$ (3×50 mL). The combined organic phases were washed with brine, dried over anhydrous Na$_2$SO$_4$, filtered, and concentrated to yield a viscous orange oil. The oil was purified by flash column chromatography on silica gel and then the product crystallized upon standing to give 5 (0.06 g, 41%) as a pale yellow solid: $^1$H NMR (300 MHz, CDCl$_3$) δ8.01–7.21 (m, 9H), 6.48 (s, 1H), 4.97 (d, 1H), 4.82–4.70 (m, 2H), 4.65–4.53 (m, 1H), 3.98–3.25 (m, 2H), 3.20–3.05 (m, 1H), 2.20 (s, 3H), 1.69–1.45 (m, 8H), 1.07–0.98 (t, 3H).

Example 5

Preparation of Compound 7

To 4-iodobenzoic acid (52.2 g, 0.21 mol) was added CH$_2$Cl$_2$ (500 mL) and DMF (2 drops) at room temperature.

Oxalyl chloride (32 g, 0.25 mol) was added dropwise in 0.5 h and stirred for 2 d. The volatiles were removed in vacuo to a volume of 150 mL to give the acid chloride and $CH_2Cl_2$. To a mixture of ice (500 mL) and $NH_4OH$ (29%; 100 mL) was added the $CH_2Cl_2$ solution during 15 min. The resulting solids were collected, washed with $CH_2Cl_2$, and dried in vacuo. The solids were slurried in $H_2O$ for 1 h. The solids were collected by filtration. washed in water and acetone, and dried in vacuo to give 7 (48 g; 92%): mp 213–216° C.

Example 6

Preparation of Compound 8

To a suspension of 7 (11 g, 45 mmol) in THF (50 mL) was added $BH_3$-THF (1M, 22.5 mL, 22.5 mmol). The resulting solution was heated under reflux overnight. The reaction was cooled in an ice bath and MeOH-HCl (60 mL) was slowly added dropwise. The resulting precipitate was filtered and dried to give 8 (10.8 g, 88%) as a white solid: mp 256–262° C. dec.; $^1$H NMR (300 MHz, DMSO-$d_6$) δ8.55 (bs, 3H), 7.79 (d, 2H), 7.32 (d, 2H), 3.98 (s, 2H).

Example 7

Preparation of Compound 9

To compound 1 (7.63 g, 40.4 mmol) was added compound 8 (10.8 g, 40.4 mmol), water (123 mL), and Hüing's base (14 mL, 81 mmol). The mixture was heated to reflux for 5 h and stirred overnight at room temperature to give a pale yellow solution. An additional quantity of water (150 mL) was added, refluxed for 3 h, then cooled overnight. A pale yellow solid was formed which was filtered, washed with water, rinsed with EtOH (2×), and dried in vacuo to give yield 9 (13.3 g, 80%): $^1$H NMR (300 MHz, DMSO-$d_6$) δ8.68 (bs, 1H), 8.28 (s, 1H), 7.68 (d, 2H), 7.50 (d, 2H), 5.08 (bs, 1H), 4.50 (d, 2H).

Example 8

Preparation of Compound 10

To compound 9 (12.2 g, 31.7 mmol) was added $K_2CO_3$ (35 g, 0.25 mol), 2-iodopropane (13 g, 0.13 mol) and DMSO (210 mL). The reaction mixture was stirred under $N_2$ at room temperature overnight, then poured into $H_2O$ (1.5 L) and stirred for 2 d. The precipitate was collected as an off-white solid and washed with $Et_2O$. The aqueous layer was extracted with EtOAc (2×) and the combined organic phases were washed with brine, dried over $Na_2SO_4$, filtered, and evaporated to give an off-white foam (6.4 g). This off-white foam was combined with the precipitate and washed with $Et_2O$ to give 10 (11.0 g): $^1$H NMR (300 MHz, DMSO-$d_6$) δ8.91 (m, 1H), 8.38 (s, 1H), 7.74 (d, 2H), 7.21 (d, 2H), 5.11 (bs, 1H), 4.68 (m, 1H), 4.60 (d, 2H), 1.48 (d, 6H).

Example 9

Preparation of Compound 11

Compound 10 (1.52 g, 3.55 mmol), trans-1,4-diaminocyclohexane (6.35 g, 55.60 mmol), and EtOH (18 mL) were placed in a sealed tube. The reaction mixture was heated at 120–190° C. for 24 h. The reaction was then allowed to cool to room temperature. The reaction mixture was filtered and the filtrate evaporated. The residue was purified by column chromatography, and dried in vacuo for 16 h to yield 11 (1.60 g, 89%) as a yellow sticky oil: $^1$H NMR (300 MHz, CDCl$_3$) δ7.62 (d, 2H), 7.44 (s, 1H), 7.08 (d, 2H), 6.14 (br, 1H), 4.75–4.63 (m, 2H), 4.63–4.54 (m, 2H), 3.75–3.63 (m, 1H), 2.72–2.57 (m, 2H), 2.18–2.00 (m, 2H), 2.00–1.75 (m, 4H), 1.54 (d, 6H), 1.39–1.00 (m, 3H); API MS m/z=506 [$C_{21}H_{28}IN_7$+H]$^+$.

Example 10

Preparation of Compound 12

To compound 11 (0.133 g, 0.26 mmol) was added DME (2.5 mL) and 3-thiopheneboronic acid (0.12 g, 0.97 mmol) in a round-bottomed flask and equipped with a condenser purged with argon. To this was added DME (3 mL) followed by tris(dibenzylidoneacetone)dipalladium (0.01 g, 0.01 mmol) and PPh$_3$ (0.04 g, 0.15 mmol). $Na_2CO_3$ (2M, 0.6 mL) and DME (1 mL) was added to the reaction mixture and the reaction mixture was allowed to reflux for 18.5 h, then stirred at room temperature under argon for 46 h. The reaction mixture was diluted with $H_2O$ and extracted with $CH_2Cl_2$. The combined organic phases were washed with brine, dried over anhydrous $Na_2SO_4$, filtered, and concentrated in vacuo. The residue was purified by column chromatography to yield 12 (0.050 g, 41%) as a tan solid: $^1$H NMR (300 MHz, CDCl$_3$) δ7.56–7.50 (m, 4H), 7.44–7.35 (m, 3H), 6.02 (br, 1H), 4.78 (d, 2H), 4.69–4.54 (m, 2H), 3.75 (br, 1H), 2.69 (br, 1H), 2.15 (br, 2H), 1.88 (br, 3H), 1.54 (d, 7H), 1.33–0.97 (m, 4H); API MS m/z=462 [$C_{25}H_{31}N_7S$+H]$^+$.

Example 11

Preparation of Compound 13

DME (3 mL), tris(dibenzylidoneacetone)dipalladium (0.01 g, 0.01 mmol), and PPh$_3$ (0.04 g, 0.15 mmol) were placed in a round-bottomed flask fitted with a condenser and maintained under argon. Compound 11 (0.13 g, 0.26 mmol), and 4-methylbenzeneboronic acid (0.13 g, 0.98 mmol) dissolved in $Na_2CO_3$ (2M, 0.6 mL) and DME (1 mL) were added to the reaction mixture. The reaction mixture was refluxed for 19.5 h and stirred at room temperature for 4 h. The reaction mixture was diluted with water and extracted with $CH_2Cl_2$. The combined organic phases were washed with brine, dried over anhydrous $Na_2SO_4$, and evaporated. The crude product was purified by column chromatography and dried in vacuo for 22 h to yield the desired product 13 (54 mg, 44%) as an off-white solid: $^1$H NMR (300 MHz, CDCl$_3$) δ7.56–7.41 (m, 7H), 7.23 (s, 1H), 5.92 (br, 1H), 4.83 (d, 2H), 4.74–4.58 (m, 2H), 3.77 (br, 1H), 2.70 (br, 1H), 2.40 (s, 3H), 2.16 (d, 3H), 1.88 (d, 3H), 1.55 (d, 7H), 1.33–0.97 (m, 4H); API MS m/z=470 [$C_{28}H_{35}N_7$+H]$^+$.

Example 12

Preparation of Compound 14

DME (3 mL), tris(dibenzylideneacetone)dipalladium (0.01 g, 0.01 mmol), and PPh$_3$ (0.04 g, 0.15 mmol) were placed in a round-bottomed flask with a condenser under argon. Compound 11 (0.13 g, 0.25 mmol) and 3-chloro-4-fluoroboronic acid (0.15 g, 0.88 mmol) were dissolved in $Na_2CO_3$ (2M, 0.6 mL) and DME (1 mL) were added to the reaction mixture, refluxed for 19 h then stirred at room temperature for 2 h. The reaction mixture was diluted with water and extracted with $CH_2Cl_2$. The combined organic phases were washed with brine, dried over anhydrous $Na_2SO_4$, and evaporated. The crude product was purified by repeated column chromatography to yield 14 (0.019 g, 15%): $^1$H NMR (300 MHz, CDCl$_3$) δ7.59–7.53 (m, 1H), 7.47–7.35 (m, 4H), 7.26–7.14 (m, 3H), 5.81 (br, 1H), 4.81 (d, 2H), 4.72–4.54 (m, 2H), 3.72 (br, 1H), 2.69 (br, 1H), 2.21–2.03 (m, 3H), 1.94–1.78 (m, 3H), 1.54 (d, 6H), 1.33–1.12 (m, 4 1); API MS m/z=508 [$C_{27}H_{31}ClFN_7$+H]$^+$.

Example 13

Preparation of Compound 16

A solution of 15 (2.5 g, 15.8 mmol) and ether was cooled to −78° C. In a separate flask, n-BuLi (15.8 mmol) was also cooled to −78° C. The solution of 15 was added to the n-BuLi solution via cannula to give a dark red solution. The reaction mixture was stirred for 5 min prior to the rapid addition of (n-Bu)$_3$SnCl (6.2 g, 19 mmol). The resulting bright yellow solution was stirred at −78° C. for 2 h, allowed to warm to room temperature, and stirred for another 10 min. The solution was then diluted with H$_2$O (80 mL) and extracted with ethyl acetate (3×50 ml). The organic extracts were combined, washed with brine, dried over Na$_2$SO$_4$, filtered, and concentrated in vacuo to yield the crude product as a yellow oil. Purification by column chromatography gave the product 16 (4.89 g, 84%) as a pale yellow liquid: $^1$H NMR (300 MHz, CDCl$_3$) δ8.72 (d, 1H), 7.48–7.46 (m, 1H), 7.40–7.38 (m, 1H), 7.11–7.09 (m, 1H), 1.61–1.50 (m, 6H), 1.38–1.26 (m, 6H), 1.14–1.09 (m, 6H), 0.97–0.77 (t, 9H).

Example 14

Preparation of Compound 17

To compound 16 (0.18 g, 0.48 mmol) was added compound 4 (0.14 g, 0.33 mmol), Pd(PPh$_3$)$_4$ (0.05 g, 0.49 mmol), and toluene (10 mL) in a sealed tube under an argon atmosphere. The solution was degassed with argon and heated at 135° C. in an oil bath for 3 h. The solution was cooled to room temperature, diluted with saturated NaHCO$_3$, and extracted with CH$_2$Cl$_2$ (3×30 mL). The organic layer was washed with brine, dried over Na$_2$SO$_4$, and concentrated in vacuo to give a light brown oil. The residue was purified by flash column chromatography using MeOH/CH$_2$Cl$_2$ (10%) to afford 17 as a white solid. The sample was dissolved into hexane/CH$_2$Cl$_2$/MeOH and then precipitated with diethyl ether, filtered, and rinsed several times with ether to provide in 17 (30.3 mg): mp 95–100° C.; $^1$H NMR (300 MHz, CDCl$_3$) δ8.68 (d, 1H), 7.96 (d, 2H), 7.77–7.69 (m, 2H), 7.49–7.45 (m, 3H), 7.24–7.20 (m, 1H), 5.99 (s, 1H), 5.11 (s, 1H), 4.88–4.83 (m, 3H), 4.65–4.56 (m, 1H), 3.91–3.80 (m, 2H), 3.65–3.60 (m, 1H), 1.66–1.52 (m, 8H), 1.05–0.99 (t, 3H), IR (KBr) 3411, 2968, 1601, 1489 cm$^{-1}$; CI MS m/z=432 [C$_{24}$H$_{29}$N$_7$+H]$^+$.

Example 15

Preparation of Compound 19

To a solution of n-BuLi (2.5M hexane solution, 10.9 ml, 27.4 mmol) in ethyl ether 28 mL at −78° C. was added 2-bromopyridine (4.33 g, 27.4 mmol) in ethyl ether (15 mL). After stirring for 30 min, a solution of trimethylstannylchloride (6.0 g, 30 mmol) in THF (10 mL) was added. Stirring was continued at −78° C. for 2 h and the mixture was then warmed up to room temperature and filtered. The precipitate was washed with ether and the combined the ether filtrates were concentrated to give the crude product: $^1$H NMR (500 Hz, CDCl$_3$) δ8.69–8.68 (d, 1H), 7.47–7.07 (m, 3H), 0.30 (s, 9H).

Example 16

Preparation of Compound 21

A mixture of 4-bromobenzonitrile (1.68 g, 9.2 mmol), crude 2-trimethylstannylpyridine (3.33 g, 13.8 mmol), and PdCl$_2$(PPh$_3$)$_2$ (321 mg, 0.46 mmol) in DMF (25 mL) was heated at 150–155° C. in pressure tube for 24 h. The DMF was distilled off under reduced pressure and the residue was filtered through a short column of basic alumina and washed with ethyl acetate and then concentrated. Flash chromatography of the residue on silica gel gave the product (41%) as a white solid: mp 99–100° C.; $^1$H NMR (500 Hz, CDCl$_3$) δ8.74 (dd, J$_1$=1 Hz, J$_2$=1.7 Hz, 1H), 8.12 (d, J=8.6 Hz, 2H), 7.83–7.76 (m, 4H), 7.32 (m, 1H).

Example 17

Preparation of Compound 22

To LiAlH$_4$ (8 mmol) in THF (25 mL) was added 21 (0.96 g, 5.3 mmol) in THF (15 mL) slowly while the flask was cooled with ice. The mixture was stirred at room temperature for 10–30 min then stirred at reflux for 4 h under nitrogen. The mixture was cooled in an ice bath and aqueous sodium hydroxide solution (0.5 mL, 10%) was added. The mixture was stirred until the residue became white and the solid was filtered and washed with methylene chloride (4×5 mL). The methylene chloride solution was dried with anhydrous sodium sulfate, concentrated, and the crude product was chromatographed on silica gel to give the product as a yellow liquid. A small amount of ethanol was added and the pure amine 22 was obtained as a white solid (74%) after filtration: mp 114–117° C.; $^1$H NMR (500 Hz, CDCl$_3$) δ8.66 (d, J=4.4 Hz, 1H), 7.94 (d, J=8.1 Hz, 2H), 7.70 (m, 2H), 7.39 (d, J=8.0 Hz), 7.19 (m, 1H), 3.90 (s, 2H), 1.98 (s, 2H).

Example 18

Preparation of Compound 23

A mixture of 2,6-dichloropurine (1, 0.19 g, 1 mmol), amine 22 (0.39 g, 2.15 mmol) in ethanol (13 mL), and water (3.4 mL) was heated at 100–110° C. under nitrogen for 24 h and then it was cooled to room temperature. The mixture was concentrated and water (5 mL) was added. A solid was filtered and washed with water (2×5 mL) and dried under vacuum to give the product (93%) as yellow solid: mp 260° C. (dec); $^1$H NMR (500 Hz, DMSO-d$_6$) δ12.4 (bs, 1H), 8.76 (m, J=1 Hz, 1H), 8.28 (s, 1H), 8.16 (d, J=8.1 Hz, 2H), 8.03 (d, J=7.8 Hz, 1H), 7.97 (m, 1H), 7.58 (d=8.6 Hz, 2H), 7.45 (m, 1H), 4.82 (s, 2H).

Example 19

Preparation of Compound 24

To the solution of compound 23 (0.33 g, 1 mmol) in DMSO (5.2 mL), added potassium carbonate (0.7 g, 5 mmol) and 2-iodopropane (0.5 g, 3 mmol). The mixture was stirred at ambient temperature under nitrogen for 24 h and poured into ice water (30 mL). After filtration, the solid was washed with water (4×5 mL), dried under vacuum to give the crude product as a yellow solid. Flash column chromatography of the crude product on silica gel and recrystallization provided the pure product (76%) as white crystals: mp 178–179° C.; $^1$H NMR (500 Hz, CDCl$_3$) δ8.68 (m, 1H), 7.96 (d, J=8 Hz, 2H), 7.76–7.70 (m, 2H), 7.73 (s, 1H), 7.47 Hz, 2H), 7.22 (m, 1H), 4.89 (s, 1H), 4.79 (m, 1H), 1.54 (d, J=6.8 Hz, 6H); CI MS m/z=379 [C$_{20}$H$_{19}$ClN$_6$+H]$^+$. Anal. Calcd. for C$_{20}$H$_{19}$ClN$_6$: C, 63.41; H, 5.05; N, 22.18. Found: C, 63.07; H, 5.01; N, 22.01.

Example 20

Preparation of Compound 17

To compound 24 (0.7 g, 1.8 mmol) was added (R)-(−)-2 amino-1-butanol (3.5 g, 3.9 mmol) stirred in a sealed tube for 2 h at 190° C. The reaction mixture was allowed to cool and then was partitioned between EtOAc and brine. The EtOAc was separated, washed with saturated brine (4×), dried with Na$_2$SO$_4$, and concentrated. The product was air dried to give an oil, then dissolved in EtOAc. The EtOAc solution was cooled again, and the precipitate collected, washed with cold EtOAc (2×), air dried, and heated in vacuo for 2 h to give 17 (0.54 g, 67%): mp 98–100° C.; $^1$H NMR (300 MHz, CDCl$_3$) δ8.00–7.85 (m, 2H), 7.75–7.55 (m, 2H), 7.50–7.35 (m, 3H), 7.30–7.15 (m, 1H), 6.40–6.20 (bs, 1H), 5.00–4.82 (m, 1H), 4.80–4.68 (bs, 3H), 4.60 (heptuplet, 1H), 3.98–3.70 (m, 2H), 3.70–3.54 (dd, 1H), 2.10 (bs, 1H), 1.75–1.53 (m, 2H), 1.51 (d, 6H), 1.00 (t, 3H); IR (KBr) 3406, 2969, 1601, 1490, 1389, 1254, 779 cm$^{-1}$; API MS m/z=432 [$C_{24}H_{29}N_7O$+H]$^+$.

Example 21

Preparation of Compound 25

To compound 4 (0.14 g, 0.33 mmol) was added 3-(tributylstannyl)pyridine (0.15 g, 0.33 mmol), Pd(PPh$_3$)$_4$ (0.06 g, 0.41 mmol), and toluene (10 mL). The solution was degassed with argon for 8 min in a sealed tube, and heated in an oil bath for 3 h at 130° C. The cooled reaction mixture was diluted with saturated NaHCO$_3$ and extracted with CH$_2$Cl$_2$ (3×50 mL). The combined organic extracts were washed with brine and dried over Na$_2$SO$_4$. The reaction mixture was purified by column chromatography on silica gel to give the desired coupling product. The product was dissolved in acetonitrile and washed with hexane (3×10 mL) to remove a portion of the tin contaminants. The reaction mixture was again purified by column chromatography on reversed phase silica gel to give compound 25 (0.04 g): $^1$H NMR (300 MHz, CDCl$_3$) δ8.83 (s, 1H), 8.58 (d, 1H), 7.88–7.83 (m, 1H), 7.56–7.46 (m, 5H), 7.38–7.33 (m, 1H), 5.99 (s, 1H), 5.11 (s, 1H), 4.90–4.83 (m, 2H), 4.63–4.56 (m, 1H), 3.92–3.81 (m, 2H), 3.67–3.60 (m, 1H), 1.69–1.49 (m, 8H), 1.05–1.00 (t, 3H); CI MS m/z=432 [$C_{24}H_{29}N_7O$+H]$^+$.

Example 22

Preparation of Compound 27

A mixture of diethyl(3-pyridyl)borane (26, 540 mg, 3.67 mmol), 4-bromobenzonitrile (803 mg, 4.41 mmol) and Pd(PPh$_3$)$_4$ (144 mg, 0.13 mmol) in toluene (9 mL), ethanol (1.3 mL) and 2M aqueous sodium carbonate solution (4.1 mL, 8.2 mmol) was heated at 90–100° C. under nitrogen for 27 h. The mixture was cooled to room temperature and water (10 mL) was added. The organic layer was separated and the aqueous layer was extracted with ethyl acetate (2×20 mL). The combined organic layers were washed with brine (2×15 mL) and dried over anhydrous sodium sulfate. Flash chromatography of the crude product on silica gave the product as a white solid (80%): mp 95–96° C.

Example 23

An Alternative Preparation of 27 is Described Below

A flask charged with 4-bromobenzonitrile (360 mg, 2.0 mmol), bis(pinacolato)diboron (560 mg, 2.2 mmol), potassium acetate (590 mg, 6.0 mmol) and PdCl$_2$(dppf) (49 mg, 0.06 mmol) was flushed with nitrogen and DMF (12 mL) was added. The mixture was heated at 80–85° C. for 4 h and then cooled to room temperature at which time PdCl$_2$(dppf) (49 mg, 0.06 mmol), 3-bromopyridine (385 δL, 3.40 mmol), and 2M aqueous sodium carbonate solution (5 mL, 10 mmol) was added. The mixture was stirred at 80–85° C. for 24 h and extracted with ethyl ether (3×30 mL) and then washed with brine (3×15 mL) and dried with anhydrous sodium sulfate. Flash chromatography of the crude product on silica gel gave the product as white crystals (56%): mp 96–97° C.; $^1$H NMR (500 Hz, CDCl$_3$) δ8.55 (dd, J$_1$=1 Hz, J$_2$=1.4 Hz, 1H), 8.66 (m, 1H), 7.90–7.87 (m, 1H), 7.77 (d, J=7.8 Hz, 2H), 7.69 (d, J=8.8 Hz, 2H), 7.42 (m, 1H).

Example 24

Preparation of Compound 28

To LiAlH$_4$ (8 mmol) in THF (25 mL) was added 27 (0.96 g, 5.3 mmol) in THF (25 mL) slowly while the flask was cooled with ice. The mixture was stirred at room temperature for 10–30 min then stirred at reflux for 4 h under nitrogen. The mixture was cooled in an ice bath and aqueous sodium hydroxide solution (0.5 mL, 10%) was added. The mixture was stirred until the residue became white and the solid was filtered and washed with methylene chloride (4×5 mL). The methylene chloride solution was dried with anhydrous sodium sulfate, concentrated, and the crude product was chromatographed on silica gel to give the product as a yellow liquid. A small amount of ethanol was added and the pure amine 28 was obtained as a white solid (46%) after filtration: mp 94–96° C.; $^1$H NMR (500 Hz, CDCl$_3$) δ8.74 (d, J=2.4 Hz, 1H), 8.48 (dd, J$_1$=1.5 Hz, J$_2$=4.7 Hz, 1H), 7.77 (m, 1H), 7.45 (d, J=8.10 Hz, 2H), 7.33 (d, J=8.0 Hz, 2H), 7.25 (m, 1H), 3.83 (s, 2H), 2.25 (s, 2H).

Example 25

Preparation of Compound 29

A mixture of 2,6-dichloropurine (1, 0.19 g, 1 mmol), amine 28 (0.4 g, 2.15 mmol) in ethanol (13 mL), water (3 mL) was heated at 100–110° C. under nitrogen for 24 h and then it was cooled to room temperature. The mixture was concentrated and water (5 mL) was added. A solid was filtered and washed with water (2×5 mL) and dried under vacuum to give the product (92%) as a yellow solid: mp 219° C. (dec); $^1$H NMR (500 Hz, DMSO-d$_6$) δ13.2 (bs, 1H), 8.99 (s, 1H), 8.66 (d, J=3.5 Hz, 1H), 8.28 (s, 1H), 8.16 (d, J=7.3 Hz, 1H), 7.80 (d, J=7.6 Hz, 2H), 7.60–7.57 (m, 3H).

Example 26

Preparation of Compound 30

To a solution of 29 (0.3 g, 1 mmol) in DMSO (5 mL), was added potassium carbonate (0.7 g, 5 mmol) and 2-iodopropane (0.5 g, 3 mmol). The mixture was stirred at ambient temperature under nitrogen for 24 h and poured into ice water (30 mL). After filtration, the solid was washed with water (4×5 mL), dried under vacuum to give the crude product as a yellow solid. Flash column chromatography of the crude product on silica gel and recrystallization provided the pure product (76%) as white crystals: mp 178–179° C.; $^1$H NMR (500 Hz, CDCl$_3$) δ8.82 (d, J=1.3 Hz, 1H), 8.59–8.58 (m, 1H), 7.86–7.84 (m, 1H), 7.72 (s, 1H), 7.56–7.48 (m, 4H), 7.37–7.34 (m, 1H), 4.88 (s, 2H), 4.82 (m, 1H), 1.56 (d, J=0.7 Hz, 3H), 1.55 (d, J=0.8 Hz, 3H); CI MS m/z=379 [$C_{20}H_{19}ClN_6$+H]$^+$. Anal. Calcd. for $C_{20}H_{19}ClN_6$: C, 63.41; H, 5.05; N, 22.18. Found: C, 63.24; H, 4.97; N, 21.93.

Example 27

Preparation of Compound 32

To a mixture of 4 (0.05 g, 0.11 mmol) was added 4-(tributylstannyl)pyridine (0.06 g, 0.16 mmol), Pd(PPh$_3$)$_4$ (0.02 g, 0.02 mmol), and toluene (2.5 mL). The reaction mixture was degassed and heated in a sealed tube at 125° C. for 3 h. The reaction mixture was cooled to room temperature then saturated NaHCO$_3$ (30 mL) was added followed by extraction with CH$_2$Cl$_2$ (3×30). The organic layer was washed with brine (50 mL), dried with MgSO$_4$, and concentrated. The reaction mixture was purified by column chromatography on silica gel to give 32: $^1$H NMR (300 MHz, CDCl$_3$) δ8.65 (s, 2H), 7.60–7.57 (m, 2H), 7.49–7.45 (m, 5H), 6.20 (s, 1H), 4.93 (d, 1H), 4.84 (s, 2H), 4.65–4.57 (m, 1H), 3.92–3.80 (m, 2H), 3.68–3.51 (m, 1H), 1.68–1.58 (m, 2H), 1.52 (d, 6H), 1.05–0.99 (t, 3H).

Example 28

Preparation of Compound 33

To compound 4 (0.18 g, 0.43 mmol) was added 4-vinylphenylboronic acid (0.19 g, 1.28 mmol), Pd(PPh$_3$)$_4$ (0.09 g, 0.08 mmol), Na$_2$CO$_3$ (2M, 0.85 mL), was added toluene (5 mL). The mixture was degassed with argon for 10 min. The resulting solution was heated in a sealed tube at 135° C. for 4.5 h. The cooled solution was diluted with water and extracted with CH$_2$Cl$_2$ (3×50 mL). The combined organic extracts were washed with brine and dried over Na$_2$SO$_4$. The solution was purified by flash column chromatography (2×) on silica gel to give the desired product 33 as a yellow solid (0.09 g): mp 130–131° C.; $^1$H NMR (300 MHz, CDCl$_3$) δ7.57–7.42 (m, 9H), 6.80–6.70 (dd, 1H), 5.98 (s, 1H), 5.79 (d, 1H), 5.27 (d, 1H), 4.88 (d, 1H), 4.84–4.72 (m, 2H), 4.63–4.56 (m, 1H), 3.92–3.81 (m, 2H), 3.66–3.60 (m, 1H), 1.68–1.52 (m, 8H), 1.05–1.00 (t, 3H); IR (CH$_2$Cl$_2$) 3293, 2968, 1601 1390 cm$^{-1}$; CI MS m/z=457 [C$_{27}$H$_{32}$N$_6$O+H]$^+$.

Example 29

Preparation of Compound 34

To compound 33 (0.008 g, 0.016 mmol) was added OsO4 (0.007 g, 0.026 mmol), pyridine (0.08 mL), and toluene (0.75 mL). The reaction mixture was stirred at room temperature in the dark for 1 h, concentrated in vacuo, and then slurried in methanol/water (9:1). Sodium metabisulfite (0.07 g) was added and the reaction was stirred for 1 h. The mixture was washed with brine, extracted with CH$_2$Cl$_2$ (3×10 mL), dried over Na$_2$SO$_4$, and concentrated. The product was purified by column chromatography on silica gel to give compound 34 (0.003 g) as a tan solid: $^1$H NMR (300 MHz, CDCl$_3$) δ7.51 (s, 1H), 7.43–7.35 (m, 6H), 7.25–7.22 (m, 2H), 6.51 (s, 1H), 4.98 (d, 1H), 4.35–4.25 (m, 2H), 4.64–4.54 (m, 1H), 3.93–3.80 (m, 3H), 3.74–3.59 (m, 3H), 1.68–1.58 (m, 2H), 1.52 (d, 6H), 1.06–0.99 (t, 3H).

Example 30

Preparation of Compound 36

To compound 4 (0.12 g, 0.27 mmol) was added 3-aminophenylboronic acid hydrochloride (0.12 g, 0.69 mmol), and Pd(PPh$_3$)$_4$ (0.09 g, 0.75 mmol) in a sealed tube filled with argon. To this mixture was added toluene (5 mL) and Na$_2$CO$_3$ (2M, 0.55 mL). The resulting solution was degassed with argon for 5 min and placed in a 130° C. oil bath for 6 h. The cooled solution was diluted with water and extracted with CH$_2$Cl$_2$ (3×50 mL). The combined organic layers were washed with brine, dried over Na$_2$SO$_4$, and concentrated. The solution was purified by column chromatography on silica gel to yield 36 (0.04 g, 36%): $^1$H NMR (300 MHz, CDCl$_3$) δ7.52–7.46 (m, 3H), 7.39 (d, 2H), 7.23–7.18 (m, 1H), 6.96 (d, 1H), 6.88 (t, 1H), 6.68–6.66 (m, 1H), 6.12 (s, 1H), 4.90 (d, 1H), 4.79 (s, 2H), 4.62–4.57 (m, 1H), 3.92–3.76 (m, 4H), 3.66–3.60 (m, 1H), 1.65–1.48 (m, 8H), 1.04–0.99 (m, 3H); CI MS m/z=446 [C$_{25}$H$_{31}$N$_7$O+H]$^+$.

Example 31

Preparation of Compound 38

To a suspension of Pd(PPh$_3$)$_4$ (0.02 g, 0.01 mmol) in anhydrous DME (8 mL) was added 4 (0.12 g, 0.27 mmol) and the mixture stirred at room temperature for 10 min. To this solution was added 3-(trifluoromethyl)phenylboronic acid (37; 0.12 g, 0.65 mmol) in a minimum of EtOH, followed by Na$_2$CO$_3$ (2M, 0.27 mL), and the resulting mixture was heated at reflux for 20 h. The cooled reaction mixture was diluted with water and extracted with CH$_2$Cl$_2$ (3×50 mL). The combined organic layers were washed with brine, dried over Na$_2$SO$_4$, and concentrated. The reaction mixture was purified by column chromatography on normal phase silica gel followed by reversed phase column chromatography to obtain 38 (0.04 g, 33%) as an off white solid: mp 60–67° C.; $^1$H NMR (300 MHz, CDCl$_3$) δ7.81 (s, 1H), 7.74 (d, 1H), 7.58–7.45 (m, 7H), 5.98 (s, 1H), 4.90–4.83 (m, 3H), 4.63–4.59 (m, 1H), 3.90–3.81 (m, 2H), 3.66–3.60 (m, 1H), 1.68–1.51 (m, 8H), 1.05–1.00 (t, 3H); IR (KBr) 3406, 2969, 1602, 1489, 1335 cm$^{-1}$; CI MS m/z=499 [C$_{26}$H$_{29}$FN$_7$O+H]$^{+1}$.

Example 32

Preparation of Compound 40

A mixture of 4 (0.13 g, 0.31 mmol), 2-naphthaleneboronic acid (39; 0.11 g, 0.62 mmol) and Pd(PPh$_3$)$_4$ (0.09 g, 0.08 mmol) was placed in a sealed tube that was filled with argon. To the mixture was added toluene (5 mL) and Na$_2$CO$_3$ (2M, 0.62 mL). The tube was quickly sealed and heated at 125° C. in an oil bath for 6 h. The cooled solution was diluted with water and extracted with CH$_2$Cl$_2$ (3×50 mL). The organic layers were washed with brine, dried over Na$_2$SO$_4$, and concentrated. The reaction mixture was purified by column chromatography on normal phase silica gel, followed by reversed phase chromatography to give 40 (0.04 g, 28%): mp 70–75° C.; $^1$H NMR (300 MHz, CDCl$_3$) δ8.02 (s, 1H), 7.92–7.84 (m, 3H), 7.74–7.67 (m, 3H), 7.51–7.44 (m, 5H), 5.96 (s, 1H), 4.89–4.84 (m, 3H), 4.66–4.57 (m, 1H), 3.93–3.82 (m, 2H), 3.67–3.61 (m, 1H), 1.76–1.50 (m, 8H), 1.06–1.01 (t, 3H); IR (KBr) 3422, 2927, 1601, 1491, 1388 cm$^{-1}$.

Example 33

Preparation of Compound 43

To compound 4 (0.14 g, 0.33 mmol) was added 4-methoxyphenylboronic acid (42, 0.11 g, 0.71 mmol), Pd(PPh$_3$)$_4$ (0.10 g, 0.087 mmol), Na$_2$CO$_3$ (2M, 0.66 mL), and toluene (7 mL). The solution was degassed for 8 min with argon and heated in an oil bath at 125° C. for 6 h. The cooled solution was diluted with water and extracted with CH$_2$Cl$_2$ (3×50 mL). The combined organic layers were washed with brine, dried over Na$_2$SO$_4$, filtered, and concentrated. The reaction mixture was purified by normal phase column chromatography followed by reversed phase chromatography to give 43 (0.05 g, 28%) as a white solid: mp 128–130° C.; $^1$H NMR (300 MHz, CDCl$_3$) δ7.52–7.50 (m, 5H), 7.41 (d, 2H), 6.97 (d, 2H), 5.93 (s, 1H), 4.89–4.79 (m, 3H), 4.63–4.56 (m, 1H), 3.92–3.81 (m, 5H), 3.67–3.60 (m, 1H), 1.68–1.49 (m, 8H), 1.05–1.00 (t, 3H); IR (KBr) 3417, 2931, 1610, 1499, 1389 cm$^{-1}$; CI MS m/z=461 [C$_{26}$H$_{32}$N$_6$O$_2$+H]$^+$.

Example 34

Preparation of Compound 45

To a solution of s-BuLi (5 mL, 6.24 mmol) and TMEDA (1 mL) in anhydrous THF (35 mL) at −75° C. under argon was added dropwise a solution of N,N-diethylbenzamide (0.98 g, 5.57 mmol) in THF (5 mL). The mixture was stirred for 50 min and then treated with trimethylborate (2 mL, 17 mmol). The solution was allowed to warm to room temperature overnight. The colorless solution was cooled to 0° C. and acidified to pH=6 with 2N HCl. The THF was removed in vacuo and the residue was diluted with water. This was extracted with CH$_2$Cl$_2$ (3×50 mL) and the combined organic layers were washed with brine, dried over Na$_2$SO$_4$, concentrated in vacuo, followed by removal of trace solvent on the vacuum pump to give 45 as an off-white foamy solid: $^1$H NMR (300 MHz, CD$_3$OD) δ7.67–7.39 (m, 4H), 3.88–3.69 (q, 4H), 1.41–1.30 (t, 6H).

Example 35

Preparation of Compound 46

To compound 4 (0.14 g, 0.31 mmol) was added 2-(diethylcarbamoyl)phenylboronic acid (45, 0.29 g, 1.31 mmol), Pd(PPh$_3$)$_4$ (0.1 g, 0.09 mmol), Na$_2$CO$_3$ (2M, 0.63 mL), toluene (5 mL), and the mixture degassed with argon for 10 min. The mixture was heated in an oil bath for 5 h at 135° C. The cooled solution was diluted with water and extracted with CH$_2$Cl$_2$ (3×50 mL). The organic layers were combined, washed with brine, dried over Na$_2$CO$_3$, and concentrated. The reaction mixture was purified by normal phase column chromatography on silica gel, followed by reversed phase column chromatography to give 46 (0.03 g, 18%) as a yellow solid: $^1$H NMR (300 MHz, CDCl$_3$) δ7.49–7.36 (m, 9H), 6.18 (s, 1H), 4.93 (d, 1H), 4.78 (s, 2H), 4.64–4.55 (m, 1H), 3.92–3.60 (m, 4H), 3.06–2.92 (m, 2H), 2.69–2.64 (m, 1H), 1.68–1.51 (m, 8H), 1.04–0.99 (t, 3H), 0.91–0.86 (t, 3H), 0.77–0.72 (t, 3H), CI MS m/z=530 [C$_{30}$H$_{39}$N$_7$O$_2$+H]$^+$.

Example 36

Preparation of Compound 48

To a suspension of Pd(PPh$_3$)$_4$ (0.08 g, 0.69 mmol) in DME was added 4 (0.129 g, 0.30 mmol) and the mixture stirred for 10 min at room temperature. To this was added 3-nitrophenylboronic acid (47, 0.157 g, 0.94 mmol) and Na$_2$CO$_3$ (2 M, 0.59 mL). The solution was heated at reflux under argon overnight. The cooled solution was diluted with water and extracted with CH$_2$Cl$_2$ (3×50 mL). The organic layers were combined, washed with brine, dried over Na$_2$SO$_4$, and concentrated in vacuo. The solution was purified by flash column chromatography on silica gel to give 48 (0.04 g, 29%) as a bright yellow solid: mp 73–77° C.; $^1$H NMR (300 MHz, CDCl$_3$) δ8.43 (s, 1H), 8.20 (d, 1H), 7.89 (d, 1H), 7.63–7.43 (m, 6H), 6.01 (s, 1H), 4.95–4.76 (m, 3H), 4.68–4.58 (m, 1H), 3.98–3.80 (m, 2H), 3.68–3.60 (m, 1H), 1.71–1.40 (m, 8H), 1.02–0.98 (t, 3H); IR (KBr) 3405, 2930, 1713, 1602, 1490, 1351 cm$^{-1}$; CI MS m/z=476 [C$_{25}$H$_{29}$N$_7$O$_3$+H]$^+$.

Example 37

Preparation of Compound 50

To a suspension of Pd(PPh$_3$)$_4$ (0.09 g, 0.08 mmol) in DME (5 mL) was added 4 (0.14 g, 0.32 mmol) and the mixture stirred at room temperature for 15 min. To this was added benzo[b]furan-2-boronic acid (49, 0.153 g, 0.94 mmol) and Na$_2$CO$_3$ (2 M, 0.63 mL). The solution was heated at reflux under argon overnight. The reaction mixture was cooled, diluted with water, extracted with CH$_2$Cl$_2$ (3×50 mL). The organic layers were combined, washed with brine, dried over Na$_2$SO$_4$, and concentrated in vacuo. The solution was purified by flash column chromatography on silica gel followed by flash column chromatography on reversed phase silica to give 50 (0.09 g, 60%) as a white solid: $^1$H NMR (300 MHz, CDCl$_3$) δ7.82 (d, 2H), 7.58–7.42 (m, 5H), 7.30–7.19 (m, 2H), 7.01 (s, 1H), 6.11 (s, 1H), 4.91 (d, 1H), 4.81 (s, 2H), 4.62–4.58 (m, 1H), 3.92–3.80 (m, 2H), 3.66–3.60 (m, 1H), 1.66–1.48 (m, 8H), 1.04–0.99 (t, 3H); CI MS m/z=471 [C$_{27}$H$_{30}$N$_6$O$_2$+H]$^+$.

Example 38

Preparation of Compound 52

To compound 4 (0.46 g, 1.20 mmol) was added 1-amino-1-cyclopentanemethanol (51, 1.0 g, 8.61 mmol) and EtOH (2 mL) and the mixture was heated in an oil bath at 150° C. for 60 h. The brown solution was cooled and heated again at 150° C. for 48 h. The reaction mixture was cooled and concentrated in vacuo. The solution was purified by flash column chromatography on silica gel to give 52 (0.39 g, 71%) as a tan solid: $^1$H NMR (300 MHz, CDCl$_3$) δ7.48–7.40 (m, 3H), 7.29–7.20 (m, 2H), 6.88 (s, 1H), 6.25 (s, 1H), 5.10 (s, 1H), 4.72 (s, 2H), 4.63–4.51 (m, 1H), 3.78 (s, 2H), 2.10–1.65 (m, 8H), 1.54 (d, 6H); CI MS m/z=459 [C$_{21}$H$_{27}$BrN$_6$O+H]$^+$.

Example 39

Preparation of Compound 53

To a suspension of Pd(PPh$_3$)$_4$ (0.07 g, 0.06 mmol) in DME (5 mL) was added 52 (0.102 g, 0.22 mmol) and stirred at room temperature for 15 min. To this was added phenylboronic acid (0.098 g, 0.80 mmol) and Na$_2$CO$_3$ (2 M, 0.44 mL). The solution was heated at reflux under argon for 18 h. The reaction mixture was diluted with water, extracted with CH$_2$Cl$_2$ (3×50 mL), washed with brine, and dried over Na$_2$SO$_4$. The solution was purified by flash column chromatography on silica gel followed by flash column chromatography on reversed phase silica gel to give 53 (0.02 g, 20%): $^1$H NMR (300 MHz, CDCl$_3$) δ7.59–7.31 (m, 10H), 6.95 (s, 1H), 5.95 (s, 1H), 5.10 (s, 1H), 4.79 (s, 2H), 4.61–4.52 (m, 1H), 3.76 (s, 2H), 2.01–1.61 (m, 8H), 1.54 (d, 6H); CI MS m/z 457 [C$_{27}$H$_{32}$N$_6$O+H]$^+$.

Example 40

Preparation of Compound 54

To compound 3 (0.26 g, 0.67 mmol) was added trans-4-aminocyclohexanol hydrochloride (0.62 g, 4.11 mmol), Et$_3$N (0.58 mL, 4.16 mmol), and ethanol (5 mL). The mixture was heated for 5 h at 135° C. in an oil bath. The temperature increased to 150° C. and heating was continued for a further 48 h. The solution was cooled and evaporated to give a yellow oil: CI MS m/z=459 [C$_{21}$H$_{27}$BrN$_6$O+H]$^+$.

Example 41

Preparation of Compound 55

To compound 3 (0.50 g, 1.31 mmol) was added cis-1,2-diaminocyclohexane (1.57 mL, 13.1 mmol) and EtOH (4 mL). The mixture was heated in an oil bath at 150° C. for 6 h. The reaction mixture was concentrated in vacuo. The reaction mixture was purified by column chromatography on silica gel to give 55 (0.49 g, 82%) as a yellow solid: $^1$H NMR (300 MHz, CDCl$_3$) δ7.43–7.40 (m, 3H), 7.23 (d, 2H), 6.21 (s, 1H), 5.04 (d, 1H), 4.72 (s, 2H), 4.67–4.58 (m, 1H), 4.08–4.05 (m, 1H), 3.17–3.15 (m, 1H), 2.08 (s, 2H), 1.65–1.38 (m, 14H); CI MS m/z=458 [C$_{21}$H$_{28}$BrN$_7$+H]$^+$.

Example 42

Preparation of Compound 56

To compound 55 (0.10 g, 0.22 mmol) was added 2-(tributylstannyl)pyridine (0.10 g, 0.27 mmol), Pd(PPh$_3$)$_4$ (0.05 g, 0.04 mmol), and toluene (5 mL). The solution was degassed with argon for 8 min and heated at 135° C. for 3 h. The cooled solution was diluted with water, extracted with CH$_2$Cl$_2$ (3×50 mL), and the combined organic extracts were washed with brine, dried over Na$_2$SO$_4$. filtered, and concentrated. The solution was followed by flash column chromatography (2×) to give the desired product 56 (0.03 g, 36%) yellow crystalline solid: $^1$H NMR (300 MHz, CDCl$_3$) δ8.68 (d, 1H), 7.96 (d, 2H), 7.78–7.69 (m, 2H), 7.49 (s, 1H), 7.44 (d, 2H), 7.23–7.18 (m, 1H), 6.10 (s, 1H), 5.10–5.00 (m, 1H), 4.83 (s, 2H), 4.69–4.60 (m, 1H), 4.20–4.10 (m, 1H), 3.27–3.13 (m, 1H), 2.48 (s, 2H), 1.78–1.42 (m, 14H); CI MS m/z=457 [C$_{26}$H$_{32}$N$_8$+H]$^+$.

Example 43

Preparation of Compound 57

To compound 1 (0.50 g, 1.31 mmol) was added trans-1,2-diaminocyclohexane (2.52 mL, 21 mmol), and EtOH (6 mL). The reaction mixture was placed in an oil bath and heated to 190° C. for 25 h. The reaction mixture was removed from the heat and cooled to room temperature, concentrated for purification. The reaction mixture was purified by column chromatography on silica gel to yield 57 (520 mg, 87%) as an off white foam: $^1$H NMR (300 MHz, DMSO) δ7.95 (bs, 1H), 7.85 (s, 1H), 7.50 (d, 2H), 7.34 (d, 2H), 6.17 (d, 1H), 4.70–4.40 (m, 1H), 2.00–1.71 (m, 4H), 1.70–1.52 (m, 2H), 1.41 (d, 6H), 1.30–0.92 (m, 4H); API MS m/z=460 $[C_{21}H_{28}N_7Br+H]^+$.

Example 44

Preparation of Compound 58

Compound 57 (0.15 g, 0.32 mmol) was added to a suspension of Pd(PPh$_3$)$_4$ (0.11 g, 0.1 mmol) in DME (7 mL) and stirred at room temperature for 15 min. Phenylboronic acid (0.14 g, 1.14 mmol) was added followed by the Na$_2$CO$_3$ (2M, 0.62 mmol). The reaction mixture was refluxed under argon for 18 h and allowed to stir at room temperature for 51 h. It was then diluted with water, extracted with CH$_2$Cl$_2$, washed with brine, and then extracted with CH$_2$Cl$_2$. The organic layer was evaporated, dried over anhydrous Na$_2$SO$_4$, purified by column chromatography, and placed in vacuo for 18 h to give 58 (0.10 g, 72%) as a white solid: $^1$H NMR (300 MHz, CDCl$_3$) δ7.62–7.35 (m, 10H), 5.92 (br, 1H), 4.83 (br, 2H), 4.74–4.56 (m, 2H), 3.77–3.55 (m, 1H), 2.55–2.43 (m, 1H), 2.16–1.91 (m, 2H), 1.73 (br, 2H), 1.52 (d, 6H), 1.37–1.09 (m, 6H); API MS m/z=456 $[C_{27}H_{33}N_7+H]^+$.

Example 45

Preparation of Compound 59

To compound 57 (460 mg, 1.0 mmol) in solution with CH$_2$Cl$_2$ (2 mL) was added acetic anhydride (0.44 mL, 4.6 mmol), catalytic DMAP, and pyridine (0.5 mL). The mixture was stirred at room temperature for 2.5 h. The mixture was diluted with CH$_2$Cl$_2$, washed with 2N HCl, and the combined organics were then washed with NaHCO$_3$. The organics were then washed with brine, dried over Na$_2$SO$_4$, filtered, and concentrated to give 59 (472 mg, 94%) as an offwhite solid: $^1$H NMR (300 MHz, DMSO-d$_6$) δ7.76 (s, 1H), 7.42 (d, 2H), 7.29 (d, 2H), 4.68–4.40 (m, 1H), 4.10 (s, 3H), 3.61–3.40 (m, 2H), 2.15–1.80 (m, 2H), 1.74–1.55 (m, 4H), 1.45 (d, 6H), 1.35–1.05 (m, 4H); API MS m/z=500 $[C_{23}H_{30}BrN_7O+H]^+$.

Example 46

Preparation of Compound 60

To a suspension of Pd(PPh$_3$)$_4$ (0.11 g, 0.1 mmol) in DME (7 mL) was added compound 59 (0.15 g, 0.3 mmol) and stirred at room temperature for 15 mL under argon. Phenylboronic acid (0.13 g, 1.06 mmol) was added, followed by Na$_2$CO$_3$ (2M, 0.62 mL). The reaction mixture was refluxed under argon for 18 h. The reaction mixture was then diluted with H$_2$O, extracted with CH$_2$Cl$_2$, washed with brine, and extracted with CH$_2$Cl$_2$. The organic layer was dried over anhydrous Na$_2$SO$_4$, purified by column chromatography, concentrated in vacuo for 18 h to yield 60 (61 mg, 42%): $^1$H NMR (300 MHz, DMSO-d$_6$) δ7.96 (s, 1H), 7.72 (s, 1H), 7.51 (t, 3H), 7.40–7.28 (m, 3H), 7.28–7.13 (m, 2H), 5.84 (br, 1H), 4.46 (br, 3H), 3.47 (br, 2H), 1.83 (br, 1H), 1.62 (s, 4H), 1.43 (d, 6H), 0.12 (s, 3H); API MS m/z=498 $[C_{29}H_{35}N_7O+H]^+$.

Example 47

Preparation of Compound 61

To compound 3 (0.58 g, 1.53 mmol) was added trans-1,4-diaminocyclohexane (1.78 g, 15.6 mmol), and EtOH (4 mL). The mixture was heated in an oil bath at 150° C. for ca. 60 h. The reaction mixture was purified by column chromatography on silica gel to yield 61 (0.48 g, 68%) as an off white solid: mp 122–125° C.; $^1$H NMR (300 MHz, CDCl$_3$) δ7.43 (s, 1H), 7.40 (d, 2H), 7.20 (d, 2 1–1), 6.27 (s, 1H), 4.75–4.68 (m, 2H), 4.67–4.58 (m, 2H), 3.81–3.68 (m, 1H), 3.45 (s, 2H), 2.88–2.75 (m, 1H), 2.18–2.05 (m, 2H), 2.05–1.89 (m, 2H), 4.52 (d, 6H), 1.45–1.13 (m, 4H); CI MS m/z=459 $[C_{21}H_{28}BrN_7+H]^+$.

Example 48

Preparation of Compound 62

Amine 61 (53 mg, 0.12 mmol) was dissolved in CH$_2$Cl$_2$ (2 mL) and pyridine (5 mL). Acetic anhydride (0.05 g, 0.53 mmol) and DMAP (few crystals) were added. The reaction mixture was allowed to stir at room temperature for 2.25 h. The reaction mixture was diluted with CH$_2$Cl$_2$, washed with 2N HCl, NaHCO$_3$, dried over MgSO$_4$, filtered, and evaporated to yield 62 (0.05 g, 78%) as a white solid: $^1$H NMR (300 MHz, CDCl$_3$) δ7.50–7.20 (m, 5H), 6.02 (br, 1H), 5.29–5.20 (m, 1H), 4.72 (d, 2H), 4.66–4.54 (m, 2H), 3.72 (br, 2H), 2.18–2.06 (m, 2H), 2.06–1.91 (m, 2H), 1.97 (s, 3H), 1.54 (d, 6H), 1.36–1.15 (m, 4H); API MS m/z=500 $[C_{23}H_{30}BrN_7O+H]^+$.

Example 49

Preparation of Compound 64

Compound 61 (0.05 g, 0.11 mmol) was dissolved in CH$_2$Cl$_2$ (3 mL) and Et$_3$N (2 mL) and placed in an ice bath for 10 min. Compound 63 (0.06 g, 0.22 mmol) was dissolved in CH$_2$Cl$_2$ (2 mL), added dropwise, and rinsed with CH$_2$Cl$_2$ (1.5 mL). The ice bath was removed after 20 min and the reaction was allowed to stir for 7 d. The reaction mixture was diluted with CH$_2$Cl$_2$, washed with 2N HCl until the aqueous layer was acidic, washed with NaHCO$_3$, dried over MgSO$_4$, and evaporated. The desired product was isolated by column chromatography and dried in vacuo to yield 64 (0.04 g, 50%) as a green solid: $^1$H NMR (300 MHz, CDCl$_3$) δ8.53 (d, 1H), 8.32–8.20 (m, 2H), 7.59–7.35 (m, 4H), 7.23–7.11 (m, 4H), 6.02 (br, 1H), 4.69–4.45 (m, 5H), 3.57 (br, 1H), 3.12 (br, 1H), 2.87 (s, 1H), 1.97 (br, 2H), 1.75 (br, 2H), 1.48 (d, 6H), 1.27–0.97 (m, 4H); API MS m/z=693 $[C_{33}H_{39}BrN_8O_2S+H]^+$.

Example 50

Preparation of Compound 65

Compound 61 (0.05 g, 0.11 mmol) was dissolved in CH$_2$Cl$_2$ (3 mL) and Et$_3$N (2 mL) and placed in an MeOH/ice bath. Methanesulfonyl chloride (0.012 mg, 0.11 mmol) in CH$_2$Cl$_2$ (2.3 mL) was slowly added. The reaction mixture and ice bath was allowed to come to room temperature. After 1.5 h, the reaction mixture was diluted with CH$_2$Cl$_2$, washed with 2N HCl until the aqueous layer was acidic. The organic layer was washed with NaHCO$_3$, dried over MgSO$_4$, filtered, and evaporated. The product was purified by column chromatography, and dried in vacuo for 14 h to yield 65 (13 mg, 24%) as an off-white solid: $^1$H NMR (300 MHz, CDCl$_3$) δ7.50–7.17 (m, 5H), 5.90 (br, 1H), 4.75–4.57 (m, 3H), 4.11 (d, 1H), 3.69 (br, 1H), 3.30 (br, 1H), 2.99 (s, 3H), 2.18–2.03 (m, 4H), 1.69 (d, 6H), 1.42–1.15 (m, 5H); API MS m/z=538 $[C_{22}H_{30}BrN_7O_2S+H]^+$.

Example 51

Preparation of Compound 66

Compound 61 (0.05 g, 0.11 mmol) was dissolved in toluene (4 mL). 2-Acetylphenylisocyanate (0.024 g, 0.15 mmol) diluted with toluene (1 mL) and added to compound 61. Toluene (6 mL) was added to the reaction mixture. The reaction mixture was placed under reflux for 19 h. The product was purified by column chromatography, concentrated, and dried in vacuo for 23 h to yield 66 (42 mg, 62%) as an off-white solid: $^1$H NMR (300 MHz, CDCl$_3$) δ7.87–7.20 (m, 9H), 6.41 (s, 1H), 5.86 (br, 1H), 4.75–4.54 (m, 4H), 3.69 (br, 1H), 2.60 (s, 3H), 2.12 (br, 4H), 1.51 (d, 6H), 1.42–1.15 (m, 5H); API MS m/z=619 [C$_{30}$H$_{35}$BrN$_8$O$_2$+H]$^+$.

Example 52

Preparation of Compound 67

Compound 61 (0.04 g, 0.10 mmol) was dissolved in CH$_2$Cl$_2$ (2 mL) and pyridine (0.5 mL). Cyclopropanecarbonyl chloride (0.05 g, 0.44 mmol) was added along with DMAP (small amount). The reaction mixture was allowed to stir at room temperature for 2.25 h. The reaction mixture was diluted with CH$_2$Cl$_2$, washed with 2N HCl, saturated NaHCO$_3$, dried over MgSO$_4$, filtered, and evaporated. The product was isolated by column chromatography to yield 67 (0.03 g, 63%) as a white solid: $^1$H NMR (300 MHz, CDCl$_3$) δ7.50–7.20 (m, 5H), 5.96 (br, 1H), 5.41 (d, 1H), 4.72 (d, 2H), 4.66–4.54 (m, 2H), 3.72 (br, 2H), 2.18–1.97 (m, 4H), 1.51 (d, 6H), 1.36–1.15 (m, 5H), 1.06–0.88 (m, 2H), 0.79–0.67 (m, 2H); API MS m/z=526 [C$_{25}$H$_{32}$BrN$_7$O+H]$^+$.

Example 53

Preparation of Compound 69

To a solution of 4-biphenylcarboxaldehyde (1.0 g, 5.49 mmol) in MeOH (20 mL) was added NaBH$_3$CN (0.69 g, 11.0 mmol), and NH$_4$OH (15 mL) and the mixture was stirred at room temperature overnight. To this added HCl and extracted with CHCl$_3$. The resulting aqueous layer was brought to pH>7 with sodium bicarbonate and then extracted with CHCl$_3$. The solution was dried with MgSO$_4$, filtered, and evaporated to give 69 (200 mg) as a white solid: EI MS m/z=183 [C$_{13}$H$_{13}$N]$^+$.

Example 54

Preparation of Compound 69

To compound 70 (2.75 g, 13.9 mmol) was added anhydrous THF (60 mL), heated to reflux, and kept under nitrogen. 1M Borane-THF (69.7 mL) was added dropwise to 70 through an addition funnel resulting in a homogeneous solution. The solution was refluxed for 18 h. The reaction mixture was cooled in an ice water bath and quenched with H$_2$O, 2N HCl (20 mL), followed by 3N NaOH (60 mL). The reaction mixture was extracted with EtOAc (3x). The organic extracts were washed with brine, and dried over sodium sulfate. The crude product was concentrated, dissolved in MeOH, and HCl gas was bubbled through the solution. The solution was filtered in vacuo to give 69 as a white solid: $^1$H NMR (300 MHz, CD$_3$OD) δ7.71 (d, 2H), 7.63 (d, 2H), 7.52 (d, 2H), 7.47–7.30 (m, 3H), 4.13 (s, 2H).

Example 55

Preparation of Compound 71

To compound 1 (6.8 g, 36.0 mmol) and 69 (8.0 g, 36.5 mmol) was added H$_2$O (60 mL) and Hüing's base (9.0 g, 70.0 mmol). The mixture was stirred and heated to reflux for 5 h during which time H$_2$O (50 mL) was added as the reaction continued to thicken. The crude product was collected by filtration, washed with H$_2$O (500 mL) and EtOH (2x30 mL), air dried, and dried in vacuo to give 71 (11.1 g. 92%): mp 267–269° C.

Example 56

Preparation of Compound 72

Compound 71 (4.7 g, 14.0 mmol), K$_2$CO$_3$ (15.0 g, 109 mmol), DMSO (80 mL), and 2-iodopropane (9.4 g, 55.0 mmol) were combined and stirred overnight. H$_2$O and EtOAc were added. The EtOAc layer was separated and washed with brine (3x). The EtOAc solution was dried with MgSO$_4$, concentrated, and crystallized from EtOAc to give 72 (3.5 g, 66%): mp 139–140° C.

Example 57

Preparation of Compound 73

Compound 72 (2.00 g, 5.30 mmol) and (R)-(−)-2-amino-1-butanol (10.8 g, 121 mmol) were combined in a sealed tube, and heated in an oil bath at 190° C. for 2 h. The solution was cooled to 60° C., diluted in EtOAc, washed with brine (4x), dried with Na$_2$SO$_4$, and concentrated. Purification by column chromatography on SiO$_2$ gave the desired product 73 (1.72 g, 75%) as a foam: $^1$H NMR (300 MHz, CDCl$_3$) δ7.65–7.10 (m, 9H), 6.40–6.10 (bs, 1H), 5.05–4.85 (m, 1H), 4.85–4.67 H), 4.60 (heptuplet, 1H), 4.00–3.70 (dd, 2H), 3.76–3.50 (m, 1H), 1.95 (bs, 1H), 1.80–1.55 (m, 2H), 1.51 (d, 6H), 1.03 (t, 3H); IR (CH$_2$Cl$_2$) 3301, 2969, 1601, 1488, 1389, 1255, 762, 698 cm$^{-1}$; API MS m/z=431 [C$_{25}$H$_{30}$N$_6$O+H]$^+$.

Example 58

Preparation of Compound 74

Compound 72 (0.23 g, 0.60 mmol), cis-1,2-diaminocyclohexane (0.72 mL, 6.0 mmol), and ethanol (2 mL) were combined in a sealed tube and heated in an oil bath at 155° C. for 5 d. The ethanol was removed in vacuo and the crude reaction mixture was filtered through a silica plug. The reaction mixture was chromatographed on silica gel, the resulting orange solid was dissolved in CH$_2$Cl$_2$ and a portion of activated charcoal was added. The solution was filtered through a pad of celite and concentrated to give 74 as a yellow solid (0.04 g, 27%): $^1$H NMR (300 MHz, CDCl$_3$) 7.59–7.31 (m, 10H), 6.00 (s, 1H), 5.09 (d, 1H), 4.83 (s, 2H), 4.68–4.62 (m, 1H), 4.11 (s, 1H), 3.70–3.65 (m, 2H), 3.18–3.16 (m, 1H), 2.02 (s, 2H), 1.67–1.42 (m, 12H); CI MS m/z=456 [C$_{27}$H$_{33}$N$_7$+H]$^+$.

Example 59

Preparation of Compound 75

Compound 72 (0.17 g, 0.45 mmol), trans-1,4-diaminocyclohexane (0.53 g, 4.69 mmol), and EtOH (5 mL) were combined in a sealed tube and heated at 155° C. for 5 d. The EtOH was removed in vacuo and the crude mixture was subjected to flash chromatography on silica gel. Recrystallization from CHCl$_3$/MeOH gave 75 (5.8 mg) as an off-white crystalline solid: mp 110–112° C.; $^1$H NMR (300 MHz, CDCl$_3$) δ7.58–7.31 (m, 10H), 5.95 (s, 1H), 4.88–4.78 (m, 2H), 4.69–4.60 (m, 2H), 3.88–3.78 (m, 1H), 3.07–2.98 (m, 1H), 2.26–2.10 (m, 4H), 1.62–1.52 (m, 8H), 1.29–1.15 (m, 4H); CI MS m/z=456 [C$_{27}$H$_{33}$N$_7$+H]$^+$.

Example 60

Preparation of Compound 76

Compound 75 (0.05 g, 0.11 mmol) was dissolved in CH$_2$Cl$_2$ and the solution cooled to 0° C. under an argon atmosphere. A catalytic amount of DMAP, triethylamine (50 L, 0.36 mmol), followed by the acetyl chloride (25 L, 0.36 mmol) were added to the reaction mixture. The solution was warmed to room temperature and washed with $NaHCO_3$ (5%), water, and brine. The solution was dried over $Na_2SO_4$ and concentrated. Purification by flash chromatography on silica gel gave 76 (0.028 g, 53%) as a pale yellow solid: mp 224–225° C.; $^1$H NMR (300 MHz, $CDCl_3$) δ7.59–7.31 (m, 10H), 5.93 (s, 1H), 5.26 (d, 1H), 4.81 (s, 2H), 4.65–4.58 (m, 1H), 3.78–3.75 (m, 2H), 2.18–1.99 (m, 4H), 1.95 (s, 3H), 1.77 (s, 1H), 1.53 (d, 6H), 1.32–1.22 (m, 4H); CI MS m/z=498 $[C_{29}H_{35}N_7O+H]^+$.

Example 61

Preparation of Compound 77

Compound 72 (0.15 g, 0.40 mmol), trans-4-aminocyclohexanol hydrochloride (0.31 g, 1.99 mmol), $Et_3N$ (0.11 mL, 0.8 mmol), and EtOH (5 mL) were combined and heated in a sealed tube at 155° C. for 4 d. Additional trans-4-aminocyclohexanol hydrochloride (0.34 g, 2.2 mmol) and triethylamine (0.60 mL, 4.3 to mmol) were added and the heat was resumed at 155° C. overnight. The crude product was purified by flash column chromatography to give 77 (0.036 g, 20%) as an off-white solid: mp 196–200° C.; $^1$H NMR (300 MHz, $CDCl_3$) δ7.58–7.30 (m, 10H), 5.97 (s, 1H), 4.83–4.81 (m, 2H), 4.66–4.60 (m, 2H), 3.82–3.77 (m, 1H), 3.69–3.62 (m, 1H), 2.17–2.13 (m, 2H), 2.01–1.97 (m, 2H), 1.68 (s, 1H), 1.53 (d, 6H), 1.49–1.20 (m, 4H); CI MS m/z=457 $[C_{27}H_{33}N_6O+H]^+$.

Example 62

Preparation of Compound 78

To compound 61 (0.12 g, 0.26 mmol), was added compound 16 (0.12 g, 0.33 mmol), and $Pd(PPh_3)_4$ (0.06 g, 0.056 mmol) and toluene (5 mL). The resulting mixture was degassed for 10 min with argon. The mixture was heated at 140° C. for 3 h. The cooled solution was diluted with saturated $NaHCO_3$ and extracted with $CH_2Cl_2$ (3×50 mL). The combined organic extracts were washed with brine, dried over $Na_2SO_4$, filtered, and concentrated to give a pale yellow oil which crystallized upon standing at room temperature. The crude product was purified by column chromatography and concentrated to give a white solid. The solid was precipitated with acetonitrile, filtered, washed with ether and hexane to give 78 (0.02 g, 18%): $^1$H NMR (300 MHz, DMSO-$d_6$) δ8.63 (d, 1H), 8.01 (d, 1H), 7.93–7.83 (m, 2H), 7.59–7.44 (m, 4H), 7.34–7.29 (m, 1H), 6.25 (s, 1H), 4.70–4.60 (m, 2H), 4.57–4.49 (m, 2H), 3.65–3.52 (m, 1H), 2.98–2.88 (m, 1H), 1.98–1.90 (m, 4H), 1.48 (d, 6H), 1.42–1.18 (m, 6H); CI MS m/z=457 $[C_{26}H_{32}N_8+H]^+$.

Example 63

Preparation of Compound 78

To compound 24 (200 mg, 0.53 mmol) was added trans-1,4-diaminocyclohexane (2.00 g, 17 mmol) and EtOH (4 mL). The reagents were heated in a sealed tube in an oil bath at 170° C. for 18 h. The mixture was cooled to 60° C. and partitioned between EtOAc and brine. The EtOAc layer was separated, washed with brine (3×), dried with $Na_2SO_4$, and concentrated to give 78 (0.12 g, 50%): mp 135–138° C.; $^1$H NMR (300 MHz, $CDCl_3$) δ8.03–7.82 (m, 2H), 7.80–7.58 (m, 3H), 7.57–7.30 (m, 3H), 7.30–7.05 (m, 1H), 6.20 (bs, 1H), 5.95–4.73 (m, 2H), 4.73–4.45 (m, 2H), 3.90–3.60 (m, 1H), 2.80–2.52 (m, 1H), 2.25–1.80 (m, 4H), 1.80–1.60 (bs, 3H), 1.52 (d, 6H), 1.38–1.05 (m, 4H); IR (KBr) 3422, 2927, 1599, 1489, 1253, 779 cm$^{-1}$; API MS m/z=457 $[C_{26}H_{32}N_8+H]^+$.

Example 64

Preparation of Compound 79

Compound 78 (50 mg, 0.11 mmol) was dissolved in $CH_2Cl_2$ (2 mL) and stirred at room temperature. Pyridine (0.5 mL), $AC_2O$ (0.5 ml, 4.9 mmol), and DMAP (few crystals) were added to the reaction mixture and stirred for 2 h. The solution was diluted in $CH_2Cl_2$ and washed in 2N HCl. The HCl layer was concentrated, $CH_2Cl_2$ was added and the aqueous phase neutralized with saturated $NaHCO_3$. The $CH_2Cl_2$ layer was separated, dried ($MgSO_4$), and concentrated to give 79 (0.03 g, 55%) as a white solid: $^1$H NMR (300 MHz, $CDCl_3$) δ8.00–7.80 (m, 2H), 7.81–7.57 (m, 2H), 7.56–7.33 (m, 3H), 7.30–7.05 (m, 2H), 6.15–5.90 (bs, 1H), 5.47–5.28 (m, 1H), 4.96–4.72 (m, 2H), 4.73–4.45 (m, 2H), 2.25–1.82 (m, 4H), 2.00 (s, 3H), 1.54 (d, 6H), 1.40–1.00 (m, 4H); API MS m/z=499 $[C_{28}H_{34}N_8O+H]^+$.

Example 65

Preparation of Compound 80

Compound 74 (0.02 g, 0.05 mmol) was dissolved in dry benzene (5 mL) and stirred under a blanket of argon. The solution was cooled in an ice bath and phenylisocyanate (25 L, 0.23 mmol) was added dropwise. The ice bath was removed and the mixture stirred at room temperature for 0.5 h. The solvent was evaporated in vacuo to give a yellow oil. The crude product was purified by flash column chromatography on silica gel to give 80 (0.008 g): $^1$H NMR (300 MHz, $CDCl_3$) δ7.53–7.30 (m, 10H), 7.13–7.06 (m, 4H), 6.98–6.88 (m, 1H), 6.62 (s, 1H), 6.02 (s, 1H), 5.65 (s, 1H), 5.02 (d, 1H), 4.85–4.70 (m, 2H), 4.60–4.52 (m, 1H), 4.45–4.40 (m, 1H), 4.36–4.22 (m, 2H), 4.00 (s, 1H), 1.91–1.60 (m, 6H), 1.48–1.43 (m, 6H).

Example 66

Preparation of Compound 82

A mixture of 6-chloronicotinamide (2.96 g, 18.9 mmol), phenylboronic acid (2.54 g, 20.8 mmol), and $Pd(PPh_3)_4$ (643 mg, 0.565 mmol) in toluene (47 mL), ethanol (7 mL) and 2M aqueous sodium carbonate solution (21 mL, 43 mmol) was stirred and heated at 90–100° C. under nitrogen for 16 h. The mixture was cooled to room temperature and filtered. The resulting solid was washed with water (2×20 mL) and dried in vacuo. To the dried solid was added methanol (50 mL). The mixture was stirred at reflux, cooled to room temperature, and filtered to give the product (90%) as a powder: mp 218–220° C.; $^1$H NMR (500Hz, DMSO-$d_6$) δ9.23 (d, J=2.5 Hz, 1H), 8.41 (dd, $J_1$=2.2 Hz, $J_2$=8.3 Hz, 1H), 8.32 (s, 1H), 8.27 (d, J=7.1 Hz, 2H), 8.20 (d, J=8.5 Hz, 1H), 7.74 (s, 1H), 7.66–7.60 (m, 3H).

Example 67

Preparation of Compound 83

To $NaBH_4$ (0.19 g, 5 mmol) in 1,4-dioxane (4 mL) was added HOAc (0.3 g, 5 mmol) in 1,4-dioxane (2 mL) slowly while the flask was cooled with ice. Compound 82 (0.2 g, 1 mmol) was then added. The mixture was stirred at reflux at 100–110° C. for 4 h and the solvent was evaporated. To this mixture was added water (2 mL) slowly. The mixture was extracted with $CH_2Cl_2$ (4×10 mL), washed with water (3×5 mL), dried with anhydrous sodium sulfate, concentrated, and purified by flash chromatography on silica gel to provide the product as a yellow liquid. This was triturated with ethanol (1 mL) to provide a white solid which was collected (60%) and dried: mp 97–99° C.; $^1$H NMR (500 Hz, $CDCl_3$)

δ 8.60 (d, J=2 Hz, 1H), 7.97–7.95 (m, 2H), 7.72–7.67 (m, 2H), 7.47–7.37 (m, 3H), 3.90 (s, 2H), 1.77 (bs, 2H).

Example 68

Preparation of Compound 84

A mixture of 2,6-dichloropurine (1, 0.19 g, 1 mmol), amine 83 (0.39 g, 2.15 mmol) in ethanol (13 mL), and water (3 mL) was heated at 100–110° C. under nitrogen for 24 h and then cooled to room temperature. The mixture was concentrated and water (5 mL) was added. A solid was filtered and washed with water (2×5 ml) and dried under vacuum to give the product (80%) as a yellow solid: mp 260° C. (dec); $^1$H NMR (500 Hz, DMSO-d$_6$) δ13.26 (s, 1H), 8.79 (s, 1H), 8.27 (s, 1H), 8.16 (d, J=7.1 Hz, 2H), 8.34 (d, J=7.3 Hz, 1H), 7.96 (d, J=7.6Hz, 1H), 7.63–7.52 (m, 3H), 4.81 (s, 2H).

Example 69

Preparation of Compound 85

To a solution of compound 84 (0.34 g, 1 mmol) in DMSO (5 mL). was added potassium carbonate (0.7 g, 5 mmol) and 2-iodopropane (0.5 g, 3 mmol). The mixture was stirred at ambient temperature under nitrogen for 24 h and poured into ice water (30 mL). After filtration, the solid was washed with water (4×5 mL), dried under vacuum to give the crude product as a yellow solid. Flash column chromatography of the crude product on silica gel and recrystallization provided the pure product (63%) as ivory colored crystals: mp 138–139° C.; $^1$H NMR (500 Hz, CDCl$_3$) δ8.70 (d, J=1.5 Hz, 1H), 7.97 (m, 2H), 7.79 (dd, J$_1$=1.7 Hz, J$_2$=8.1 Hz, 1H), 7.71 (s, 1H), 7.69 (d, J=8.1 Hz, 1H), 7.48–7.39 (m, 3H), 4.87 (s, 2H), 4.80 (m, 1H), 1.55 (d, J=6.8 Hz, 6H); CI MS m/z=379 [C$_{20}$H$_{19}$ClN$_6$+H]$^+$. Anal. Calcd. for C$_{20}$H$_{19}$ClN$_6$: C, 63.41; H, 5.05; N, 22.18. Found: C, 63.75; H, 5.09; N, 21.87.

Example 70

Preparation of Compound 86

To compound 85 (0.1 g, 0.26 mmol) was added trans-1,4-diaminocyclohexane (1 g, 8.8 mmol) and EtOH (2 mL). The reaction mixture was heated in a sealed tube in an oil bath at 120° C. The crude product was purified by column chromatography to give 86 (0.08 g, 67%): $^1$H NMR (300 MHz, CDCl$_3$) δ8.68 (d, 1H), 7.83–7.97 (m, 2H), 7.70–7.83 (m, 1H), 7.55–7.73 (m, 1H), 7.30–7.55 (m, 4H), 6.35 (bs, 1H), 4.72–4.95 (m, 2H), 4.50–4.72 (m, 2H), 3.63–3.85 (m, 1H), 2.65–2.90 (m, 1H), 2.37–2.63 (bs, 2H), 1.80–2.20 (dd, 4H), 1.53 (d, 6H), 0.72–1.42 (m, 4H); API MS m/z=457 [C$_{26}$H$_{22}$N$_8$+H]$^+$.

Example 71

Preparation of Compound 87

Compound 86 (0.08 g, 0.18 mmol) was stirred at room temperature in CH$_2$Cl$_2$ (3 mL). Pyridine (100 mg, 0.82 mmol) was added followed by Ac$_2$O (100 mg, 0.98 mmol) and DMAP (few crystals). After 2 h, more CH$_2$Cl$_2$ (3 mL) was added and the mixture was washed carefully with 2N HCl (10 drops), and saturated NaHCO$_3$. After separation of the CH$_2$Cl$_2$ layer, the organic phase was then dried with Na$_2$SO$_4$ and concentrated to give 87 (80 mg, 92%): $^1$H NMR (300 MHz, CDCl$_3$) δ8.72 (s, 1H), 8.30–7.03 (m, 9H), 5.75–5.38 (m, 1H), 5.02 (bs, 1H), 4.83 (bs, 2H), 4.72–4.40 (m, 1H), 3.73 (bs, 2H), 2.52–1.83 (m, 4H), 1.98 (s, 3H), 1.52 (d, 6H), 1.50–1.00 (m, 4H); API MS m/z=499 [C$_{28}$H$_{34}$N$_8$O+H]$^+$.

Example 72

Preparation of Compound 88

Compound 85 (0.05 g, 0.13 mmol) and (R)-(−)-2-amino-1-butanol (0.50 g, 5.6 mmol) were combined in a sealed tube and heated in an oil bath at 190° C. for 2 h then cooled to room temperature. The mixture was partitioned between EtOAc and brine, washed with brine (3×), dried with Na$_2$SO$_4$, and concentrated. The mixture was allowed to stand over the weekend and then purified by column chromatography on SiO$_2$ to give 88 (0.01 g, 17%) as a foam: $^1$H NMR (300 MHz, CDCl$_3$) δ8.70 (s, 1H), 8.05–7.82 (m, 2H), 7.82–7.55 (m, 2H), 7.57–7.30 (m, 4H), 6.55 (bs, 1H), 5.00–4.88 (s, 1H), 4.78 (s, 2H), 4.60 (heptuplet, 1H), 3.98–3.83 (m, 1H), 3.84–3.70 (m, 1H), 3.70–3.50 (m, 1H), 2.90 (bs, 1H), 1.75–1.55 (m, 2H), 1.53 (d, 6H), 1.00 (t, 3H); API MS m/z=432 [C$_{24}$H$_{29}$N$_7$O+H]$^+$.

Example 73

Preparation of Compound 89

A mixture of 6-chloronicotinamide (2.5 g, 16 mmol), crude 2-trimethylstannylpyridine (5.8 g, 24 mmol), and PdCl$_2$(PPh$_3$)$_2$ (560 mg, 0.8 mmol) in DMF (35 mL) was heated at 150–160° C. in a pressure tube for 17 h. The DMF was distilled off under reduced pressure and the residue was extracted with ethyl acetate (6×30 mL) and concentrated. The residue was treated with methanol (15 ml,) and a solid separated which was filtered and dried to give the product (40%) as a powder: mp 237–240° C.; $^1$H NMR (500 Hz, DMSO-d$_6$) 9.22 (d, J=2.2 Hz, 1H), 8.83 (m, 1H) 8.57–8.53 (m, 2H), 8.48–8.46 (m, 1H), 8.38 (s, 1H), 8.11–8.07 (m, 1H), 7.78 (s, 1H), 7.63–7.60 (m, 1H).

Example 74

Preparation of Compound 90

To NaBH$_4$ (0.2 g, 5 mmol) in 1,4-dioxane (4 mL) was added HOAc (0.29 g, 5 mmol) in 1,4-dioxane (2 mL) slowly while the flask was cooled with ice. Compound 89 (0.199 g, 1 mmol) was then added. The mixture was stirred at reflux at 100–110° C. for 4 h and the solvent was evaporated. To this mixture was added water (2 mL) slowly. The mixture was extracted with CH$_2$Cl$_2$ (4×10 mL). washed with water (3×5 mL), dried with anhydrous sodium sulfate, filtered, concentrated, and purified by flash chromatography on silica gel to provide the product as a yellow liquid. This was triturated with ethanol (1 mL) and a white solid (32%) was collected and dried: mp 109–112° C.; $^1$H NMR (500 Hz, CDCl$_3$) δ8.63 (m, 1H), 8.58 (s, 1H), 8.32 (m, 2H), 7.77 (m, 2H), 7.25 (m, 1H), 3.91 (s, 2H), 1.94 (s, 2H).

Example 75

Preparation of Compound 91

A mixture of 2,6-dichloropurine (1, 0.2 g, 1 mmol), compound 90 (0.4 g, 2.2 mmol) in ethanol (13 mL), and water (3 mL) was heated at 100–110° C. under nitrogen for 24 h and then cooled to room temperature. The mixture was concentrated and water (5 mL) was added. A solid was filtered and washed with water (2×5 mL) and dried under vacuum to give the product (83%) as a yellow solid: mp 248° C. (dec); $^1$H NMR (500 Hz, DMSO-d$_6$) δ13.27 (s, 1H), 8.81 (s, 1H), 8.78 (d, J=4.1 Hz, 1H), 8.47 (m, 2H), 8.28 (s, 1H), 8.06–8.01 (m, 2H), 7.50 (m, 1H), 4.84 (s, 2H).

Example 76

Preparation of Compound 92

To the solution of compound 91 (0.35 g, 1 mmol) in DMSO (5 mL), added potassium carbonate (0.68 g, 5 mmol)

and 2-iodopropane (0.49 g, 3 mmol). The mixture was stirred at ambient temperature under nitrogen for 24 h and poured into ice water (30 mL). After filtration, the solid was washed with water (4×5 mL), dried under vacuum to give the crude product as a yellow solid. Flash column chromatography of the crude product on silica gel and recrystallization provided the pure product (64%) as white crystals: mp 150–151° C.; $^1$H NMR (500 Hz, CDCl$_3$) δ8.71 (d, J=1.9 Hz, 1H), 8.67 (m, 1H), 8.38–8.36 (m, 2H), 7.86–7.79 (m, 2H). 7.75 (s, 1H), 7.30 (m, 1H), 4.91 (s, 2H), 4.82 (m, 1H), 1.57 (d, J=6.8 Hz, 6H); CI MS m/z=380 [C$_{19}$H$_{18}$ClN$_7$+H]$^+$. Anal. Calcd. for C$_{19}$H$_{18}$ClN$_7$: C, 60.08; H, 4.78; N, 25.81. Found: C, 59.76; H, 4.72; N, 25.57.

Example 77

Preparation of Compound 93

Compound 92 (150 mg, 0.39 mmol), trans-1,4-diaminocyclohexane (1.50 g, 13.1 mmol), and EtOH (30 mL) were heated to 120° C. for 26 h in a sealed tube. The mixture was cooled, additional EtOAc was added, washed with brine, dried over Na$_2$SO$_4$, and concentrated to give 93 (170 mg, 94%) as a waxy solid: $^1$H NMR (300 MHz, CDCl$_3$) δ8.77–8.60 (m, 1H), 8.44–8.27 (m, 2H), 7.90–7.75 (m, 2H), 7.50 (s, 1H), 7.36–7.22 (m, 2H), 6.27 (bs, 1H), 4.96–4.73 (m, 2H), 4.73–4.52 (m, 2H), 3.84–3.60 (m, 1H), 2.80–2.57 (m, 1H), 2.22–2.00 (m, 2H), 2.00–1.67 (m, 5H), 1.54 (d, 6H), 1.38–1.05 (m, 4H); API MS m/z=458 [C$_{25}$H$_{31}$N$_9$+H]$^+$.

Example 78

Preparation of Compound 94

Compound 93 (0.15 g, 0.33 mmol) was dissolved in CH$_2$Cl$_2$ (6 mL) and then pyridine (0.200 g, 1.64 mmol) followed by Ac$_2$O (0.200 g, 1.96 mmol) and DMAP (few crystals) were added. The reaction mixture was stirred for 2 h, washed with 2N HCl and NaHCO$_3$, extracted with CH$_2$Cl$_2$, dried with Na$_2$SO$_4$, and concentrated to give 94 (0.17 g, 69%) as a solid: mp 141–145° C.; $^1$H NMR (300 MHz, CDCl$_3$) δ8.80–8.63 (m, 1H), 8.45–8.25 (m, 2H), 7.95–7.73 (m, 2H), 7.52 (s, 1H), 7.35–7.20 (m, 2H), 6.20 (bs, 1H), 5.50–5.30 (m, 1H), 4.98–4.75 (m, 2H), 4.75–4.50 (m, 2H), 3.84–3.60 (m, 2H), 2.27–1.87 (m, 4H), 2.00 (s, 3H), 1.52 (d, 6H), 1.40–1.10 (m, 4H); API MS m/z=499 [C$_{27}$H$_{33}$N$_9$O+H]$^+$.

Example 79

Preparation of Compound 95

DME (3 mL), tris(dibenzylideneacetone)dipalladium (0.01 g. 0.0(1 mmol), and PPh$_3$ (0.04 g, 0.15 mmol) were added to a round bottomed flask equipped with a condenser and maintained under an argon atmosphere. To the solution was added compound 11 (0.13 g, 0.25 mmol). 3-Fluorobenzene boronic acid (0.123 g, 0.9 mmol) was dissolved in a solution of 2M Na$_2$CO$_3$ (0.6 mL) and DME (1 mL), and added to the reaction mixture. The mixture was stirred under argon and refluxed for 19 h then stirred at room temperature for 22 h. The reaction mixture was diluted with H$_2$O, extracted with CH$_2$Cl$_2$, washed with brine. The organic layer was dried over Na$_2$SO$_4$ and evaporated. The reaction mixture was purified twice by column chromatography and dried under high vacuum to give a white solid (17 mg, 14%): $^1$H NMR (300 MHz, CDCl$_3$) δ7.56–7.32 (m, 8H), 7.08–6.99 (m, 1H), 5.86 (br, 1H), 4.83 (d, 2H), 4.71–4.56 (m, 1H), 3.77 (br, 2H), 2.70 (br, 1H), 2.12 (d, 1H), 1.88 (d, 1H), 1.51 (d, 6H), 1.22 (d, 5H), 0.94–0.70 (m, 3H); API MS m/z 474 [C$_{27}$H$_{32}$FN$_7$+H]$^+$.

Example 80

Preparation of Compound 96

A stock solution of acetic anhydride was made by mixing CH$_2$Cl$_2$ (16 mL), pyridine (4 mL), and Ac$_2$O (0.16 mL). To this stock solution (1.5 mL) was added compound 95 (0.01 g, 0.02 mmol) followed by DMAP (few crystals). The reaction mixture was allowed to stir at room temperature for 26 h. The reaction mixture was then diluted with CH$_2$Cl$_2$, washed with 2N HCl until the aqueous layer was acidic, washed with NaHCO$_3$, dried over MgSO$_4$, evaporated, and dried in vacuo for 15 h to give a white solid (11 mg, 92%): $^1$H NMR (300 MHz, CDCl$_3$) δ8.65 (br, 1H), 7.77–7.17 (m, 8H), 7.11–6.99 (m, 1H), 5.14 (br, 2H), 4.90 (br, 1H), 4.69 (br, 1H), 3.78 (br, 2H), 2.09 (br, 3H), 1.94 (s, 2H), 1.57 (d, 6H), 1.42 (br, 4H), 1.24 (s, 2H), 0.94–0.76 (m, 1H); CI MS m/z=516 [C$_{29}$H$_{34}$FN$_7$O+H]$^+$.

Example 81

Preparation of Compound 97

A stock solution of acetic anhydride was made by mixing CH$_2$Cl$_2$ (16 mL), pyridine (4 mL), and Ac$_2$O (0.16 mL). To this stock solution (1.5 mL) was added compound 13 (0.01 g, 0.02 mmol) followed by DMAP (few crystals). The reaction mixture was allowed to stir at room temperature for 2 h. The reaction mixture was then diluted with CH$_2$Cl$_2$, washed with 2N HCl until it was acidic, washed with NaHCO$_3$, dried over MgSO$_4$, and evaporated to give a white solid (8 mg, 89%): $^1$H NMR (300 MHz, CDCl$_3$) δ8.78 (d, 1H), 8.44 (t, 1H), 7.95 (t, 2H), 7.69–7.45 (m, 5H), 5.30 (br, 2H), 4.84 (br, 1H), 4.68 (br, 1H), 3.78 (br, 2H). 2.39 (s, 3H), 2.10 (br, 4H), 1.96 (s, 2H), 1.57 (br, 10H), 1.25 (s, 2H), 0.88 (br, 1H); API MS m/z=512 [C$_{30}$H$_{37}$N$_7$O+H]$^+$.

Example 82

Preparation of Compound 98

DME (3 mL), tris(dibenzylideneacetone)dipalladium (0.01 g, 0.01 mmol), and PPh$_3$ (0.04 g, 0.15 mmol) were added to a round bottom flask equipped with condensor and maintained under an argon atmosphere. Iodide 11 (0.13 g, 0.26 mmol), and 3-chlorobenzene boronic acid (0.15 g, 0.93 mmol) was dissolved in 2M Na$_2$CO$_3$ (0.6 mL) and DME (1 mL). This was then added to the reaction mixture and refluxed for 19.5 h then stirred at room temperature for 30 h. The reaction mixture was then diluted with H$_2$O, extracted with CH$_2$Cl$_2$, washed with brine, dried over Na$_2$SO$_4$, filtered, and evaporated. The reaction mixture was purified by column chromatography (3×) and evaporated. The product was triturated in hexanes. filtered, and dried in vacuo for 1 h to give a white solid (16 mg): $^1$H NMR (300 MHz, CDCl$_3$) δ7.56–7.38 (m, 9H), 6.01 (br, 1H), 4.80 (d, 2H), 4.71–4.62 (m, 1H), 3.77 (br, 2H), 2.73 (br, 1H), 2.19–2.04 (m, 1H), 1.94–1.85 (m, 1H), 1.51 (d, 6H), 1.24 (d, 5H), 0.91–1.76 (m, 3H); API MS m/z=490 [C$_{27}$H$_{32}$ClN$_7$+H]$^+$.

Example 83

Preparation of Compound 99

A stock solution of acetic anhydride was made by mixing CH$_2$Cl$_2$ (16 mL), pyridine (4 mL), and Ac$_2$O (0.16 mL). To this solution (1.5 mL) was added compound 98 (0.01 g, 0.02 mmol), followed by DMAP (few crystals). The reaction mixture was allowed to stir at room temperature for 2 h. The reaction mixture was diluted with CH$_2$Cl$_2$, washed with 2N HCl until the aqueous layer was acidic, washed with NaHCO$_3$, dried over MgSO$_4$, filtered, and evaporated to give a white solid (0.01 g, 83%): $^1$H NMR (300 MHz, CDCl$_3$) δ7.65–7.35 (m, 8H), 7.26–7.14 (m, 1H), 5.23 (br, 1H), 4.66 (br, 1H), 3.78 (br, 2H), 2.18–2.00 (m, 4H), 1.94 (s, 3H), 1.54 (d, 6H), 1.24 (s, 5H), 0.94–0.69 (m, 3H); API MS m/z=532 [C$_{29}$H$_{34}$ClN$_7$O+H]$^+$.

Example 84

Preparation of Compound 100

A stock solution of acetic anhydride was made by mixing CH$_2$Cl$_2$ (16 mL), pyridine (4 mL), and Ac$_2$O (0.16 mL). To compound 14 (0.02 g, 0.03 mmol) was added this solution (2 mL), followed by DMAP (few crystals). The reaction mixture was allowed to stir at room temperature for 3 h. The reaction mixture was diluted with $CH_2Cl_2$, washed with 2N HCl until the aqueous layer was acidic, washed with $NaHCO_3$, filtered, and evaporated to give a white solid (8 mg, 44%): $^1$H NMR (300 MHz, $CDCl_3$) δ7.41–7.32 (m, 7H), 7.26–7.14 (m, 1H), 5.96 (br, 1H), 5.23 (d, 1H), 4.84 (br, 2H), 4.69–4.54 (m, 1H), 3.75 (br, 1H), 2.21–2.12 (m, 1H), 2.09–1.96 (m, 1H), 1.97 (s, 3H), 1.54 (d, 6H), 1.36–1.15 (m, 5H), 0.85 (br, 3H); API MS m/z=550 $[C_{29}H_{33}ClFN_7O+H]^+$.

Example 85

Preparation of Compound 101

DME (3 mL), tris(dibenzylideneacetone)dipalladium (0.01 g, 0.01 mmol), and $PPh_3$ (0.04 g, 0.15 mmol) were added to a round bottomed flask equipped with a condenser and maintained under an argon atmosphere. Compound 10 (0.13 g, 0.26 mmol) and 4-fluorobenzene boronic acid (0.13 g, 0.95 mmol) was dissolved in 2M $Na_2CO_3$ (0.6 mL) and DME (1 mL). This was then added to the reaction mixture and refluxed for 19 h then stirred at room temperature for 72 h. The reaction mixture was then diluted with $H_2O$, extracted with $CH_2Cl_2$, washed with brine, dried over $Na_2SO_4$, filtered, and evaporated. The reaction mixture was purified by column chromatography on silica gel to give a white solid (17 mg, 14%): $^1$H NMR (300 MHz, $CDCl_3$) δ7.56–7.38 (m, 8H), 7.11 (t, 1H), 5.81 (br, 1H), 4.81 (d, 2H), 4.69–4.57 (m, 1H), 3.78 (br, 2H), 2.69 (br, 1H), 2.12 (br, 1H), 1.88 (br, 1H), 1.54 (d, 6H), 1.33–1.12 (m, 5H), 0.85 (br, 3H); API MS m/z=474 $[C_{27}H_{32}FN_7+H]^+$.

Example 86

Preparation of Compound 102

A stock solution of acetic anhydride was made by mixing $CH_2Cl_2$ (16 mL), pyridine (4 mL), and $Ac_2O$ (0.16 mL). To the solution (1.4 mL) was added compound 101 (0.01 g, 0.02 mmol), followed by DMAP (few crystals). The reaction mixture was allowed to stir at room temperature for 2.5 h. The reaction mixture was diluted with $CH_2Cl_2$, washed with 2N HCl until the aqueous layer was acidic, and washed with saturated $NaHCO_3$. The organic layer was dried over $MgSO_4$ and evaporated to give a product (3 mg). The $NaHCO_3$ layer was further extracted with EtOAc (2×), the organic layers were combined, dried over $MgSO_4$, evaporated to give product 102 (2 mg). The products were combined using EtOAc, evaporated, and dried in vacuo for 15 h to give product 102 (5 mg, 50%): $^1$H NMR (300 MHz, $CDCl_3$) δ7.71–7.08 (m, 9H), 5.29 (br, 2H), 4.84 (br, 1H), 4.66 (br, 1H), 3.78 (br, 2H), 2.09 (br, 4H), 1.97 (s, 1H), 1.57 (br, 3H), 1.24 (d, 6H), 0.87 (br, 5H); API MS m/z=516 $[C_{29}H_{34}FN_7O+H]^+$.

Example 87

Preparation of Compound 103

Compound 30 (0.10 g, 0.27 mmol) and trans-1,4-diaminocyclohexane (0.48 g, 4.2 mmol) were combined with EtOH (2 mL) in a sealed tube and heated at 190° C. for 24 h, and then stirred at room temperature for 46 h. The reaction mixture was purified by column chromatography and dried in vacuo to give 103 as a white solid (0.10 g, 81%): $^1$H NMR (300 MHz, $CDCl_3$) δ8.83 (d, 1H), 8.58 (t, 1H), 7.87–7.83 (m, 1H), 7.55–7.47 (m, 5H), 7.38–7.33 (m, 1H), 5.96 (br, 1H), 4.82 (d, 2H), 4.68–4.59 (m, 1H), 3.75 (br, 2H), 2.69 (br, 1H), 2.14 (d, 2H), 1.86 (d, 2H), 1.54 (d, 6H), 1.31–1.18 (m, 5H); API MS m/z=457 $[C_{26}H_{32}N_8+H]^+$.

Example 88

Preparation of Compound 104

A stock solution of acetic anhydride was made by mixing $CH_2Cl_2$ (16 mL), pyridine (4 mL), and $Ac_2O$ (0.16 mL). To the solution (3.1 mL) was added compound 103 (0.02 g, 0.04 mmol), followed by DMAP (few crystals). The reaction mixture was allowed to stir at room temperature for 2.5 h. The reaction mixture was evaporated, dried in vacuo for 19 h, and purified by column chromatography to give a white solid (0.02 g): $^1$H NMR (300 MHz, $CDCl_3$) δ8.83 (d, 1H), 8.59 (t, 1H), 7.85 (d, 1H), 7.55–7.47 (m, 5H), 7.38–7.34 (m, 1H), 5.89 (br, 1H), 5.25 (d, 2H), 4.85 (br, 1H), 4.66–4.61 (m, 1H), 3.77 (br, 2H), 2.15 (br, 2H), 2.05 (br, 2H), 1.97 (s, 2H), 1.54 (d, 6H), 1.33–1.25 (m, 5H), 0.88 (br, 1H); API MS m/z=499 $[C_{28}H_{34}N_8O+H]^+$.

Example 89

Preparation of Compound 106

Compound 72 (0.30 g, 0.80 mmol) and compound 105 (1.15 g, 6.50 mmol) (Gardiner, J. M., et al. *Tetrahedron*, 42(11):515 (1995), which is hereby incorporated by reference, were combined with EtOH (7 mL) and allowed to reflux for 23 h. Triethylamine (1 mL) was added and the reaction was refluxed further for another 21 h. The reaction mixture was then transferred to a sealed tube and EtOH (3 mL) was added. The reaction mixture was heated further at 100° C. for 3 h. The mixture was purified by column chromatography to give 105 (0.13 g): $^1$H NMR (300 MHz, $CDCl_3$) δ7.57–7.26 (m, 10H) 5.58 (br, 1H), 5.10 (br, 1H), 4.83 (br, 1H), 4.69–4.62 (m, 2H), 3.36–2.91 (m, 5H), 2.82–2.65 (m, 2H), 1.53 (d, 2H), 1.44 (s, 9H), 1.25 (d, 1H), 1.13 (d, 3H); CI MS m/z=416 $[C_{29}H_{39}N_7O-Boc+H]^+$.

Example 90

Preparation of Compound 107

To compound 106 (0.10 g, 0.18 mmol) was added $Et_2O$ (2 mL). $CH_2Cl_2$ (1 mL) and MeOH (1 mL). During 16 h HCl/ether (1M, 5 mL) was added while stirring. The resulting precipitate was collected by filtration and dried in vacuo for 30 min to provide 106 as an off-white solid (60 mg, 81%): $^1$H NMR (300 MHz, DMSO) δ8.48 (br, 2H), 8.15 (br, 1H), 7.67–7.27 (m, 10H), 4.79 (br, 1H), 3.60–3.42 (m, 3H), 3.18–3.06 (m, 2H), 3.03–2.91 (m, 2H), 1.52 (d, 2H), 1.27 (d, 6H); CI MS m/z=416 $[C_{24}H_{29}N_7+H]^+$.

Example 91

Preparation of Compound 108

A stock solution of acetic anhydride was made by mixing $CH_2Cl_2$ (16 mL), pyridine (4 mL), and $Ac_2O$ (0.16 mL). To this solution (5.6 mL) was added compound 107 (0.04 g, 0.09 mmol), followed by DMAP (few crystals). The reaction mixture was allowed to stir at room temperature for 2 h. The reaction mixture was diluted with $CH_2Cl_2$, washed with 2N HCl until acidic, the organic layer was washed with $NaHCO_3$, dried over $MgSO_4$, filtered, and evaporated to give a white solid (1 6 mg). The product was purified by column chromatography to provide 108 as a white solid (0.01 g, 18%): $^1$H NMR (300 MHz, $CDCl_3$) δ7.58–7.43 (m, 10H), 6.60 (br, 1H), 5.91 (br, 1H), 5.04 (t, 1H), 4.84 (br, 2H), 4.72–4.59 (m, 1H), 4.10–4.02 (m, 1H), 3.59–3.47 (m, 2H), 1.80 (s, 3H), 1.57 (d, 6H), 1.19 (d, 3H); CI MS m/z=458 $[C_{26}H_{31}N_7O+H]^+$.

Example 92

Preparation of Compound 109

Compound 61 (1.0 g, 2.18 mmol), 3-chlorophenylboronic acid (1.3 g, 8.16 mmol), $PPh_3$ (0.3 g, 1.26 mmol), 2M Na₂CO₃ (5.0 mL), and DME (54 mL) were added to a three-necked round-bottomed flask. The mixture was degassed with argon and heated to reflux for 40 min, cooled to room temperature, and then Pd$_2$(dba)$_3$ (0.08 g, 0.08 mmol) was added. The reaction mixture was heated at reflux for 7 h. 3-Chlorophenylboronic acid (0.6 g) and Pd$_2$(dba)$_3$ (0.08 g) was then added and reflux continued for 12 h. The reaction mixture was cooled to room temperature, diluted with H₂O (50 mL), and extracted with CH₂Cl₂ (3×50 mL). The combined organic phases were washed with H₂O (50 mL), brine (50 mL), dried over Na₂SO₄, filtered, and concentrated in vacuo. The residue was purified by silica gel chromatography and concentrated in vacuo to obtain compound 109 (950 mg, 89%): mp 178–181° C.; ¹H NMR (500 MHz, CDCl₃) δ7.56 (s, 1H), 7.42–7.54 (m, 6H), 7.26–7.35 (m, 2H), 6.08 (bs, 1H), 4.81 (bs, 2H), 4.59–4.64 (m, 2H), 3.75–3.81 (m, 1H), 2.65–2.72 (m, 1H), 2.12 (d, 2H), 1.88 (d, 2H), 1.53 (d, 6H), 1.18–1.27 (m, 4H); CI MS m/z=490 [C$_{27}$H$_{32}$ClN$_7$+H]⁺.

Example 93

Preparation of Compound 110

Compound 109 (500 mg, 1.02 mmol) was dissolved in anhydrous CH₂Cl₂ (30 mL), cooled with an ice-water bath, followed by the addition of DMAP (12.2 mg, 0.1 mmol), pyridine (124 μL, 1.53 mmol), and Ac₂O (106 μL, 1.12 mmol). The reaction mixture was stirred for 30 min at 0° C. an ice-water bath then stirred another 2 h at room temperature. The reaction mixture was then concentrated in vacuo and the residue was purified by column chromatography on silica gel. After removal of the solvent, the residue was dried in vacuo to give 110 (339 mg, 63%): mp 198–200° C.; ¹H NMR (500 MHz, CDCl₃) δ7.57 (s, 1H), 7.39–7.53 (m, 6H), 7.27–7.37 (m, 2H), 6.31 (bs, 1H), 5.28 (d, 1H), 4.78 (bs, 2H), 4.70 (d, 1H), 4.58–4.67 (m, 1H), 3.72–3.83 (m, 1H), 2.18 (d, 2H), 2.00 (d, 2H), 1.90 (s, 3H), 1.51 (d, 6H), 1.18–1.31 (m, 4H); CI MS m/z=532 [C$_{29}$H$_{34}$ClN$_7$O+H]⁺.

Example 94

Preparation of Compound 111

Compound 61 (1.0 g, 2.18 mmol), 2-thiopheneboronic acid (1.0 g, 8.16 mmol), PPh₃ (0.3 g, 1.26 mmol), 2M Na₂CO₃ (5.0 mL), Pd$_2$(dba)$_3$ (0.08 g, 0.08 mmol), and DME (54 mL) were added to a round-bottomed flask and purged with argon. The reaction mixture was heated at reflux for 24 h. 2-Thiopheneboronic acid (0.5 g), Pd$_2$(dba)$_3$ (0.1 g), and 2M Na₂CO₃ (2 mL) were added and heated to reflux for another 24 h. The reaction mixture was cooled to room temperature, diluted with H₂O (50 mL) and extracted with CH₂Cl₂ (3×50 mL). The organic phase was washed with H₂O (50 mL) and brine (50 mL), dried over Na₂SO₄, filtered, and concentrated in vacuo. The residue was repeatedly chromatographed on silica gel to obtain 111 (574 mg, 59%): mp 109–110° C.; ¹H NMR (500 MHz, CDCl₃) δ7.56 (d, 2H), 7.54 (s, 1H), 7.46 (d, 2H), 7.24–7.37 (m, 2H), 7.06 (t, 1H), 6.04 (bs, 1H), 4.78 (bs, 2H), 4.59–4.69 (m, 2H), 3.75–3.81 (m, 1H), 2.67–2.74 (m, 1H), 2.14 (d, 2H), 1.87 (d, 2H), 1.52 (d, 6H), 1.17–1.29 (m, 4H); CI MS m/z=462 [C$_{25}$H$_{31}$N$_7$S+H]⁺.

Example 95

Preparation of Compound 112

Compound 111 (410.0 mg, 0.89 mmol) was dissolved in anhydrous CH₂Cl₂ (30 mL) and purged with N₂ and cooled with an ice-water bath. Pyridine (108 mg, 1.34 mmol) and DMAP (10.9 mg, 0.09 mmol) followed by Ac₂O (92 μL, 0.98 mmol) were added slowly. The reaction mixture was stirred for 30 min in an ice-water bath followed by 2 h at room temperature. The reaction mixture was concentrated in vacuo. The residue was chromatographed on silica gel to give 112 (325 mg, 73%): mp 237–244° C.; ¹H NMR (500 MHz, CDCl₃) δ7.54 (d, 2H), 7.50 (s, 1H), 7.36 (d, 2H), 7.24–7.37 (m, 2H), 7.08 (t, 1H), 6.06 (bs, 1H), 5.34 (s, 1H), 4.78 (bs, 2H), 4.58–4.70 (m, 2H), 3.78 (bs, 2H), 2.17 (d, 2H), 2.04 (d, 2H), 1.96 (s, 3H), 1.56 (d, 6H), 1.18–1.32 (m, 4H); CI MS m/z=504 [C$_{27}$H$_{33}$N$_7$OS+H]⁺.

Example 96

Preparation of Compound 113

Compound 12 (600 mg, 1.30 mmol) was dissolved in anhydrous CH₂Cl₂ (40 mL), purged with N₂, and cooled to 0° C. followed by an addition of DMAP (15.9 mg, 0.13 mmol), pyridine (165.3 mg, 1.95 mmol), and Ac₂O (135 mg, 1.43 mmol). The mixture was stirred 30 min at 0° C. then 2 h at room temperature. The reaction mixture was concentrated in vacuo. The residue was chromatographed on silica gel to give 113 (495 mg, 76%): mp 248–253° C.; ¹H NMR (500 MHz, CDCl₃) δ7.54 (d, 2H), 7.46 (s, 1H), 7.35–7.41 (m, 5H), 6.13 (bs, 1H), 5.28 (d, 1H), 4.78 (br, 2H), 4.61–4.63 (m, 2H), 3.75 (bs, 2H), 2.14 (d, 2H), 1.97 (d, 2H), 1.95 (s, 3H), 1.52 (d, 6H), 1.15–1.37 (m, 4H); CI MS m/z 504 [C$_{27}$H$_{33}$N$_7$OS+H]⁺.

Example 97

Preparation of Compound 114

To compound 61 (1.0 g, 2.18 mmol) was added PPh₃ (330 mg, 1.26 mmol), 2M Na₂CO₃ (5 mL), DME (54 mL), and 4-carboxyphenylboronic acid (1.0 g, 6.03 mmol). The mixture was purged with N₂ for 45 min then Pd$_2$(dba)$_3$ (366 mg, 0.4 mmol) was added and the mixture was heated at reflux for 3 d. The reaction mixture was diluted with H₂O (100 mL). The aqueous layer was separated, and washed with CH₂Cl₂ (3×40 mL). The aqueous layer was adjusted the pH to 5.8 by using 1N HCl. Some precipitate appeared. The mixture was stored in a freezer overnight. The precipitate was collected and dried to obtain 114 (450 mg, 41%): mp 246–249° C. (dec.); ¹H NMR (500 MHz, CD₃OD+NaOD) δ7.84 (s, 2H), 7.64 (s, 1H), 7.54–7.63 (m, 4H), 7.39 (s, 2H), 6.08 (bs, 1H), 4.85 (bs, 2H), 4.73 (s, 1H), 3.76 (m, 1H), 2.74 (m, 1H), 1.99 (s, 2H), 1.88 (s, 2H), 1.63 (d, 6H), 1.21–1.36 (m, 4H); CI MS m/z=500 [C$_{28}$H$_{33}$N$_7$O$_2$+H]⁺.

Example 98

Preparation of Compound 115

To a cooled MeOH (20 mL) solution was slowly added TMSCl (253 μL, 2.0 mmol). The solution was stirred 20 min, followed by the addition of 114(100 mg, 0.2 mmol). The reaction mixture was stirred at room temperature for 24 h. The reaction mixture was cooled with an ice-water bath then Et₃N (557 mL) was added. The mixture was concentrated in vacuo, to provide the crude product, which was washed with water (2×20 mL). The residue was purified by chromatography on a silica gel. After removal of the solvent and drying in vacuo, the residue was dissolved in MeOH (5 mL), followed by the addition of ether (10 mL). The precipitate was collected and dried to provide 115 (75 mg, 73%): mp194–197° C.; ¹H NMR (500 MHz, CD₃OD) δ8.07 (d, 2H), 7.80 (s, 1H), 7.72 (d, 2H), 7.63 (d, 2H), 7.46 (d, 2H), 4.63–4.79 (m, 1H), 3.91 (s, 3H), 3.65–3.77 (m, 1H), 3.07 (bs, 1H), 2.12 (d, 2H), 2.01 (d, 2H), 1.55 (d, 6H), 1.29–1.49 (m, 4H); API MS m/z=514 [C$_{29}$H$_{35}$N$_7$O$_2$+H]⁺.

Example 99

Preparation of Compound 117

To a suspension of compound 114 (250 mg, 0.50 mmol), pyridine (60 μL, 0.75 mmol), and DMAP (6.1 mg, 0.05 mmol) in H$_2$O-dioxane (2:1, 40 mL) was added Ac$_2$O (57 μL, 0.60 mmol). After stirring 4 h at room temperature, K$_2$CO$_3$ (100 mg) was added followed by additional Ac$_2$O (100 μL). The reaction mixture was stirred 2 h at room temperature. Water (50 mL) was added and the pH was adjusted to 5. The precipitate was collected, washed with water and ether, and dried in vacuo. The precipitate (200 mg) was added to a solution of TMSCl (500 μL, 3.94 mmol) in MeOH (25 mL). The reaction mixture was stirred 24 h at room temperature. The mixture was concentrated in vacuo. The product was purified by silical gel chromatography to provide 117 (145 mg, 52%): mp 247–250° C.; $^1$H NMR (500 MHz, CDCl$_3$) δ8.09 (d, 2H), 7.64 (d, 2H), 7.58 (d, 2H), 7.49 (s, 1H), 7.45 (d, 2H), 5.91 (bs, 1H), 5.18 (d, 1H), 4.83 (bs, 2H), 4.61–4.68 (m, 2H), 3.93 (s, 3H), 3.67–3.78 (m, 2H), 3.07 (bs, 1H), 2.16 (d, 2 1–1), 2.02 (d, 2H), 1.95 (s, 3H), 1.54 (d, 6H), 1.23–1.32 (m, 4H); API MS m/z=556 [C$_{31}$H$_{37}$N$_7$O$_3$+H]$^+$.

Example 100

Preparation of Compound 116

To a solution of compound 117 (90 mg, 0.16 mmol) in MeOH-H$_2$O (6:1, 23 mL) was added KOH (11 mg, 0.19 mmol) in 5 mL MeOH. The reaction mixture was refluxed for 24 h. After removal of the solvent the residue was dissolved in 15 mL of water and washed with CH$_2$Cl$_2$. The aqueous layer was separated and adjusted pH to 4.5 by using 1N HCl. The precipitate was collected and dried to obtain 116 (60 mg, 68%): mp 344–347° C.; $^1$H NMR (500 MHz, DMSO-d$_6$) δ11.21 (bs, 1H), 8.14 (d, 2H), 7.64–7.88 (m, 6H), 7.47 (d, 2H), 6.06 (bs, 1H), 5.18 (d, 1H), 4.85 (bs, 2H), 4.51–4.66 (m, 1H), 3.62 (bs, 1H), 3.46 (bs, 1H), 1.89 (bs, 2H), 1.77 (bs, 5H), 1.95 (s, 3H), 1.47 (d, 6H), 1.23–1.36 (m, 4H); API MS m/z=542 [C$_{30}$H$_{35}$N$_{73}$O+H]$^+$.

Example 101

Preparation of Compound 118

Compound 61 (1.0 g, 2.18 mmol), 3-carboxyphenylboronic acid (1.0 g, 6.03 mmol), 2N Na$_2$CO$_3$ (5 mL), and DME/EtOH (50 mL) were mixed together and degassed with N$_2$ for 1 h. Pd$_2$(dba)$_3$ (366.0 mg, 0.4 mmol) and PPh$_3$ (330.0 mg, 1.26 mmol) were added and the reaction mixture was heated to reflux for 48 h. The reaction mixture was cooled to room temperature, diluted with CH$_2$Cl$_2$ (50 mL), and extracted with aqueous 5% Na$_2$CO$_3$ (3×30 mL). The combined washes were extracted with CH$_2$Cl$_2$ (3×30 mL) and ether (40 mL). The aqueous phase was neutralized to a pH of 5.8 using 1N HCl and kept in a freezer for 1 h. The precipitate was collected, suspended in MeOH (30 mL) and the insolubles were removed by filtration. To the MeOH solution was added ether (20 mL) to precipitate the product. The white solid was collected and dried in vacuo to offer 118 (65 mg, 6%): mp 205–208° C.; $^1$H NMR (500 MHz, CD$_3$OD+NaOD) δ8.17 (s, 1H), 7.88 (d, 1H), 7.80 (s, 1H), 7.56–7.63 (m, 3H), 7.35–7.41 (m, 3H), 6.08 (bs, 1H), 4.80 (bs, 2H), 4.59–4.75 (m, 1H), 3.72–3.82 (m, 1H), 2.89–3.01 (m, 1H), 1.90–1.99 (m, 4H), 1.51 (d, 6H), 1.29–1.40 (m, 2H), 1.12–1.23 (m, 2H); API MS m/z= 500 [C$_{28}$H$_{33}$N$_7$O$_2$+H]$^+$.

Example 102

Preparation of Compound 119

3-Thiopheneboronic acid (4.5 g, 35.2 mmol) and 6-chloronicotinamide (5.0 g, 32.0 mmol) were dissolved in DMA (150 mL), followed by the addition of 2N Na$_2$CO$_3$ (23 mL). N$_2$ gas was passed through the mixture for 1 h. Pd(PPh$_3$)$_4$ (0.74 g, 0.64 mmol) was added and the reaction mixture was heated to reflux for 24 h. The reaction mixture was cooled to room temperature and poured into an ice-water (1 L) and stirred for 10 min. The precipitate was collected and washed with acetone. The collected solid was suspended in EtOAc (150 mL) and heated to reflux for 5 min. The solid was filtered and collected. After drying in vacuo, 119 (4.5 g, 69%) was obtained: $^1$H NMR (500 MHz, DMSO-d$_6$) δ9.08 (s, 1H), 8.34 (s, 1H), 8.28 (d, 1H), 8.20 (bs, 1H), 7.99 (d, 1H), 7.81 (d, 1H), 7.71 (d, 1H), 7.60 (bs, 1H).

Example 103

Preparation of Compound 120

To compound 119 (4.08 g, 20.0 mmol) suspended in THF (50 mL), was added 1M BH$_3$-THF (164 mL). The mixture was heated to reflux for 9 h. The mixture was cooled with an ice-water bath and adjusted to a pH of 1–2, and stirred for 1 h at room temperature. The pH was adjusted to 9–10 (2N NaOH) and extracted with EtOAc (3×50 mL). The combined organic phases were washed with H$_2$O (50 mL), brine (50 mL), and dried over Na$_2$SO$_4$. After filtration and removal of the solvent, the residue was dissolved in EtOH (50 mL), followed by the addition of 1 M HCl/ether (20 mL). The mixture was concentrated to dryness to provide 120 (2.03 g, 45%): $^1$H NMR (500 MHz, CD$_3$OD) δ8.93 (s, 1H), 8.61 (d, 1H), 8.51 (s, 1H), 8.43 (d, 1H), 7.81 (d, 1H), 7.70 (d, 1H), 3.30 (t, 2H).

Example 104

Preparation of Compound 121

Compound 120 (2 g, 8.82 mmol), 2,6-dichloropurine (1.5 g, 8.01 mmol), EtOH (50 mL), and (i-Pr)$_2$NEt (3.8 mL, 22 mmol) were heated at reflux for 16 h. The reaction mixture was then cooled with an ice-water bath. The precipitate was collected and washed with EtOH, H$_2$O, and ether. The precipitate was dried in vacuo to obtain 121 (0.84 g, 31%): $^1$H NMR (500 MHz, DMSO-d$_6$) δ11.02 (bs, 1H), 8.76 (bs, 1H), 8.63 (s, 1H), 8.07 (bs, 2H), 7.79 (bs, 2H), 7.71 (d, 1H), 7.64 (d, 1H), 4.68 (bs, 2H).

Example 105

Preparation of Compound 122

Compound 121 (950 mg, 2.77 mmol) was dissolved in DMSO (50 mL), and then K$_2$CO$_3$ (2.07 g, 15.0 mmol) was added, followed by the addition of 2-iodopropane (830 L, 8.31 mmol). The reaction mixture then was stirred at room temperature overnight. The reaction mixture was poured into an ice-water bath (400 mL), stirred for 10 min, and extracted with EtOAc (4×50 mL). The combined organic phases were washed with H$_2$O (40 mL), brine (40 mL), and dried over MgSO$_4$. After filtration and removal of the solvent, the residue was dissolved in hot EtOAc (40 mL), followed by the addition of hexanes (80 mL). The precipitate was collected and dried in vacuo to obtain 122 (798 mg, 90%): $^1$H NMR (500 MHz, CDCl$_3$) δ8.64 (s, 1H), 7.83 (s, 1H), 7.70–7.79 (m, 2H), 7.60 (d, 1H), 7.55 (d, 1H), 7.36 (d, 1H), 6.11 (bs, 1H), 4.77–4.96 (m, 3H), 1.53 (d, 6H).

Example 106

Preparation of Compound 123

Compound 122 (780.0 mg, 2.03 mmol), trans-1,4-diaminocyclohexane (2.3 g, 20.3 mmol), and EtOH (4 mL) were heated in a sealed tube to 150° C. for 20 h. The reaction mixture was poured into ice-water (150 mL) and stirred for 10 min. The resulting precipitate was washed with H$_2$O (2×20 mL) and dried. The solid was chromatographed on a silica gel column. After removal of the solvent and drying in vacuo, 123 (765 mg) was obtained: mp 78–81° C.; $^1$H NMR (500 MHz, CDCl$_3$) δ8.63 (s, 1H), 7.87 (s, 1H), 7.72 (d, 1H), 7.64 (d, 1H), 7.55 (d, 1H), 7.04–7.09 (m, 1H), 6.92 (s, 1H), 5.95 (bs, 1H), 4.64 (bs, 2H), 4.33–4.45 (m, 2H), 3.74–3.77 (m, 1H), 2.67–2.76 (m, 1H), 2.13 (d, 2H), 1.90 (d, 2H), 1.63 (bs, 2H), 1.54 (d, 6H), 1.19–1.30 (m, 4H); $^{13}$C NMR (CDCl$_3$) δ159.1, 155.0, 152.7, 151.3, 149.3, 143.3, 142.3, 136.2, 134.8, 133.4, 126.4, 126.4, 123.5, 120.2, 114.8, 50.4, 50.3, 46.5, 42.0, 35.7, 32.3, 22.8; API MS m/z=463 [C$_{24}$H$_{30}$N$_8$S+H]$^+$.

Example 107

Preparation of Compound 124

To an ice-cold solution of compound 123 (420 mg, 0.91 mmol) in CH$_2$Cl$_2$ (20 mL) was added pyridine (110 μL, 1.4 mmol), DMAP (11.0 mg, 0.09 mmol) and Ac$_2$O (94.2 μL, 1 mmol). The reaction mixture was stirred for 30 min at 0° C., followed by 2 h at room temperature. After removal of the solvent, the residue was chromatographed on a silica gel column. The resulting solid was recrystallized with EtOAc/MeOH and dried in vacuo to give 124 (350 mg, 79%): mp 249–252° C.; $^1$H NMR (500 MHz, CDCl$_3$) δ8.61 (s, 1H), 7.85 (s, 1H), 7.70 (d, 1H), 7.62 (d, 1H), 7.53 (d, 1H), 7.48 (s, 1H), 7.38 (d, 1H), 6.00 (bs, 1H), 5.25 (d, 1H), 4.77 (bs, 2H), 4.53–4.72 (m, 2H), 3.68–3.77 (m, 2H), 2.10 (d, 2H), 2.00 (d, 2H), 1.94 (s, 3H), 1.52 (d, 6H), 1.17–1.28 (m, 4H); $^{13}$C NMR (CDCl$_3$) δ169.4,159.0, 155.0, 152.8, 149.2, 142.8, 142.3, 136.1, 134.9, 133.4, 126.5, 126.4, 123.5, 120.2,114.9, 50.1, 48.3, 46.5, 42.2, 32.2, 32.1, 22.8; API MS m/z=505 [C$_{26}$H$_{32}$N$_8$OS+H]$^+$.

Example 108

Description of Biological Assays

A. Immunopurification of CyclinA/cdk2 and CyclinE/cdk2 Complexes

CyclinA/cdk2 and cyclinE/cdk2 assays were carried out with cyclin/cdk complexes isolated from HeLa S-3 suspension cultures, HeLa cells were grown in spinner flasks at 37° C. in Joklik's modified minimum essential media (MEM) supplemented with 7% horse serum. After growing in medium supplemented with 2 mM thymidine for 16–18 h, cultures were arrested at the G1/S border and cyclinA/cdk2 and cyclinE/cdk2 were isolated from cell lysates by immunoprecipitation with antibodies specifically directed against each cyclin subunit. Rabbit anti-cyclinA (H-432) and the mouse monoclonal antibody against cyclinE (HE111) were purchased from Santa Cruz Biotechnology. Cells blocked at the appropriate stage of the cell cycle were disrupted in lysis buffer (50 mM Tris, pH 8.0, 250 mM NaCl, 0.5% NP-40 plus protease and phosphatase inhibitors) and centrifuged at 10,000×g to remove insoluble material. To isolate cyclin/cdk complexes, 1 μg of anti-cyclin antibody was incubated with lysate from 1×10$^7$ cells for 1 h at 4° C. Protein A-coated agarose beads were then added for 1 h to collect antibody-bound immune complexes. The immobilized cyclin/cdk complexes were then washed 4× with lysis buffer to reduce nonspecific protein binding. The complexes were then washed 1× in kinase assay buffer (50 mM Tris-HCl, pH 7.4, 10 mM MgCl$_2$, 1 mM DTT) and aliquoted into individual assay tubes.

B. Immunopurification of CyclinB/cdkl Complex

HeLa cells are blocked at the G1/S border by culturing in the presence of 2 mM thymidine for 20 h. The cells are then rinsed 3×in phosphate buffered saline and resuspended in regular medium. After 4 h of culture, the mitotic blocker, nocodazole is added to a final concentration of 75 ng/ml. Sixteen hours later. the cells are harvested by centrifugation, washed in PBS, and lysed in cold Lysis Buffer (50 mM Tris pH 8.0, 250 mM NaCl, 0.5% NP-40, 1 mM DTT, 25 μg/ml leupeptin, 25 μg/ml aprotinin, 15 μg/ml benzamidine, 1 mM PMSF, 50 mM sodium fluoride, 1 mM sodium orthovanadate) for 15 min at 1×10$^7$ cells/ml. The lysate is then clarified by centrifugation at 10,000×g for 10 min. The supernatant is collected and diluted 1:5 with Lysis Buffer. Monoclonal antibody against cyclinB (GNS1) is added to the supernatant to a final concentration of 5 μg/ml and shaken at 4° C. for 2 h. The immune complexes are then collected by the addition of 200 μl of protein agarose beads for 1 h. The beads are washed 4× in lysis buffer and 1× in kinase assay buffer.

C. Protein Kinase Assays and Determination of IC$_{50}$ Values

CyclinA/cdk2 assays were carried out with complexes isolated from 0.5×10$^6$ cells. CyclinE/cdk2 assays were carried out with complexes isolated from 4×10$^6$ cells. CyclinB/cdkl assays were carried out with complexes isolated from 4×10$^4$ cells. After centrifugation, the wash buffer was removed and the complexes resuspended in 15 μl of kinase assay buffer (kinase wash buffer+167 μg/ml histone H1). Compounds being tested for inhibition were added prior to the addition of [γ$^{32}$P] ATP to a final concentration of 15 μM. The tubes were incubated at 30° C. for 5 min and the reactions were stopped by the addition of an equal volume of 2×SDS-PAGE sample buffer. The samples were then subjected to electrophoresis on 10% SDS-PAGE to resolve the histone H1 from other reaction components. The amount of radioactive phosphate transferred to histone H1 was quantified on a Storm Phosphorimager (Molecular Dynamics).

Prior to the protein kinase assay, test compounds were dissolved in DMSO at a concentration of 25 mM and were diluted to produce final concentrations of 0.1, 1.0, and 10.0 μM in the kinase assays. To eliminate possible effects of differences in DMSO concentration, the DMSO was kept constant at 0.04%, including the control reaction. Duplicate assays were performed at each concentration. The activity was plotted as the percent of activity in the absence of added test compound versus test compound concentration. IC$_{50}$ values were calculated using GraphPad Prism data analysis software.

D. Measuring the Inhibition of Cell Growth

Growth inhibition (GI$_{50}$) values were measured with HeLa S-3 cells selected for growth on plastic. The procedure was based on the protocol of Skehan et al. (Skehan, P., et al., *J. Natl. Cancer Inst.*, 82:1107–1112 (1990), which is hereby incorporated by reference) HeLa cells were plated at 2×10$^4$ cells/well in 96 well plates. One day later, a control plate was fixed by addition of TCA to 5%. After five rinses with tap water the plate was air dried and stored at 4° C. Test compounds were added to the remaining plates at 10-fold dilutions between 0.01 and 100 μM. Two days later all plates were fixed as described above. Cells were then stained by the addition of 100 μl per well of 0.4% sulforhodamine B (SRB) in 1% acetic acid for 30 min at 4° C. Wells were then quickly rinsed 5× with acetic acid (1%) and allowed to air dry. The SRB was then solubilized by the addition of 100 μl per well of unbuffered 10 mM Tris base. Dye was quantified by measuring absorbance at 490 nm on a Molecular Devices kinetic microplate reader. Growth at each inhibitor concentration relative to the untreated control was calculated according to the following equation: percent growth=100× (T–T$_o$)/(C–T$_o$), where T was the average optical density (OD) of the test wells after 2 days of treatment, T$_o$ was the average OD of the wells in the control plate on day 0 and C was the average OD of untreated wells. Plots of percent growth versus inhibitor concentration were used to determine the $GI_{50}$.

The data below shown in Table 2 summarizes the in vitro cyclin/cdk inhibition constants ($IC_{50}$) and growth inhibition constants ($GI_{50}$) of HeLa Cells for the compounds of the current invention. Replicate experimental results are summarized below.

TABLE 2

In Vitro Cyclin/cdk Inhibition ($IC_{50}$)
and Growth Inhibition ($GI_{50}$) of HeLa Cells
For Compounds of the Current Invention.

| Compound | $IC_{50}$ CyclinA/cdk2 (μM) | $IC_{50}$ CyclinE/cdk2 (μM) | $IC_{50}$ CyclinB/cdk1 (μM) | $GI_{50}$ HeLa Cells (μM) |
|---|---|---|---|---|
| 5 | >10 | 12 | 7 | 5 |
|  | 0.4 | 0.6 |  | >10 |
| 12 | 2 | 1 | 3 | 0.06 |
|  | 0.7 | 3 |  | 0.003 |
|  | 0.9 | 0.5 |  | 0.001 |
|  | 0.2 | 0.1 |  | 0.02 |
|  |  |  |  | 0.0001 |
| 13 | 4 | 2 | 4 | 3 |
|  | 1 | 0.3 |  | 2 |
|  | 0.8 | 0.9 |  |  |
| 14 | 3 | 0.4 | 7 | 0.4 |
|  | 3 | 2 |  | 0.03 |
|  |  |  |  | 0.03 |
| 17 | 1 | 1 | 10 | 0.4 |
|  | 2 | 0.9 | 3 | 0.6 |
|  | 1 | 0.2 | 11 | 0.25 |
|  | >10 | 9 |  | 0.4 |
|  | 10 | 2 |  | 0.3 |
|  |  |  |  | 0.4 |
| 25 | 1 | 4 | >10 | 2 |
|  | 6 | 1 | >10 | 0.4 |
|  | >10 | 9 |  | >1 |
| 32 | 2 | 3 | — | 5 |
|  | 5 | 0.9 |  | 0.7 |
| 33 | >10 | 4 | >10 | 1 |
|  | 13 | 6 |  | 2 |
|  | 8 |  |  | 0.9 |
| 34 | 12 | 5 | >10 | 7 |
|  | 13 | 2 |  | 6 |
|  |  |  |  | 7 |
| 36 | >10 | >10 | >10 | 20 |
|  | >10 | >10 |  | 20 |
|  | >10 |  |  | >10 |
| 38 | >10 | >10 | >10 | 0.6 |
|  | >10 | >10 |  | 1 |
|  |  |  |  | 0.6 |
| 40 | >10 | >10 | >10 | 9 |
|  | >10 | >10 |  | 25 |
|  |  |  |  | >10 |
| 43 | >10 | >10 | >10 | 4 |
|  | >10 | >10 |  | 4 |
|  |  |  |  | 8 |
| 46 | >10 | 6 | >10 | 25 |
|  | 8 | 3 |  | >10 |
| 48 | 22 | 1 | >10 | 0.3 |
|  | 6 | 5 |  | 0.6 |
|  |  |  |  | 0.5 |
| 50 | >10 | >10 | >10 | 3 |
|  | 7 | 9 |  | >10 |
| 53 | >10 | 15 | >10 | 0.2 |
|  | >10 | 4 |  | 0.3 |
|  |  |  |  | 0.5 |
| 58 | 11 | 2 | 12 | 2 |
|  | 4 | 4 |  | 0.5 |
|  |  |  |  | 0.7 |
| 60 | >10 | 12 | >10 | 7 |
|  | 0.4 | >10 |  | 6 |
| 73 | >50 | 4 | >10 | 0.3 |
|  | 14 | 12 |  | 0.5 |
|  | >10 | >10 |  | 0.3 |
| 74 | >10 | >10 |  | 0.5 |
|  | 5 | 2 | 6 | 0.2 |
|  | 2 | 3 |  | 0.01 |
|  | 1 | 2 |  | 0.05 |
|  |  |  |  | 0.03 |
|  |  |  |  | 0.05 |
| 75 | 3 | 3 | 6 | 0.09 |
|  |  |  |  | 0.02 |
|  |  |  |  | 0.005 |
| 76 | 12 | 3 | 6 | 0.07 |
|  | 11 | 5 |  | 0.01 |
|  | 3 | 2 |  | 0.06 |
|  |  |  |  | 0.2 |
|  |  |  |  | 0.04 |
| 77 | >10 | 4 | >10 | 0.15 |
|  | >10 | 14 |  | 0.5 |
|  |  |  |  | 0.3 |
| 78 | 0.9 | 0.6 | 0.8 | 0.05 |
|  | 0.9 | 0.3 | 0.8 | 0.025 |
|  | 0.7 | 0.2 |  | 0.08 |
|  |  |  |  | 0.002 |
| 79 | 10 | 2 | 3 | 0.07 |
|  | 0.5 | 0.1 |  | 0.007 |
|  | 1 | 0.08 |  | 0.004 |
|  |  |  |  | 0.4 |
| 80 | >10 | >10 | >10 | >100 |
|  | >10 | 4 |  | >10 |
|  |  | 2 |  |  |
| 86 | 0.9 | 0.4 | 2 | 0.2 |
|  | 0.7 | 0.2 |  | 0.03 |
|  | 0.4 | 0.4 |  | 0.01 |
|  | 0.6 | 0.03 |  | 0.01 |
|  |  |  |  | 0.2 |
| 87 | 4 | 1 | 5 | 0.07 |
|  | 2 | 0.3 |  | 0.01 |
|  | 0.5 | 0.1 |  | 0.004 |
|  |  |  |  | 0.006 |
|  |  |  |  | 0.03 |
|  |  |  |  | 0.006 |
|  |  |  |  | 0.001 |
|  |  |  |  | 0.0001 |
| 88 | 3 | 4 | >10 | 0.1 |
|  | >10 | >10 |  | 0.05 |
|  | 2 | 5 |  | 0.04 |
|  |  |  |  | 0.005 |
| 93 | 0.2 | 0.09 | 0.9 | 0.3 |
|  | 0.3 | 0.1 |  | 0.08 |
|  |  |  |  | 0.3 |
| 94 | 0.6 | 0.3 | 0.4 | 0.1 |
|  | 0.2 | 0.3 |  | 0.07 |
|  |  |  |  | 0.4 |
| 95 | 1 | 1 | 4 | 0.08 |
|  | 2 | 0.7 |  | 0.003 |
|  |  |  |  | 0.0005 |
| 96 | 8 | 4 | 6 | 0.04 |
|  |  |  |  | 0.01 |
| 97 | >10 | 3 | 10 | 3 |
| 98 | 6 | 2 | >10 | >10 |
|  | 2 | 2 |  | 11 |
| 99 | >10 | 9 | >10 | 5 |
| 100 | >10 | 4 | >10 | 0.6 |
| 101 | 3 | 1 | 4 |  |
|  | 0.9 | 0.7 |  |  |
| 102 | >10 | 4 | — | 4 |
| 103 | 0.6 | 0.2 | 1 | 0.03 |
|  | 0.7 | 0.2 |  | 0.008 |
|  |  |  |  | 0.02 |
|  |  |  |  | 0.01 |
| 104 | 7 | 1 | 2 | 0.4 |
|  | 8 | 1 |  | 0.2 |
| 106 | 11 | 3 | — | 0.3 |

TABLE 2-continued

In Vitro Cyclin/cdk Inhibition (IC$_{50}$) and Growth Inhibition (GI$_{50}$) of HeLa Cells For Compounds of the Current Invention.

| Compound | IC$_{50}$ CyclinA/cdk2 (μM) | IC$_{50}$ CyclinE/cdk2 (μM) | IC$_{50}$ CyclinB/cdk1 (μM) | GI$_{50}$ HeLa Cells (μM) |
|---|---|---|---|---|
|  | 4 | 1 | — | 0.1 |
| 107 | 1 | 2 | — | 0.4 |
|  | 4 |  |  | 0.3 |
| 108 | 10 | >10 | — | 3 |
|  | >10 | >10 |  | 5 |
| 109 | 0.6 | 0.1 | — | 0.04 |
|  |  |  |  | <0.0001 |
| 110 | 0.6 | 2 | — | 0.02 |
|  |  |  |  | 0.03 |
|  |  |  |  | 0.02 |
|  |  |  |  | 0.01 |
| 111 | 0.2 | 0.07 | — | 0.02 |
|  |  |  |  | 0.0006 |
| 112 | 2 | 2 | — | <0.001 |
|  |  |  |  | 0.002 |
|  |  |  |  | 0.02 |
|  |  |  |  | 0.006 |
|  |  |  |  | 0.0006 |
| 113 | 0.4 | 0.3 | — | <0.001 |
|  |  |  |  | 0.00001 |
|  |  |  |  | 0.03 |
|  |  |  |  | 0.001 |
|  |  |  |  | 0.02 |
| 114 | 3 | 0.7 | — | >10 |
| 115 | 3 | 0.4 | — | 3 |
| 116 | >10 | >10 | — | >10 |
|  |  |  |  | >10 |
| 117 | >10 | 3 | — | 3 |
| 118 | 6 | 1 | — | >10 |
|  |  |  |  | >10 |
| 123 | 0.2 | 0.04 | — | <0.001 |
|  |  |  |  | <0.001 |
|  |  |  |  | 0.0001 |
| 124 | 2 | 0.8 | — | 0.003 |
|  |  |  |  | <0.001 |
|  |  |  |  | <0.0001 |

The data below shown in Table 3 summarizes the in vitro cyclin/cdk inhibition (IC$_{50}$) and growth inhibition (GI$_{50}$) of HeLa Cells for several reference compounds in comparison to several compounds of the current invention. The chemical structures are provided.

TABLE 3

In Vitro cyclin/cdk Inhibition (IC$_{50}$) and Growth Inhibition (GI$_{50}$) of HeLa Cells For Reference Compounds in Comparison to Several Compounds of the Current Invention.

| Compound | Structure | IC$_{50}$ CyclinA/cdk2 (μM) | IC$_{50}$ CyclinE/cdk2 (μM) | IC$_{50}$ CyclinB/cdk1 (μM) | GI$_{50}$ HeLa Cells (μM) |
|---|---|---|---|---|---|
| Olomoucine | 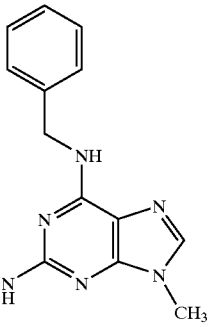 | 0.5–24 (n > 10) | 1–14 (n > 10) | 7–23 (n > 10) | 75 |
| Roscovitine | 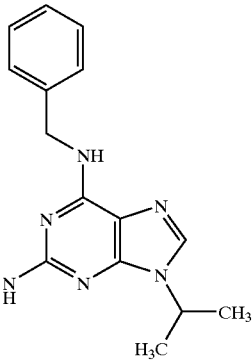 | 2.1<br>4<br>3 | 0.04<br>0.7 | — | 30<br>25<br>30<br>>10<br>25 |

TABLE 3-continued

In Vitro cyclin/cdk Inhibition (IC$_{50}$) and Growth Inhibition (GI$_{50}$) of HeLa Cells
For Reference Compounds in Comparison to Several Compounds of the Current Invention.

| Compound | Structure | IC$_{50}$ CyclinA/cdk2 ($\mu$M) | IC$_{50}$ CyclinE/cdk2 ($\mu$M) | IC$_{50}$ CyclinB/cdk1 ($\mu$M) | GI$_{50}$ HeLa Cells ($\mu$M) |
|---|---|---|---|---|---|
| Flavopiridol | 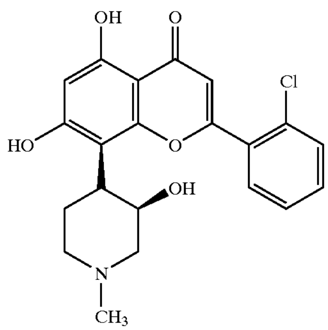 | 0.06 0.2 | 0.6 0.04 | 0.06 (n = 2) | 0.18 |
| 125 | 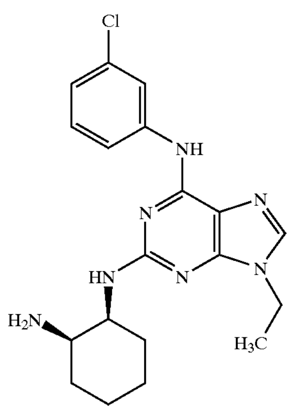 | 1 | 0.1 | 0.6 | 3 |
| 126 | 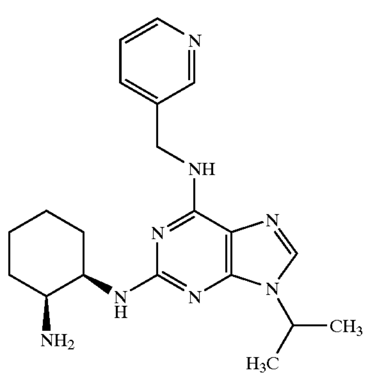 | 0.6 0.8 | 0.06 0.06 | 2 0.2 | 2 4 6 |

TABLE 3-continued

In Vitro cyclin/cdk Inhibition (IC$_{50}$) and Growth Inhibition (GI$_{50}$) of HeLa Cells
For Reference Compounds in Comparison to Several Compounds of the Current Invention.

| Compound | Structure | IC$_{50}$ CyclinA/cdk2 ($\mu$M) | IC$_{50}$ CyclinE/cdk2 ($\mu$M) | IC$_{50}$ CyclinB/cdk1 ($\mu$M) | GI$_{50}$ HeLa Cells ($\mu$M) |
|---|---|---|---|---|---|
| 74 | 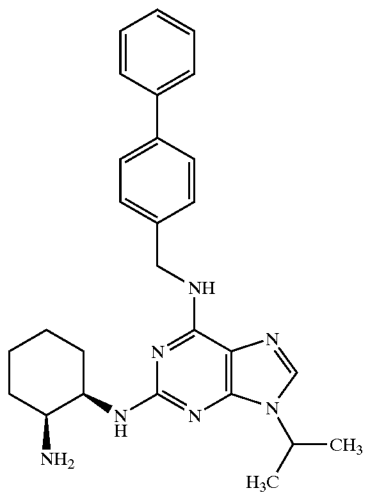 | 5 | 2 | 6 | 0.2<br>0.01<br>0.05 |
| 127 | 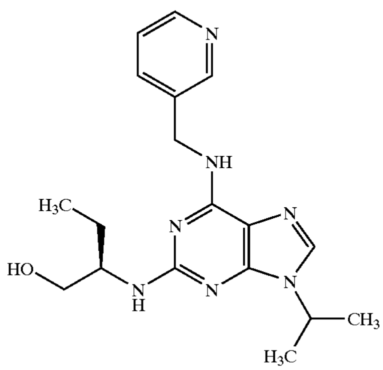 | 0.3–2<br>(n > 15) | 0.04–0.07<br>(n > 15) | 0.5–2<br>(n > 15) | 7–15<br>(n > 5) |
| 88 | 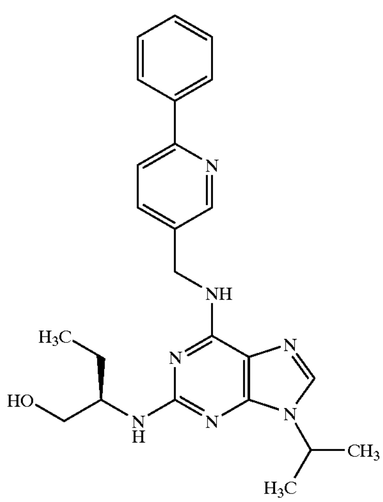 | 3 | 4 | >10 | 0.1<br>0.05<br>0.04 |

The following data in Tables 4, 5, 6, and 7 summarize the growth inhibition properties of several compounds of the current invention and olomoucine against 60-human transformed cell lines. These data were cooperatively obtained at the National Cancer Institute in their 60-cell line growth inhibition assay according to published procedures (Boyd, M. R., "Anticancer Drug Development Guide," *Preclinical Screening, Clinical Trials, and Approval*; Teicher, B. Ed.; Humana Press; Totowa, N.J., 23–42 (1997), which is hereby incorporated by reference).

TABLE 4

In Vitro Growth Inhibition ($GI_{50}$) of NCI Human Transformed Cell Lines of Several Compounds of the Current Invention.

| Cancer Type | Cell Line | 73 $GI_{50}$ ($\mu$M) | 17 $GI_{50}$ ($\mu$M) | 33 $GI_{50}$ ($\mu$M) | 38 $GI_{50}$ ($\mu$M) |
| --- | --- | --- | --- | --- | --- |
| Breast | BT-549 | 0.25 | 0.40 | 51.3 | 0.32 |
| Breast | HS 578T | 0.10 | 6.31 | — | — |
| Breast | MCF7 | 0.16 | 0.16 | 5.2 | 0.20 |
| Breast | MDA-MB-231/ATCC | 0.50 | — | — | 0.06 |
| Breast | MDA-MB-435 | 0.25 | 0.20 | 4.9 | 0.05 |
| Breast | MDA-N | 0.13 | 0.11 | — | — |
| Breast | NCI/ADR-RES | 0.40 | 0.28 | 6.3 | 0.32 |
| Breast | T-47D | 0.25 | 0.13 | 3.9 | 0.25 |
| CNS | SF-268 | 0.16 | 0.04 | 6.3 | 0.20 |
| CNS | SF-295 | 0.25 | 0.19 | 7.8 | 0.50 |
| CNS | SF-539 | 0.76 | 0.40 | 89.1 | 1.26 |
| CNS | SNB-19 | 0.43 | 0.14 | 38.0 | 0.50 |
| CNS | SNB-75 | 0.02 | 0.02 | — | — |
| CNS | U251 | 0.32 | 0.40 | 3.7 | 0.20 |
| Colon | COLO 205 | 0.28 | 0.05 | 7.8 | 0.16 |
| Colon | HCC-2998 | 0.20 | 0.03 | >1000 | 7.94 |
| Colon | HCT-116 | 0.20 | 0.16 | 6.2 | 0.32 |
| Colon | HCT-15 | 0.18 | 0.04 | 8.9 | 0.25 |
| Colon | HT29 | — | 0.10 | 8.9 | 0.25 |
| Colon | KM12 | 0.13 | 0.03 | 4.1 | 0.16 |
| Colon | SW-620 | — | 0.01 | 2.9 | 0.03 |
| Leukemia | CCRF-CEM | 0.25 | 0.16 | 4.6 | 0.20 |
| Leukemia | HL-60(TB) | — | — | 3.2 | 0.04 |
| Leukemia | K-562 | 0.16 | 0.16 | 3.1 | 0.25 |
| Leukemia | MOLT-4 | 0.32 | 0.25 | 3.8 | 0.25 |
| Leukemia | RPMI-8226 | 0.03 | 0.03 | 1.5 | — |
| Leukemia | SR | — | 0.50 | 4.5 | 3.98 |
| Melanoma | LOX IMVI | — | 0.32 | 16.6 | 0.40 |
| Melanoma | M14 | 0.03 | 0.03 | 7.8 | 0.05 |
| Melanoma | MALME-3M | 0.27 | 19.95 | 11.7 | 0.25 |
| Melanoma | SK-MEL-2 | 0.63 | 1.00 | >1000 | 2.00 |
| Melanoma | SK-MEL-28 | 0.45 | 0.12 | 5.9 | 0.03 |
| Melanoma | SK-MEL-5 | 0.25 | 0.32 | 16.2 | 0.32 |
| Melanoma | UACC-257 | 0.16 | 0.20 | 75.9 | 0.50 |
| Melanoma | UACC-62 | 0.30 | 0.27 | 8.3 | 1.00 |
| Non-Small Cell Lung | A549/ATCC | 0.03 | 0.03 | 4.6 | 0.13 |
| Non-Small Cell Lung | EKVX | 0.25 | 2.51 | 6.9 | 0.20 |
| Non-Small Cell Lung | HOP-62 | 0.06 | 0.20 | >1000 | 0.32 |
| Non-Small Cell Lung | HOP-92 | 1.00 | 1.58 | — | 0.32 |
| Non-Small Cell Lung | NCI-H226 | 0.22 | 0.11 | — | — |
| Non-Small Cell Lung | NCI-H23 | 0.32 | 0.16 | 26.3 | 0.32 |
| Non-Small Cell Lung | NCI-H322M | 0.16 | >1000 | 38.9 | 0.40 |
| Non-Small Cell Lung | NCI-H460 | 0.40 | 0.41 | 25.7 | 3.16 |
| Non-Small Cell Lung | NCI-H522 | — | — | 4.2 | — |
| Ovarian | IGROV1 | 0.32 | 0.20 | 10.0 | 0.16 |
| Ovarian | OVCAR-3 | 0.30 | 0.65 | >1000 | 1.00 |
| Ovarian | OVCAR-4 | 0.32 | 0.32 | 31.6 | 1.26 |
| Ovarian | OVCAR-5 | 0.25 | 0.26 | >1000 | 0.40 |
| Ovarian | OVCAR-8 | — | 0.13 | 6.6 | 0.25 |
| Ovarian | SK-OV-3 | 0.95 | 0.40 | >1000 | 3.98 |
| Prostate | DU-145 | 7.08 | 0.63 | 17.8 | 1.26 |
| Prostate | PC-3 | 0.35 | 0.20 | >1000 | 0.40 |
| Renal | 786-0 | 0.20 | 0.25 | 18.6 | 0.32 |
| Renal | A498 | 2.88 | 1.58 | — | 1.26 |
| Renal | ACHN | 0.32 | 0.40 | 5.2 | 2.00 |
| Renal | CAKI-1 | 1.66 | 0.13 | 4.4 | 0.20 |
| Renal | RXF 393 | 0.09 | 0.02 | 13.2 | 0.13 |
| Renal | SN12C | — | 0.56 | — | — |
| Renal | TK-10 | — | — | 8.3 | 0.40 |
| Renal | UO-31 | 0.06 | 0.10 | 8.1 | 0.13 |

TABLE 5

In Vitro Growth Inhibition (GI$_{50}$) of NCI Human Transformed Cell Lines
of Several Compounds of the Current Invention.

| Cancer Type | Cell Line | 43 GI$_{50}$ ($\mu$M) | 48 GI$_{50}$ ($\mu$M) | 75 GI$_{50}$ ($\mu$M) | 76 GI$_{50}$ ($\mu$M) |
| --- | --- | --- | --- | --- | --- |
| Breast | BT-549 | 4.0 | 0.01 | <0.01 | <0.01 |
| Breast | HS 578T | — | 0.03 | <0.01 | <0.01 |
| Breast | MCF7 | 2.7 | 0.25 | <0.01 | <0.01 |
| Breast | MDA-MB-231/ATCC | 3.2 | 0.09 | <0.01 | <0.01 |
| Breast | MDA-MB-435 | 2.1 | — | — | — |
| Breast | MDA-N | — | 0.02 | <0.01 | <0.01 |
| Breast | NCI/ADR-RES | 5.2 | 0.12 | 0.48 | 0.015 |
| Breast | T-47D | 2.2 | 0.15 | <0.01 | <0.01 |
| CNS | SF-268 | 3.0 | <0.01 | <0.01 | <0.01 |
| CNS | SF-295 | 4.0 | 0.24 | <0.01 | <0.01 |
| CNS | SF-539 | 3.4 | 0.38 | 0.02 | 0.054 |
| CNS | SNB-19 | 5.0 | 0.02 | <0.01 | <0.01 |
| CNS | SNB-75 | — | <0.01 | <0.01 | <0.01 |
| CNS | U251 | 2.3 | 0.17 | <0.01 | 0.020 |
| Colon | COLO 205 | 1.6 | 0.03 | <0.01 | <0.01 |
| Colon | HCC-2998 | 3.4 | — | — | — |
| Colon | HCT-116 | 2.1 | 0.19 | <0.01 | 0.014 |
| Colon | HCT-15 | 3.9 | 0.02 | 0.03 | <0.01 |
| Colon | HT29 | 3.6 | <0.01 | <0.01 | <0.01 |
| Colon | KM12 | 2.3 | 0.02 | <0.01 | <0.01 |
| Colon | SW-620 | 1.6 | <0.01 | <0.01 | <0.01 |
| Leukemia | CCRF-CEM | 2.8 | 0.03 | <0.01 | <0.01 |
| Leukemia | HL-60(TB) | 2.1 | — | — | — |
| Leukemia | K-562 | 3.1 | 0.16 | <0.01 | <0.01 |
| Leukemia | MOLT-4 | 2.0 | 0.05 | <0.01 | <0.01 |
| Leukemia | RPMI-8226 | — | <0.01 | <0.01 | <0.01 |
| Leukemia | SR | 2.2 | 0.16 | <0.01 | <0.01 |
| Melanoma | LOX IMVI | 3.4 | 0.19 | <0.01 | <0.01 |
| Melanoma | M14 | 2.2 | <0.01 | <0.01 | <0.01 |
| Melanoma | MALME-3M | 3.0 | 0.13 | <0.01 | <0.01 |
| Melanoma | SK-MEL-2 | 61.7 | 0.48 | 0.02 | 0.112 |
| Melanoma | SK-MEL-28 | 2.3 | <0.01 | <0.01 | <0.01 |
| Melanoma | SK-MEL-5 | 2.1 | 0.17 | 0.01 | 0.013 |
| Melanoma | UACC-257 | 4.8 | 0.04 | <0.01 | <0.01 |
| Melanoma | UACC-62 | 3.3 | 0.10 | 0.01 | 0.018 |
| Non-Small Cell Lung | A549/ATCC | 4.1 | <0.01 | <0.01 | <0.01 |
| Non-Small Cell Lung | EKVX | 2.8 | — | — | — |
| Non-Small Cell Lung | HOP-62 | 3.3 | 0.03 | <0.01 | <0.01 |
| Non-Small Cell Lung | HOP-92 | 2.6 | 0.46 | <0.01 | 0.017 |
| Non-Small Cell Lung | NCI-H226 | — | — | — | — |
| Non-Small Cell Lung | NCI-H23 | 4.3 | 0.07 | <0.01 | <0.01 |
| Non-Small Cell Lung | NCI-H322M | 3.5 | 0.03 | <0.01 | <0.01 |
| Non-Small Cell Lung | NCI-H460 | 3.2 | 0.25 | <0.01 | 0.047 |
| Non-Small Cell Lung | NCI-H522 | — | <0.01 | <0.01 | <0.01 |
| Ovarian | IGROV1 | 3.4 | 0.23 | <0.01 | <0.01 |
| Ovarian | OVCAR-3 | 9.3 | 0.17 | <0.01 | <0.01 |
| Ovarian | OVCAR-4 | 8.9 | 0.20 | <0.01 | <0.01 |
| Ovarian | OVCAR-5 | 3.6 | 0.16 | <0.01 | <0.01 |
| Ovarian | OVCAR-8 | 3.9 | 0.10 | <0.01 | <0.01 |
| Ovarian | SK-OV-3 | 72.4 | 1.38 | 0.03 | 0.051 |
| Prostate | DU-145 | 2.6 | 0.55 | <0.01 | 0.043 |
| Prostate | PC-3 | 38.9 | 0.23 | <0.01 | <0.01 |
| Renal | 786-0 | 3.1 | 0.25 | <0.01 | <0.01 |
| Renal | A498 | 3.0 | 0.39 | 0.01 | <0.01 |
| Renal | ACHN | 3.1 | 0.25 | 0.02 | 0.025 |
| Renal | CAKI-1 | 3.0 | — | — | — |
| Renal | RXF 393 | 1.9 | <0.01 | <0.01 | <0.01 |
| Renal | SN12C | — | 0.03 | <0.01 | <0.01 |
| Renal | TK-10 | 3.2 | 0.37 | <0.01 | 0.013 |
| Renal | UO-31 | 2.8 | <0.01 | 0.03 | <0.01 |

TABLE 6

In Vitro Growth Inhibition (GI$_{50}$) of NCI Human Transformed Cell Lines
of Several Compounds of the Current Invention.

| Cancer Type | Cell Line | 79 GI$_{50}$ ($\mu$M) | 87 GI$_{50}$ ($\mu$M) | 12 GI$_{50}$ ($\mu$M) |
| --- | --- | --- | --- | --- |
| Breast | BT-549 | <0.01 | 0.02 | 0.041 |
| Breast | HS 578T | <0.01 | <0.01 | <0.005 |
| Breast | MCF7 | <0.01 | 0.04 | <0.005 |

TABLE 6-continued

In Vitro Growth Inhibition (GI$_{50}$) of NCI Human Transformed Cell Lines of Several Compounds of the Current Invention.

| Cancer Type | Cell Line | 79 GI$_{50}$ ($\mu$M) | 87 GI$_{50}$ ($\mu$M) | 12 GI$_{50}$ ($\mu$M) |
|---|---|---|---|---|
| Breast | MDA-MB-231/ATCC | <0.01 | <0.01 | <0.005 |
| Breast | MDA-MB-435 | <0.01 | <0.01 | <0.005 |
| Breast | MDA-N | <0.01 | 0.014 | <0.005 |
| Breast | NCI/ADR-RES | 0.86 | 0.28 | 1.26 |
| Breast | T-47D | <0.01 | 0.048 | 0.0088 |
| CNS | SF-268 | <0.01 | <0.01 | <0.005 |
| CNS | SF-295 | <0.01 | 0.047 | 0.018 |
| CNS | SF-539 | <0.01 | 0.081 | 0.022 |
| CNS | SNB-19 | <0.01 | 0.038 | 0.016 |
| CNS | SNB-75 | <0.01 | 0.012 | <0.005 |
| CNS | U251 | <0.01 | 0.028 | 0.0078 |
| Colon | COLO 205 | <0.01 | <0.01 | <0.005 |
| Colon | HCC-2998 | <0.01 | <0.01 | <0.005 |
| Colon | HCT-116 | <0.01 | 0.037 | 0.0089 |
| Colon | HCT-15 | <0.01 | 0.066 | 0.17 |
| Colon | HT29 | <0.01 | <0.01 | <0.005 |
| Colon | KM12 | <0.01 | <0.01 | <0.005 |
| Colon | SW-620 | <0.01 | <0.01 | <0.005 |
| Leukemia | CCRF-CEM | <0.01 | <0.01 | <0.005 |
| Leukemia | HL-60(TB) | <0.01 | <0.01 | <0.005 |
| Leukemia | K-562 | <0.01 | 0.024 | <0.005 |
| Leukemia | MOLT-4 | <0.01 | 0.02 | <0.005 |
| Leukemia | RPMI-8226 | <0.01 | <0.01 | <0.005 |
| Leukemia | SR | <0.01 | 0.032 | <0.005 |
| Melanoma | LOX IMVI | <0.01 | 0.027 | <0.005 |
| Melanoma | M14 | <0.01 | <0.01 | <0.005 |
| Melanoma | MALME-3M | <0.01 | 0.024 | 0.010 |
| Melanoma | SK-MEL-2 | <0.01 | 0.056 | 0.0096 |
| Melanoma | SK-MEL-28 | <0.01 | <0.01 | 0.01 |
| Melanoma | SK-MEL-5 | <0.01 | 0.028 | 0.014 |
| Melanoma | UACC-257 | <0.01 | 0.017 | 0.008 |
| Melanoma | UACC-62 | <0.01 | 0.045 | 0.027 |
| Non-Small Cell Lung | A549/ATCC | <0.01 | <0.01 | <0.005 |
| Non-Small Cell Lung | EKVX | <0.01 | 0.081 | 0.023 |
| Non-Small Cell Lung | HOP-62 | <0.01 | 0.01 | <0.005 |
| Non-Small Cell Lung | HOP-92 | <0.01 | 0.088 | 0.011 |
| Non-Small Cell Lung | NCI-H226 | <0.01 | 0.0.052 | 0.021 |
| Non-Small Cell Lung | NCI-H23 | <0.01 | 0.022 | <0.005 |
| Non-Small Cell Lung | NCI-H322M | <0.01 | 0.021 | <0.005 |
| Non-Small Cell Lung | NCI-H460 | <0.01 | 0.22 | 0.015 |
| Non-Small Cell Lung | NCI-H522 | <0.01 | <0.01 | <0.005 |
| Ovarian | IGROV1 | <0.01 | 0.052 | 0.013 |
| Ovarian | OVCAR-3 | <0.01 | 0.05 | 0.012 |
| Ovarian | OVCAR-4 | <0.01 | 0.048 | <0.005 |
| Ovarian | OVCAR-5 | <0.01 | 0.051 | 0.017 |
| Ovarian | OVCAR-8 | <0.01 | 0.033 | 0.0076 |
| Ovarian | SK-OV-3 | <0.01 | 0.35 | 0.018 |
| Prostate | DU-145 | <0.01 | 0.22 | 0.017 |
| Prostate | PC-3 | <0.01 | 0.018 | <0.005 |
| Renal | 786-0 | <0.01 | 0.047 | 0.0065 |
| Renal | A498 | <0.01 | 0.10 | 0.016 |
| Renal | ACHN | <0.01 | 0.19 | 0.039 |
| Renal | CAKI-1 | <0.01 | 0.064 | 0.038 |
| Renal | RXF 393 | <0.01 | 0.011 | <0.005 |
| Renal | SN12C | <0.01 | <0.01 | <0.005 |
| Renal | TK-10 | <0.01 | 0.029 | 0.01 |
| Renal | UO-31 | <0.01 | 0.016 | 0.063 |

TABLE 7

In Vitro Growth Inhibition (GI$_{50}$) of NCI Human Transformed Cell Lines of Several Compounds of the Current Invention and Olomoucine.

| Cancer Type | Cell Line | 74 GI$_{50}$ ($\mu$M) | 78 GI$_{50}$ ($\mu$M) | 77 GI$_{50}$ ($\mu$M) | Olomoucine GI$_{50}$ ($\mu$M) |
| --- | --- | --- | --- | --- | --- |
| Breast | BT-549 | 0.16 | 0.04 | <0.01 | 79 |
| Breast | HS 578T | <0.01 | — | <0.01 | 63 |
| Breast | MCF7 | <0.01 | <0.01 | 0.03 | 50 |
| Breast | MDA-MB-231/ATCC | <0.01 | <0.01 | 0.04 | 100 |
| Breast | MDA-MB-435 | — | — | — | 63 |
| Breast | MDA-N | <0.01 | <0.01 | 0.01 | 79 |
| Breast | NCI/ADR-RES | 0.24 | 14.45 | 0.03 | 100 |
| Breast | T-47D | <0.01 | 0.03 | 0.01 | 63 |
| CNS | SF-268 | <0.01 | — | <0.01 | 50 |
| CNS | SF-295 | <0.01 | 0.21 | 0.04 | 79 |
| CNS | SF-539 | 0.07 | — | 0.22 | 32 |
| CNS | SNB-19 | <0.01 | <0.01 | 0.03 | 63 |
| CNS | SNB-75 | <0.01 | <0.01 | <0.01 | 25 |
| CNS | U251 | <0.01 | 0.02 | 0.09 | 50 |
| Colon | COLO 205 | <0.01 | <0.01 | 0.02 | 32 |
| Colon | HCC-2998 | — | <0.01 | — | 63 |
| Colon | HCT-116 | <0.01 | 0.03 | 0.05 | 40 |
| Colon | HCT-15 | <0.01 | 1.48 | <0.01 | 40 |
| Colon | HT29 | <0.01 | <0.01 | <0.01 | 63 |
| Colon | KM12 | <0.01 | <0.01 | <0.01 | 40 |
| Colon | SW-620 | <0.01 | <0.01 | <0.01 | 40 |
| Leukemia | CCRF-CEM | <0.01 | — | <0.01 | 40 |
| Leukemia | HL-60(TB) | — | <0.01 | — | 40 |
| Leukemia | K-562 | <0.01 | 0.02 | 0.02 | 100 |
| Leukemia | MOLT-4 | <0.01 | <0.01 | 0.01 | 63 |
| Leukemia | RPMI-8226 | <0.01 | <0.01 | <0.01 | 50 |
| Leukemia | SR | <0.01 | — | 0.02 | 25 |
| Melanoma | LOX IMVI | <0.01 | — | 0.04 | 32 |
| Melanoma | M14 | <0.01 | <0.01 | <0.01 | 100 |
| Melanoma | MALME-3M | 0.01 | 0.01 | 0.05 | 100 |
| Melanoma | SK-MEL-2 | 0.06 | 0.02 | 0.51 | 100 |
| Melanoma | SK-MEL-28 | <0.01 | 0.01 | <0.01 | 50 |
| Melanoma | SK-MEL-5 | 0.06 | 0.10 | 0.08 | 40 |
| Melanoma | UACC-257 | <0.01 | 0.02 | 0.02 | 79 |
| Melanoma | UACC-62 | 0.04 | 0.03 | 0.12 | 32 |
| Non-Small Cell Lung | A549/ATCC | <0.01 | <0.01 | <0.01 | 50 |
| Non-Small Cell Lung | EKVX | — | 0.05 | — | 100 |
| Non-Small Cell Lung | HOP-62 | <0.01 | 0.02 | <0.01 | 32 |
| Non-Small Cell Lung | HOP-92 | 0.03 | — | 0.13 | 50 |
| Non-Small Cell Lung | NCI-H226 | — | 0.02 | — | 50 |
| Non-Small Cell Lung | NCI-H23 | <0.01 | 0.01 | 0.01 | 79 |
| Non-Small Cell Lung | NCI-H322M | <0.01 | <0.01 | <0.01 | 63 |
| Non-Small Cell Lung | NCI-H460 | <0.01 | 0.05 | 0.22 | 63 |
| Non-Small Cell Lung | NCI-H522 | <0.01 | <0.01 | <0.01 | 40 |
| Ovarian | IGROV1 | <0.01 | <0.01 | 0.09 | 40 |
| Ovarian | OVCAR-3 | <0.01 | 0.03 | 0.02 | 79 |
| Ovarian | OVCAR-4 | <0.01 | 0.02 | <0.01 | 100 |
| Ovarian | OVCAR-5 | 0.03 | <0.01 | 0.04 | 40 |
| Ovarian | OVCAR-8 | <0.01 | 0.02 | 0.02 | 63 |
| Ovarian | SK-OV-3 | 0.22 | 0.06 | 0.19 | 100 |
| Prostate | DU-145 | 0.02 | 0.06 | 0.13 | 40 |
| Prostate | PC-3 | <0.01 | <0.01 | 0.02 | 100 |
| Renal | 786-0 | <0.01 | 0.04 | 0.03 | 63 |
| Renal | A498 | 0.03 | 0.03 | 0.03 | 32 |
| Renal | ACHN | 0.03 | 0.32 | 0.11 | 25 |
| Renal | CAKI-1 | — | 0.79 | — | 32 |
| Renal | RXF 393 | <0.01 | <0.01 | <0.01 | 20 |
| Renal | SN12C | <0.01 | <0.01 | <0.01 | 100 |
| Renal | TK-10 | <0.01 | 0.07 | 0.05 | 63 |
| Renal | UO-31 | 0.01 | 0.17 | <0.01 | 32 |

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A compound of the following formula:

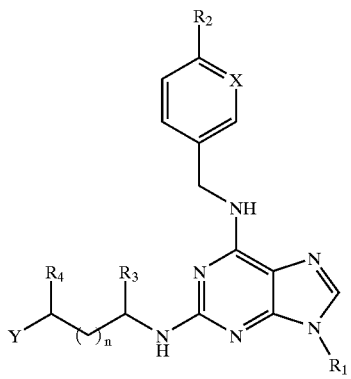

Formula I wherein:

$R_1$ are the same or different and independently selected from the group consisting of:
H;
$C_1$–$C_4$-straight chain alkyl; and
$C_3$–$C_4$-branched chain alkyl;
X=N;
$R_2$=
phenyl;
substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, NHC(O)$CH_3$, F, Cl, Br, $CF_3$, $C(O)R_1$, phenyl, $C(O)NHCHR_1CH_2OH$;
1-naphthyl;
2-naphthyl;
heterocycles selected from the group consisting of:
2-pyridyl;
3-pyridyl;
4-pyridyl;
5-pyrimidyl;
thiophene-2-yl;
thiophene-3-yl;
2-furanyl;
3-furanyl;
2-benzofuranyl;
benzothiophene-2-yl;
2-pyrrolyl;
3-pyrrolyl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;
$R_3$ are the same or different and independently selected from the group consisting of:
H;
$C_1$–$C_4$-straight chain alkyl;
$C_3$–$C_4$-branched chain alkyl;
$C_2$–$C_4$-alkenyl chain;
$(CH_2)_n$Ph; and
$(CH_2)_n$-substituted phenyl, wherein the phenyl substituents are as defined above in $R_2$;
$R_4$=
H;
$C_1$–$C_4$-straight chain alkyl; or
$C_3$–$C_4$-branched chain alkyl;
$R_3$ and $R_4$ can be linked together by a carbon chain to form with intervening atoms a 5–8-membered ring;
n=0–3;
Y=
H;
$OR_1$;
$NHR_1$;
$NHC(O)R_3$;
$NHSO_2R_3$;
$NHC(O)NHR_3$;
$NHC(O)R_5$; or
$NHC(O)OR_6$;
$R_5$=$C_3$–$C_7$-cycloalkyl;
$R_6$=
$C_1$–$C_4$-straight chain alkyl;
$C_3$–$C_4$-branched chain alkyl;
$C_2$–$C_4$-alkenyl chain;
$(CH_2)_n$Ph; or
$(CH_2)_n$-substituted phenyl, wherein the phenyl substituents are as defined above in $R_2$;
or a pharmaceutically acceptable salt thereof.

2. A process for preparation of a purine derivative compound of the formula:

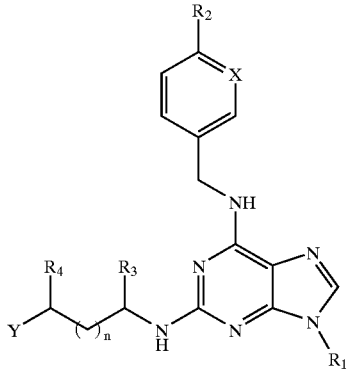

wherein:

$R_1$ are the same or different and independently selected from the group consisting of:
H;
$C_1$–$C_4$-straight chain alkyl; and
$C_3$–$C_4$-branched chain alkyl;
X=N;
$R_2$=
phenyl; substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, $C(O)NHCHR_1CH_2OH$;

1-naphthyl;
2-naphthyl;
heterocycles selected from the group consisting of:
   2-pyridyl;
   3-pyridyl;
   4-pyridyl;
   5-pyrimidyl;
   thiophene-2-yl;
   thiophene-3-yl;
   2-furanyl;
   3-furanyl;
   2-benzofuranyl;
   benzothiophene-2-yl;
   2-pyrrolyl;
   3-pyrrolyl;
   2-quinolinyl;
   3-quinolinyl;
   4-quinolinyl;
   1-isoquinolinyl;
   3-isoquinolinyl; and
   4-isoquinolinyl; or
substituted heterocycle, wherein the substituents (1–2 in number) are in any position and are independently selected from the group consisting of Br, Cl, F, $R_1$, and $C(O)CH_3$;

$R_3$ are the same or different and independently selected from the group consisting of:
   H;
   $C_1$–$C_4$-straight chain alkyl;
   $C_3$–$C_4$-branched chain alkyl;
   $C_2$–$C_4$-alkenyl chain;
   $(CH_2)_n Ph$; and
   $(CH_2)_n$-substituted phenyl, wherein the phenyl substituents are as defined above in $R_2$;

$R_4$=
   H;
   $C_1$–$C_4$-straight chain alkyl; or
   $C_3$–$C_4$-branched chain alkyl;

$R_3$ and $R_4$ can be linked together by a carbon chain to form with intervening atoms a 5–8-membered ring;

n=0–3;

Y=
   H;
   $OR_1$;
   $NHR_1$;
   $NHC(O)R_3$;
   $NHSO_2R_3$;
   $NHC(O)NHR_3$;
   $NHC(O)R_5$; or
   $NHC(O)OR_6$;

$R_5$=$C_3$–$C_7$-cycloalkyl;

$R_6$=
   $C_1$–$C_4$-straight chain alkyl;
   $C_3$–$C_4$-branched chain alkyl;
   $C_2$–$C_4$-alkenyl chain;
   $(CH_2)_n Ph$; or
   $(CH_2)_n$-substituted phenyl, wherein the phenyl substituents are as defined above in $R_2$; or a pharmaceutically acceptable salt thereof, said process comprising:

reacting a first intermediate compound of the formula:

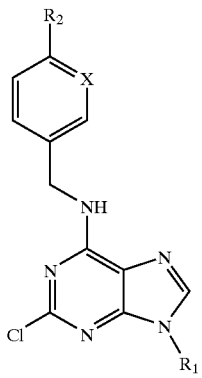

Formula XVII with a second compound of the formula:

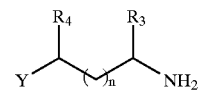

Formula VIII under conditions effective to form the purine derivative compound.

3. A process according to claim 2, wherein if Y in the second compound is $NH_2$, said process further comprises:
   reacting the purine derivative compound with $R_3C(O)Cl$ or $R_3SO_2Cl$ or $R_3NCO$ or $R_3OC(O)Cl$ under conditions effective to form a final product having the same formula as the purine derivative compound except that Y is $NHC(O)R_3$ or $NHSO_2R_3$ or $NHC(O)NHR_3$ or $NHC(O)OR_6$.

4. A compound according to claim 1, wherein
$R_3$ are the same or different and independently selected from:
   H;
   $C_1$–$C_4$-straight chain alkyl;
   $C_3$–$C_4$-branched chain alkyl;

Y=
   H;
   $OR_1$;
   $NHR_1$;
   $NHC(O)R_3$;
   $NHSO_2R_3$;
   $NHC(O)NHR_3$; or a pharmaceutically acceptable salt thereof.

5. A compound having the following formula:

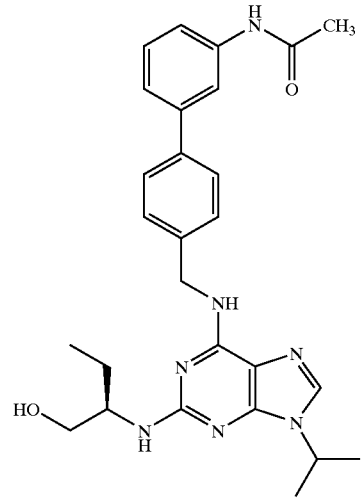

Formula VII or a pharmaceutically acceptable salt thereof.

6. A compound having the following formula:

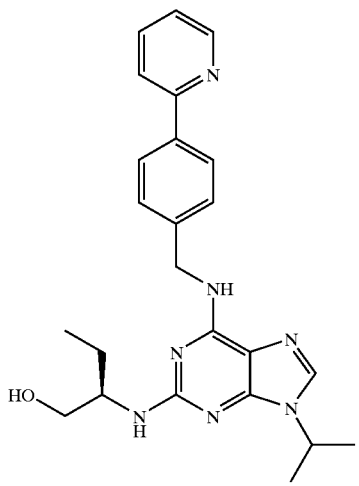

Formula XI or a pharmaceutically acceptable salt thereof.

7. A process according to claim 2 further comprising:

reacting a third intermediate compound of the formula:

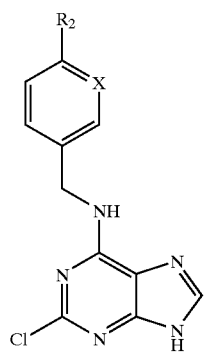

Formula XVI with a compound of the formula R₁—Z under conditions effective to form the first intermediate compound.

8. A compound having the following formula:

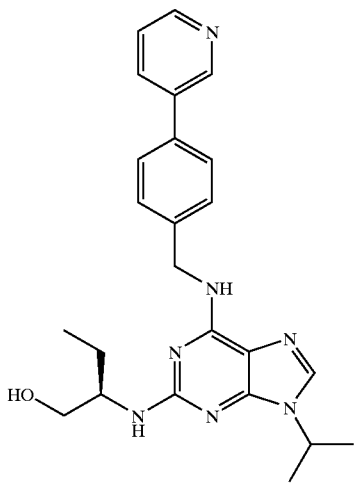

Formula XIII or a pharmaceutically acceptable salt thereof.

9. A compound having the following formula:

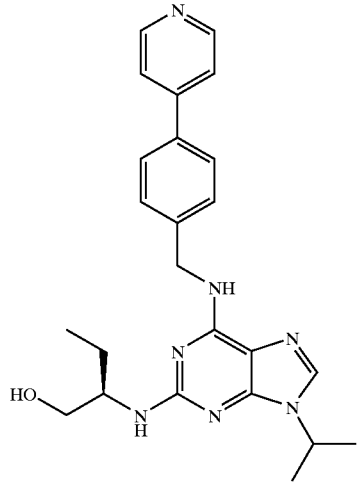

Formula XIV or a pharmaceutically acceptable salt thereof.

10. A compound having the following formula:

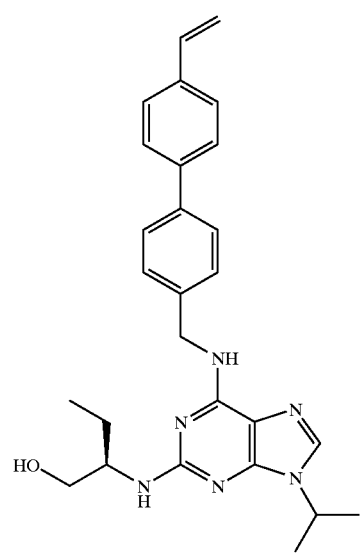

Formula XV or a pharmaceutically acceptable salt thereof.

11. A compound having the following formula:

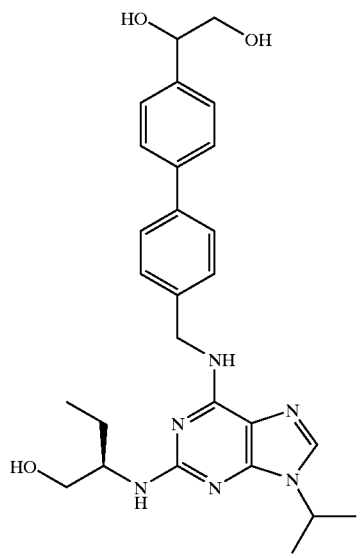

Formula XVI or a pharmaceutically acceptable salt thereof.

12. A compound having the following formula:

Formula XVII

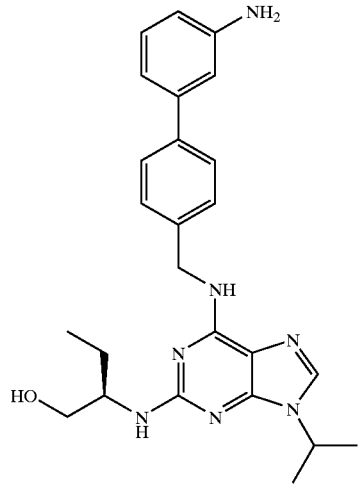

or a pharmaceutically acceptable salt thereof.

13. A compound having the following formula:

Formula XVIII

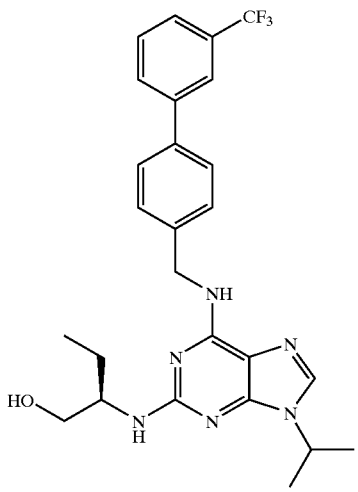

or a pharmaceutically acceptable salt thereof.

14. A compound having the following formula:

Formula XIX

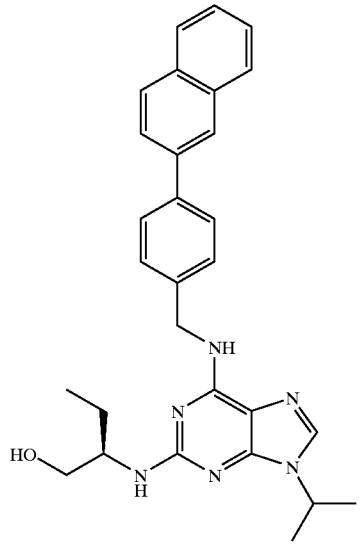

or a pharmaceutically acceptable salt thereof.

15. A compound having the following formula:

Formula XX

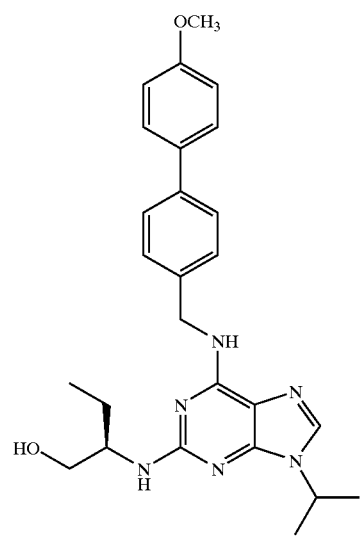

or a pharmaceutically acceptable salt thereof.

16. A compound having the following formula:

Formula XXI

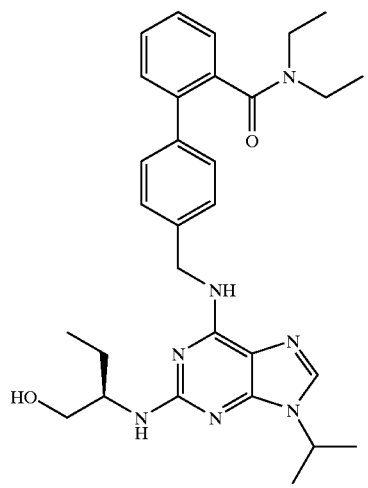

or a pharmaceutically acceptable salt thereof.

17. A compound having the following formula:

Formula XXII

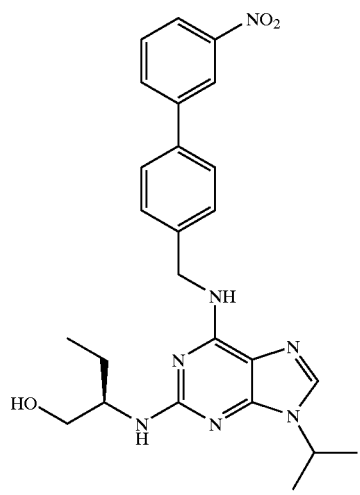

or a pharmaceutically acceptable salt thereof.

18. A compound having the following formula:

Formula XXIII

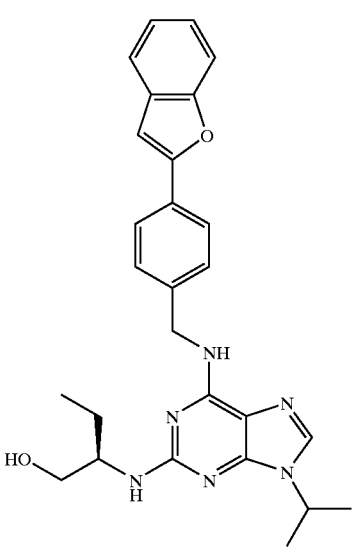

or a pharmaceutically acceptable salt thereof.

19. A compound having the following formula:

Formula XXIV

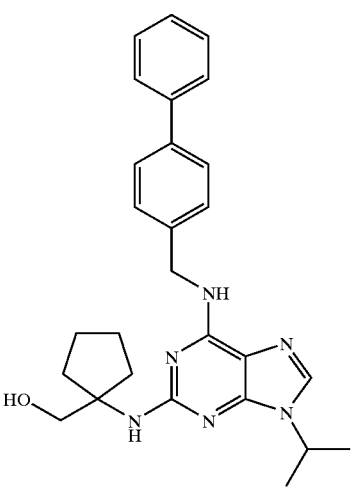

or a pharmaceutically acceptable salt thereof.

20. A compound having the following formula:

Formula XXVIII

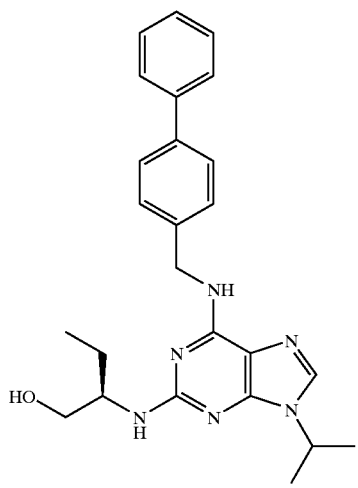

or a pharmaceutically acceptable salt thereof.

21. A compound having the following formula:

Formula XXXVI

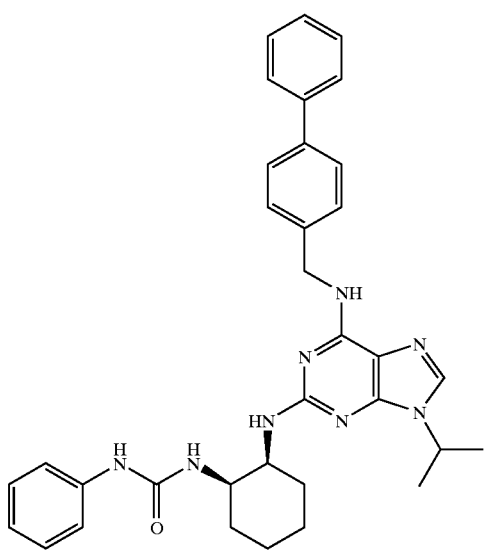

or a pharmaceutically acceptable salt thereof.

22. A compound according to claim 1, wherein the compound has the following formula:

Formula XXXIX

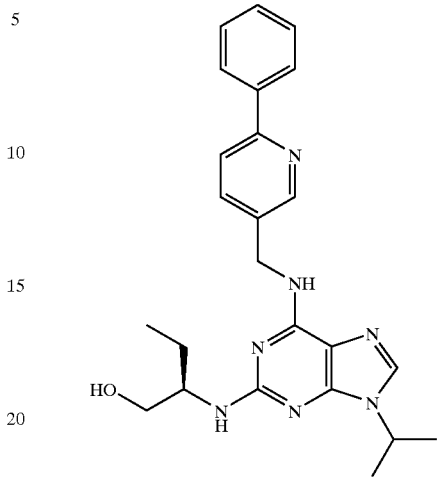

or a pharmaceutically acceptable salt thereof.

23. A compound having the following formula:

Formula LII

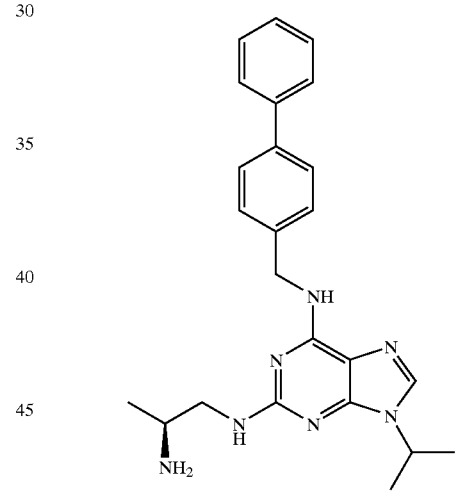

or a pharmaceutically acceptable salt thereof.

24. A compound having the following formula:

Formula LIII

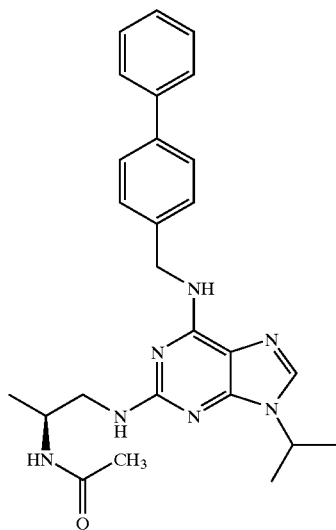

or a pharmaceutically acceptable salt thereof.

25. A compound of the following formula:

Formula III

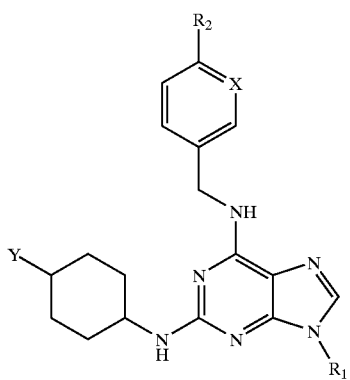

wherein:

$R_1$ are the same or different and independently selected from the group consisting of:
H;
$C_1$–$C_4$-straight chain alkyl; and
$C_3$–$C_4$-branched chain alkyl;

X=
N; or
CH;

$R_2$=
phenyl; substituted phenyl, wherein the substituents (1–2 in number) are in any position and independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, $C(O)NHCHR_1CH_2OH$;
heterocycles selected from the group consisting of:
2-pyridyl;
3-pyridyl;
4-pyridyl;
5-pyrimidyl;
thiophene-2-yl;
thiophene-3-yl;
2-furanyl;
3-furanyl;
2-benzofuranyl;
benzothiophene-2-yl;
2-pyrrolyl;
3-pyrrolyl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;

Y=
$NHR_1$;
$NHC(O)R_1$;
$NHSO_2R_1$;
$NHC(O)NHR_1$; or
$NHC(O)OR_6$;

$R_6$=
$C_1$–$C_4$-straight chain alkyl;
$C_3$–$C_4$-branched chain alkyl;
$C_2$–$C_4$-alkenyl chain; or
or a pharmaceutically acceptable salt thereof.

26. A compound according to claim 25, wherein X=N.

27. A compound according to claim 25, wherein the compound has the following formula:

Formula VIII

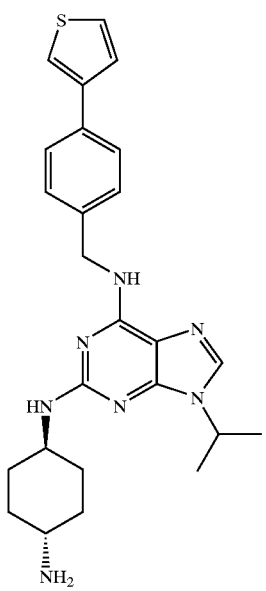

or a pharmaceutically acceptable salt thereof.

28. A compound according to claim 25, wherein the compound has the following formula:

Formula IX or a pharmaceutically acceptable salt thereof.

29. A compound according to claim 25, wherein the compound has the following formula:

Formula X or a pharmaceutically acceptable salt thereof.

30. A compound having the following formula:

Formula XXV or a pharmaceutically acceptable salt thereof.

31. A compound having the following formula:

Formula XXVI or a pharmaceutically acceptable salt thereof.

32. A compound having the following formula:

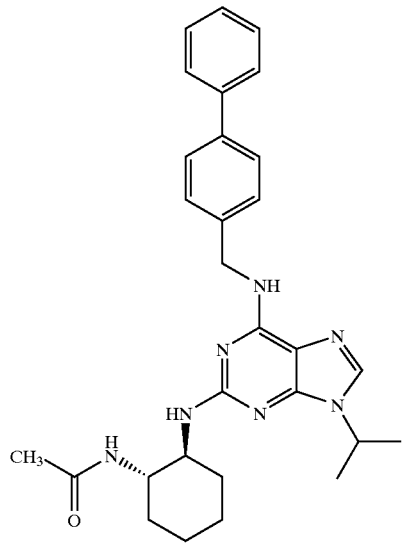

Formula XXVII or a pharmaceutically acceptable salt thereof.

33. A compound having the following formula:

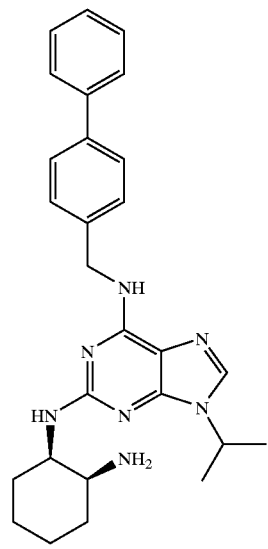

Formula XXIX or a pharmaceutically acceptable salt thereof.

34. A compound according to claim 25, wherein the compound has the following formula:

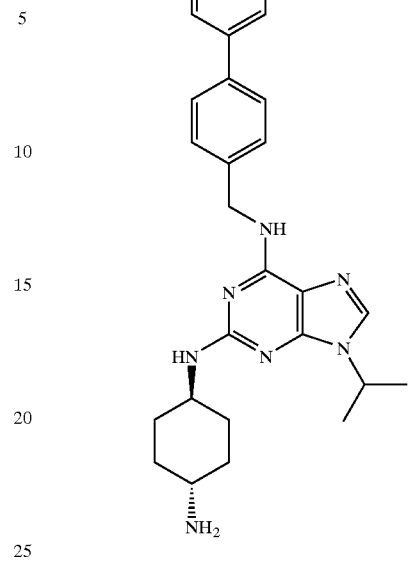

Formula XXX or a pharmaceutically acceptable salt thereof.

35. A compound according to claim 25, wherein the compound has the following formula:

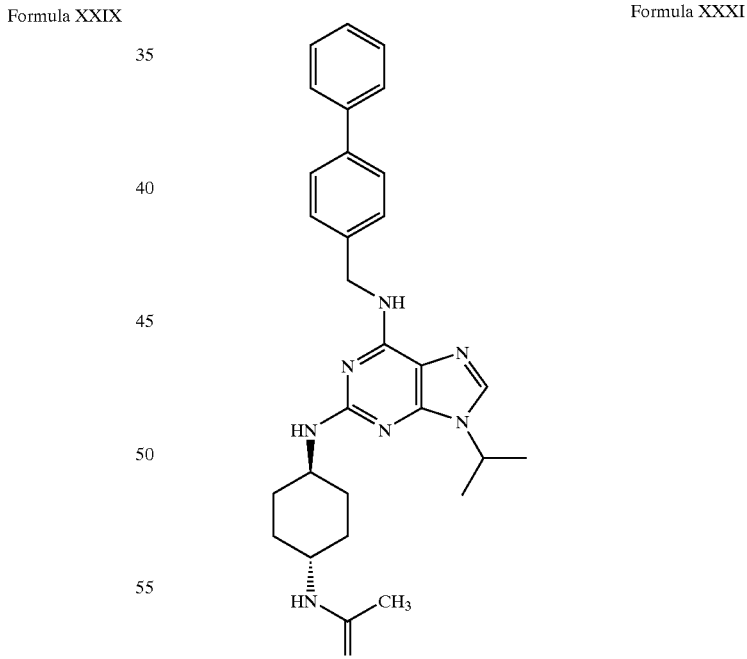

Formula XXXI or a pharmaceutically acceptable salt thereof.

36. A process according to claim 7 further comprising:

reacting a first starting compound of the formula:

Formula IV with a second starting compound of the formula

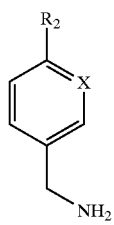

Formula XV under conditions effective to form the third intermediate compound.

37. A compound according to claim 25, wherein the compound has the following formula:

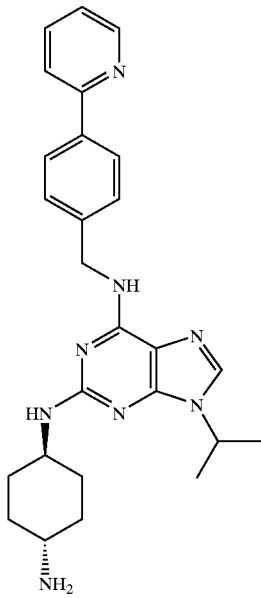

Formula XXXIII or a pharmaceutically acceptable salt thereof.

38. A pharmaceutical composition of matter comprising the compound of claim 1 and one or more pharmaceutical excipients.

39. A compound according to claim 25, wherein the compound has the following formula:

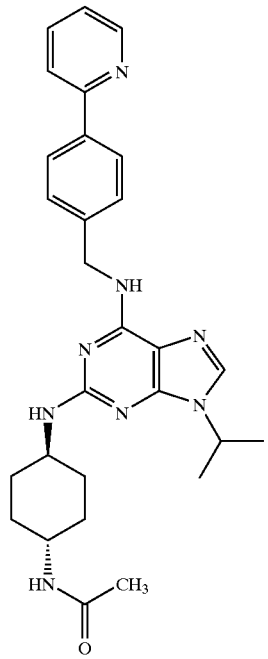

Formula XXXV or a pharmaceutically acceptable salt thereof.

40. A compound according to claim 25, wherein the compound has the following formula:

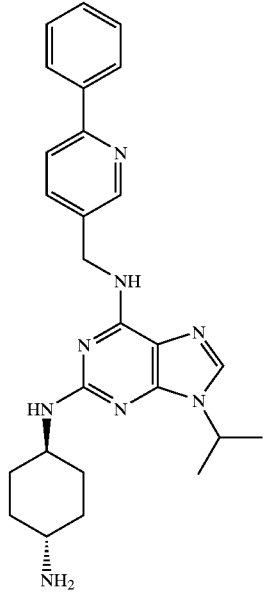

Formula XXXVII or a pharmaceutically acceptable salt thereof.

41. A compound according to claim 25, wherein the compound has the following formula:

Formula XXXVIII

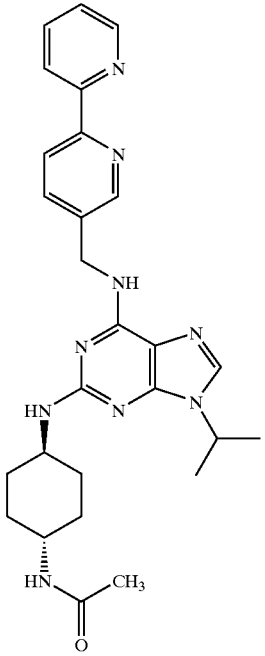

or a pharmaceutically acceptable salt thereof.

42. A compound according to claim 25, wherein the compound has the following formula:

Formula XL

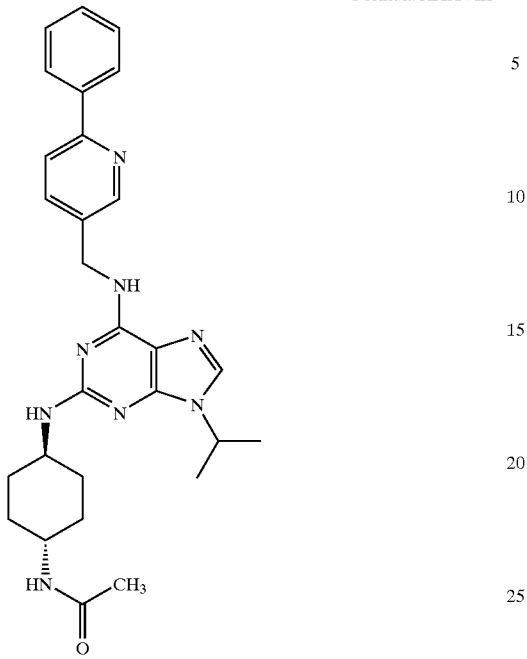

or a pharmaceutically acceptable salt thereof.

43. A compound according to claim 25, wherein the compound has the following formula:

Formula XLI

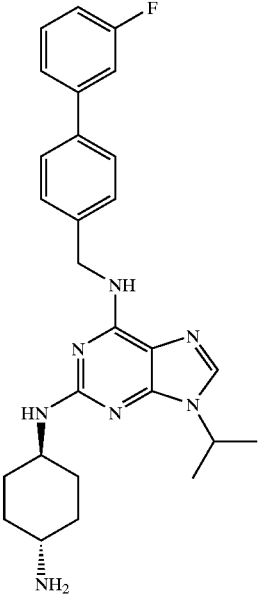

or a pharmaceutically acceptable salt thereof.

44. A compound according to claim 25, wherein the compound has the following formula:

Formula XLII

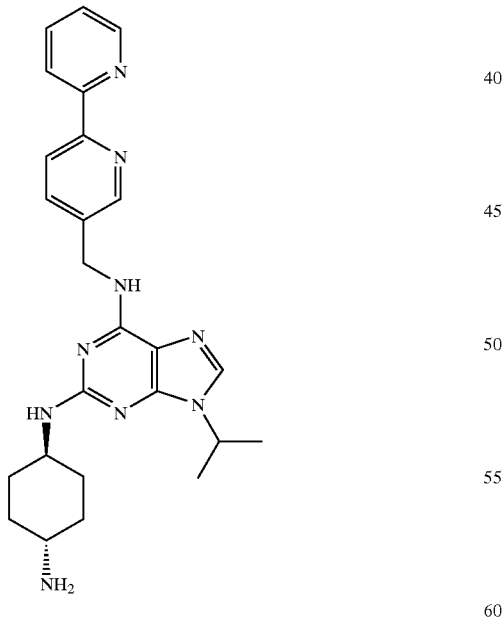

or a pharmaceutically acceptable salt thereof.

45. A compound according to claim 25, wherein the compound has the following formula:

141

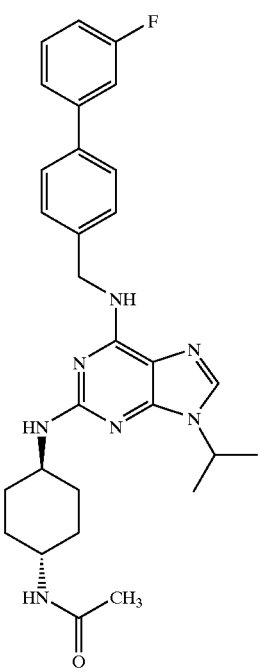

Formula XLIII or a pharmaceutically acceptable salt thereof.

46. A compound according to claim 25, wherein the compound has the following formula:

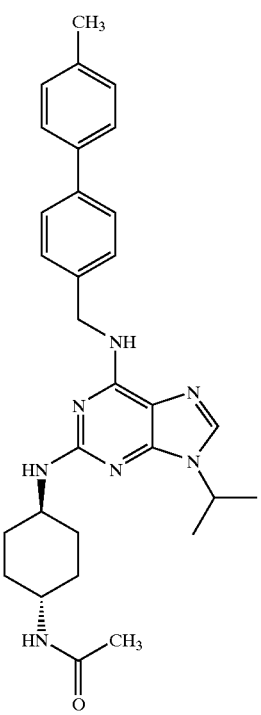

Formula XLIV or a pharmaceutically acceptable salt thereof.

47. A compound according to claim 25, wherein the compound has the following formula:

142

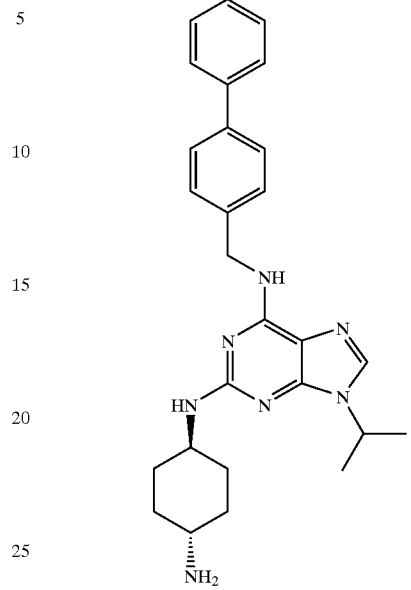

Formula XLV or a pharmaceutically acceptable salt thereof.

48. A compound according to claim 25, wherein the compound has the following formula:

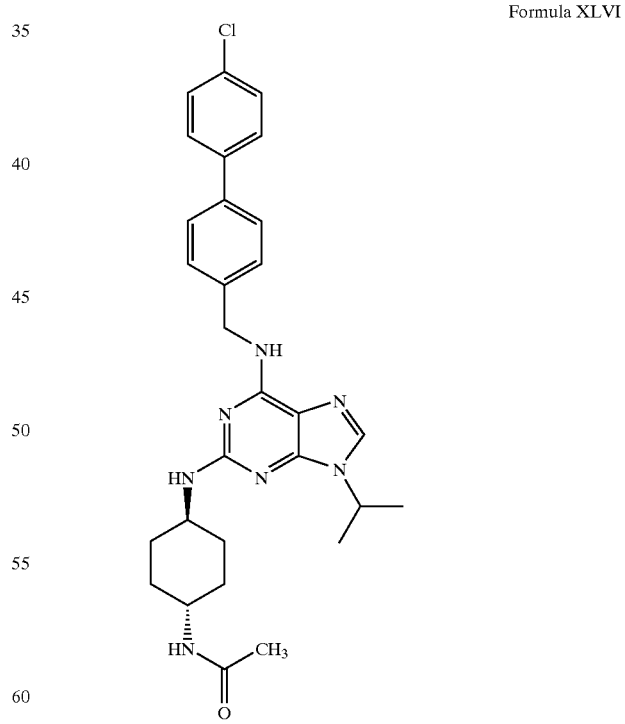

Formula XLVI or a pharmaceutically acceptable salt thereof.

49. A compound according to claim 25, wherein the compound has the following formula:

Formula XLVII

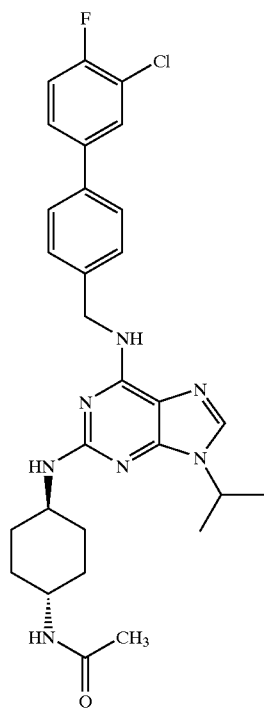

or a pharmaceutically acceptable salt thereof.

50. A compound according to claim 25, wherein the compound has the following formula:

Formula XLVIII

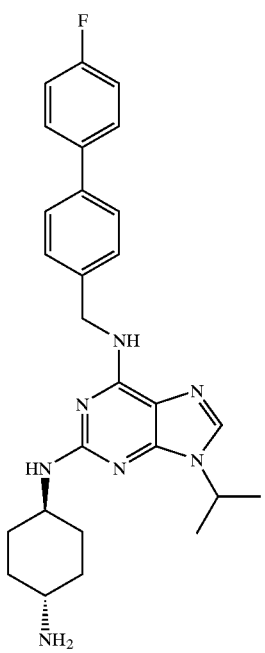

or a pharmaceutically acceptable salt thereof.

51. A compound according to claim 25, wherein the compound has the following formula:

Formula IL

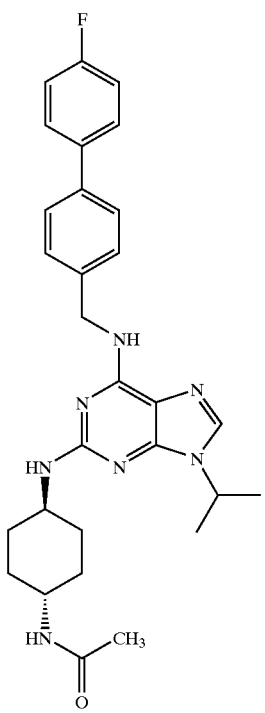

or a pharmaceutically acceptable salt thereof.

52. A compound according to claim 25, wherein the compound has the following formula:

Formula L

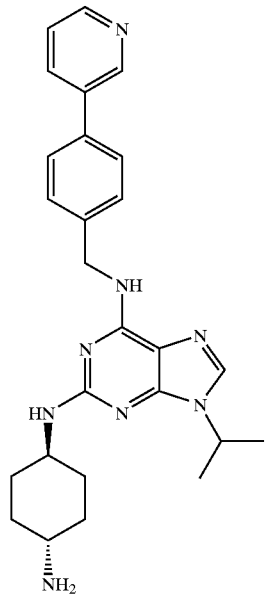

or a pharmaceutically acceptable salt thereof.

53. A compound according to claim 25, wherein the compound has the following formula:

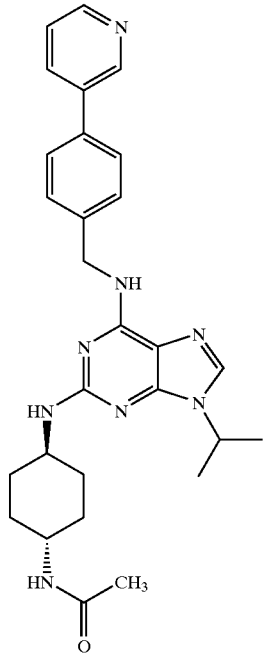

Formula LI or a pharmaceutically acceptable salt thereof.

54. A compound according to claim 25, wherein the compound has the following formula:

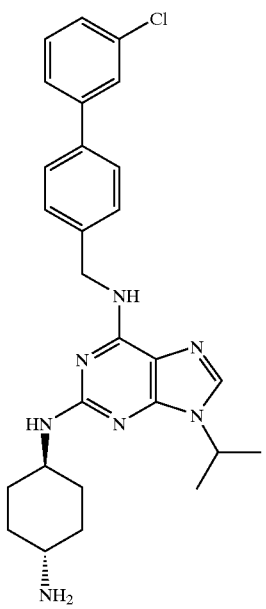

Formula LIV or a pharmaceutically acceptable salt thereof.

55. A compound according to claim 25, wherein the compound has the following formula:

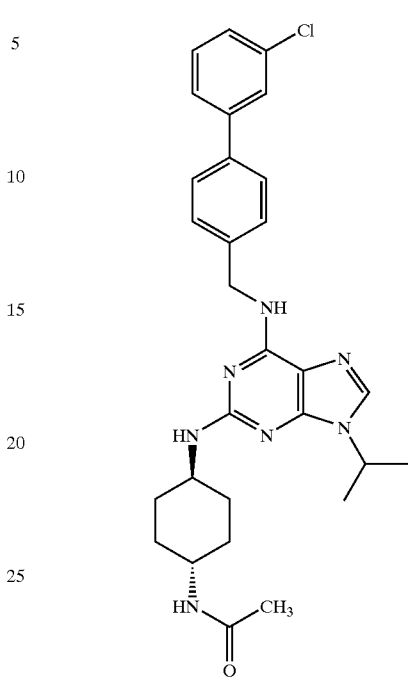

Formula LV or a pharmaceutically acceptable salt thereof.

56. A compound according to claim 25, wherein the compound has the following formula:

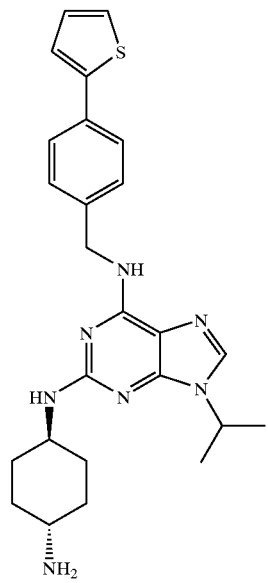

Formula LVI or a pharmaceutically acceptable salt thereof.

57. A compound according to claim 25, wherein the compound has the following formula:

147

Formula LVII

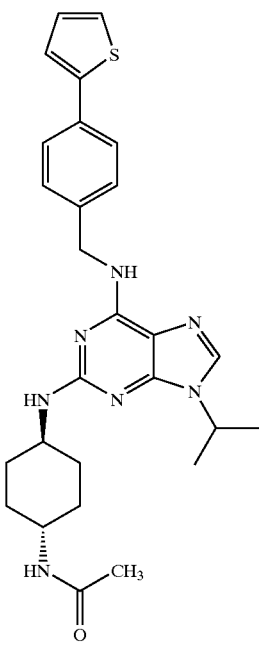

or a pharmaceutically acceptable salt thereof.

58. A compound according to claim 25, wherein the compound has the following formula:

Formula LVIII

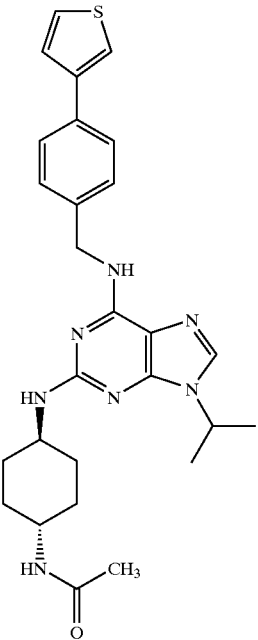

or a pharmaceutically acceptable salt thereof.

148

59. A process for preparation of a purine derivative compound of the formula:

Formula X

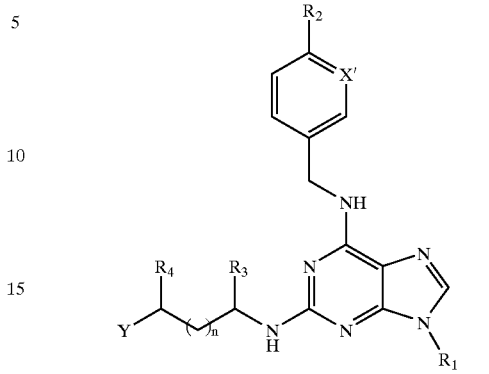

wherein:
$R_1$ are the same or different and independently selected from the group consisting of:
H;
$C_1$–$C_4$-straight chain alkyl; and
$C_3$–$C_4$-branched chain alkyl;
X=N;
$R_2$=
phenyl; substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, phenyl, $C(O)NHCHR_1CH_2OH$;
1-naphthyl;
2-naphthyl;
heterocycles selected from the group consisting of:
2-pyridyl;
3-pyridyl;
4-pyridyl;
5-pyrimidyl;
thiophene-2-yl;
thiophene-3-yl;
2-furanyl;
3-furanyl;
2-benzofuranyl;
benzothiophene-2-yl;
2-pyrrolyl;
3-pyrrolyl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;
$R_3$ are the same or different and independently selected from the group consisting of:
H;
$C_1$–$C_4$-straight chain alkyl;
$C_3$–$C_4$-branched chain alkyl;
$C_2$–$C_4$-alkenyl chain;
$(CH_2)_n Ph$; and
$(CH_2)_n$-substituted phenyl, wherein the phenyl substituents are as defined above in $R_2$;

$R_4 =$

H;

$C_1$–$C_4$-straight chain alkyl; or $C_3$–$C_4$-branched chain alkyl;

$R_3$ and $R_4$ can be linked together by a carbon chain to form with intervening atoms a 5–8-membered ring;

n=0–3;

Y=

H;

$OR_1$;

$NHR_1$;

$NHC(O)R_3$;

$NHSO_2R_3$;

$NHC(O)NHR_3$;

$NHC(O)R_5$; or $NHC(O)OR_6$;

$R_5 = C_3$–$C_7$-cycloalkyl;

$R_6 =$ $C_1$–$C_4$-straight chain alkyl;

$C_3$–$C_4$-branched chain alkyl;

$C_2$–$C_4$-alkenyl chain;

$(CH_2)_n$Ph; or $(CH_2)_n$-substituted phenyl, wherein the phenyl substituents are as defined above in $R_2$;

or a pharmaceutically acceptable salt thereof, said process comprising:

reacting a first intermediate compound of the formula:

Formula IX where

Z=Br or I with a compound of the formula: $R_2$—$B(OH)_2$, $R_2$—$Sn(n\text{-}Bu)_3$, $R_2$—$Sn(Me)_3$, or mixtures thereof, under conditions effective to form the purine derivative compound.

60. A process according to claim 59 further comprising:

reacting a second intermediate compound of the formula:

Formula VII with a second compound of the formula:

under conditions effective to form the first intermediate compound.

61. A process according to claim 60, wherein if Y in the second compound is $NH_2$, said process further comprises:

reacting the purine derivative compound with $R_3C(O)Cl$ or $R_3SO_2Cl$ or $R_3NCO$ or $R_3OC(O)Cl$ under conditions effective to form a final product having the same formula as the purine derivative compound except that Y is $NHC(O)R_3$ or $NHSO_2R_3$ or $NHC(O)NHR_3$ or $NHC(O)OR_6$.

62. A process according to claim 60 further comprising:

reacting a third intermediate compound of the formula:

Formula VI with a compound of the formula $R_1$—Z under conditions effective to form the second intermediate compound.

63. A process according to claim 62 further comprising: reacting a first starting compound of the formula:

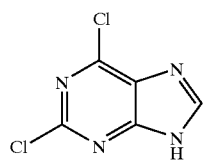
Formula IV with a second starting compound of the formula

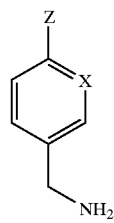
Formula V under conditions effective to form the third intermediate compound.

64. A compound according to claim 25, wherein the compound has the following formula:

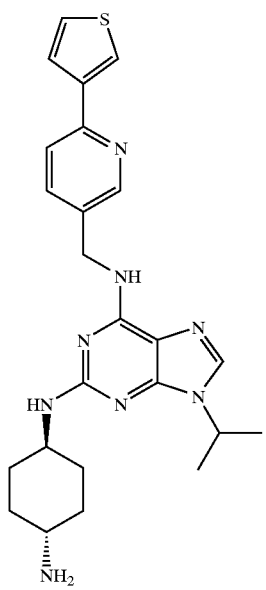
Formula LXIV or a pharmaceutically acceptable salt thereof.

65. A compound according to claim 25, wherein the compound has the following formula:

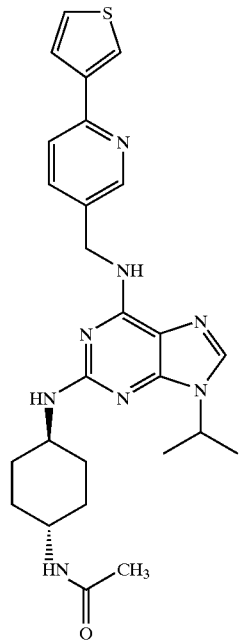
Formula LXV or a pharmaceutically acceptable salt thereof.

66. A process according to claim 59, wherein the purine derivative compound has the formula:

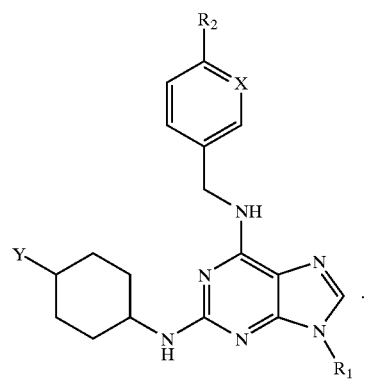
Formula III

67. A pharmaceutical composition of matter comprising the compound of claim 25 and one or more pharmaceutical excipients.

* * * * *